United States Patent
Chen et al.

(10) Patent No.: US 8,288,137 B2
(45) Date of Patent: Oct. 16, 2012

(54) **RECOMBINANT *ESCHERICHIA COLI* HAVING ENHANCED ACETYL-COENZYME A SYNTHETASE ACTIVITY FOR PRODUCING GLYEROL AND GLYCEROL-DERIVED PRODUCTS**

(75) Inventors: Qi Chen, Wallingford, PA (US); Qiong Cheng, Wilmington, DE (US); Andrew C. Eliot, Wilmington, DE (US); Kristin Ruebling-Jass, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/946,120

(22) Filed: Nov. 15, 2010

(65) Prior Publication Data

US 2012/0122168 A1    May 17, 2012

(51) Int. Cl.
*C12N 1/21*    (2006.01)
(52) U.S. Cl. .................... 435/146; 435/252.33; 435/159
(58) Field of Classification Search .................. None
See application file for complete search history.

(56) References Cited

U.S. PATENT DOCUMENTS 7,915,011 B2 *   3/2011   Chen et al. ................... 435/69.1
2009/0087887 A1   4/2009   Kataoka et al.

OTHER PUBLICATIONS

Kumari et al., "Regulation of Acetyl Coenzyme A Synthetase in *Escherichia coli*", J. of Bacteriology, Aug. 2000, p. 4173-4179.
Patel et al., "Substrate Specificity of Acetyl Coenzyme a Synthetase*", The Journal of Biological Chemistry, vol. 262, No. 15, Issue of May 25, 1987, pp. 7132-7134.
Lin et al., "Acetyl-CoA synthetase overexpression in *Escherichia coli* demonstrates more efficient acetate assimilation and lower acetate accumulation: a potential tool in metabolic engineering", Appl. Microbiol. Biotechnol. (2006) vol. 71, pp. 870-874.
Eiteman et al., "Overcoming acetate in *Escherichia coli* recombinant protein fermentations", TRENDS in Biotechnology, vol. 24, No. 11 (2006) pp. 530-536.
Phue et al., "Transcription levels of key metabolic genes are the cause for different glucose utilization pathways in *E. coli* B (BL21) and *E. coli* K (JM109)", Journal of Biotechnology 109 (2004) pp. 21-30.
De Mey et al., "Minimizing acetate formation in *E. coli* fermentations", J. Ind. Microbiol. Biotechnol (2007) vol. 34, pp. 689-700.

* cited by examiner

*Primary Examiner* — Hope Robinson
(74) *Attorney, Agent, or Firm* — Roger W. Herrell, Jr.

(57) ABSTRACT

Recombinant *Escherichia coli* (*E. coli*) bacteria that have enhanced acetyl-CoA synthetase activity and the ability to produce glycerol and glycerol-derived products, such as 3-hydroxypropionic acid, methylglyoxal, 1,2-propanediol, and 1,3-propanediol, are described. The recombinant *E. coli* comprise a promoter operably linked to a nucleotide sequence encoding a polypeptide having acetyl-CoA synthetase enzyme activity, wherein the promoter and nucleotide sequence are each independently either native or non-native.

6 Claims, No Drawings

RECOMBINANT ESCHERICHIA COLI HAVING ENHANCED ACETYL-COENZYME A SYNTHETASE ACTIVITY FOR PRODUCING GLYEROL AND GLYCEROL-DERIVED PRODUCTS

FIELD OF THE INVENTION

The invention relates to the fields of microbiology and molecular biology. More specifically, recombinant *Escherichia coli* (*E. coli*) having enhanced acetyl-coenzyme A (acetyl-CoA) synthetase activity and the ability to produce glycerol and glycerol-derived products, and methods of utilizing such recombinant bacteria are provided.

BACKGROUND OF THE INVENTION

The polyol 1,3-propanediol (PDO) is a monomer useful in the production of a variety of polymers including polyesters, polyurethanes, polyethers and cyclic compounds. The polymers are ultimately used in fibers, films, coatings, composite materials, solvents, anti-freeze, copolyesters and other value-added applications. Although 1,3-propanediol may be produced by chemical synthesis, biological production via fermentation provides several advantages over chemical synthesis, including providing a sustainable, more environmentally friendly process. Fermentation using recombinantly-engineered bacteria using inexpensive carbon sources such as glucose or other sugars to produce 1,3-propanediol are known (see for example, U.S. Pat. No. 5,686,276, U.S. Pat. No. 6,358,716, U.S. Pat. No. 6,136,576, and U.S. Pat. No. 7,524,660). However, fermentative routes to producing 1,3-propanediol generate residual materials, such as acetate, which can compromise the quality of the polymers produced from this monomer. Consequently, the residual materials need to be removed from the 1,3-propanediol product by various separation methods, including ion exchange and distillation. The presence of acetate is particularly problematic because a high ion exchange capacity is required to reduce its concentration to acceptable levels.

Therefore, there is a need to reduce the amount of acetate produced during the production of 1,3-propanediol and other glycerol-derived products by fermentation to increase the capacity of the separation process required to obtain a product having acceptable purity levels. Additionally, acetate is a by-product known to inhibit bacterial growth (Lin et al., *Appl. Microbiol. Biotechnol.* 71:870-874, 2006), so a decrease in acetate production may lead to increased yields of 1,3-propanediol.

SUMMARY OF THE INVENTION

In one embodiment, the invention provides a recombinant *E. coli* comprising a promoter operably linked to a nucleotide sequence encoding a polypeptide having acetyl-CoA synthetase enzyme activity; wherein the promoter and nucleotide sequence are each independently either native or non-native; further wherein said recombinant *E. coli* has enhanced acetyl-CoA synthetase enzyme activity relative to a parent *E. coli* from which the recombinant *E. coli* was derived, and said recombinant *E. coli* produces glycerol, 1,3-propanediol and/or 3-hydroxypropionic acid; provided that if the promoter and nucleotide sequence are both native, said recombinant *E. coli* comprises at least two copies of the promoter and nucleotide sequence.

In another embodiment, the invention provides a process for making glycerol, 1,3-propanediol, and/or 3-hydroxypropionic acid comprising:
a) culturing a recombinant *E. coli* as described herein in a suitable growth medium; and
b) optionally, recovering the glycerol, 1,3-propanediol, and/or 3-hydroxypropionic acid produced.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5(a bis), and Section 208 and Annex C of the Administrative Instructions). The symbols and format used for nucleotide and amino acid sequence data comply with the rules set forth in 37 C.F.R. §1.822.

TABLE A

Summary of Gene and Protein SEQ ID Numbers

| Gene | Coding Sequence SEQ ID NO: | Encoded Protein SEQ ID NO: |
|---|---|---|
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| dhaT from *Klebsiella pneumoniae* | 23 | 24 |
| dhaX gene from *Klebsiella pneumoniae* | 25 | 26 |
| acs from *Escherichia coli* | 27 | 28 |
| acs1 from *Saccharomyces cerevisiae* | 29 | 30 |
| acs2 from *Saccharomyces cerevisiae* | 31 | 32 |

SEQ ID NO:33 is the nucleotide sequence of the phage T5 promoter.

SEQ ID NO:34 is the nucleotide sequence of the Pcat promoter.

SEQ ID NO:35 is the nucleotide sequence of plasmid pSYCO101.

SEQ ID NO:36 is the nucleotide sequence of plasmid pSYCO103.

SEQ ID NO:37 is the nucleotide sequence of plasmid pSYCO106.

SEQ ID NO:38 is the nucleotide sequence of plasmid pSYCO109.

SEQ ID NO:39 is the nucleotide sequence of plasmid pSYCO400/AGRO.

SEQ ID NOs:40-51, 56, 57, 59, 60, 66-71, 73, and 74 are nucleotide sequences of primers used in the Examples herein.

SEQ ID NO:52 is the nucleotide sequence of plasmid pDCQ702, as described in Example 1 herein.

SEQ ID NO:53 is the nucleotide sequence of plasmid pDCQ703, as described in Example 1 herein.

SEQ ID NO:54 is the nucleotide sequence of the loxP-$Kan^R$-loxP-PT5 cassette, as described in Example 1 herein.

SEQ ID NO:55 is the nucleotide sequence of the loxP-$Kan^R$-loxP-Pcat cassette, as described in Example 1 herein.

SEQ ID NO:58 is the coding sequence of the *E. coli* fucP gene.

SEQ ID NO:61 is the nucleotide sequence of plasmid pMTP1.5fucP, described in Example 2 herein.

SEQ ID NO:62 is the nucleotide sequence of the synthetic linker sequence used in the construction of plasmid pMTP1.5fucPpmeI, as described in Example 2 herein.

SEQ ID NO:63 is the nucleotide sequence of plasmid pMTP1.6fucP, described in Example 2 herein.

SEQ ID NO:64 is the nucleotide sequence of plasmid pDCQ804, described in Example 2 herein.

SEQ ID NO:65 is the nucleotide sequence of plasmid pDCQ805, described in Example 2 herein.

SEQ ID NOs:72 and 75 are the nucleotide sequences of the TaqMan® probes described in Example 7 herein.

SEQ ID NO:76 is the nucleotide sequence of plasmid pDCQ806, described in Examples 8-10 herein.

SEQ ID NO:77 is the nucleotide sequence of plasmid pDCQ807, described in Examples 8-10 herein.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "acetyl-CoA synthetase enzyme activity" refers to a polypeptide responsible for an enzyme activity that catalyzes the conversion of acetate+Coenzyme A+ATP to acetyl-CoA+diphosphate+AMP. Typical of acetyl-CoA synthetase is EC 6.2.1.1. Acetyl-CoA synthetase is encoded by the gene acs.

The term "enhanced acetyl-CoA synthetase enzyme activity" as used herein means that the recombinant *E. coli* disclosed herein have a higher expression level, also referred to herein as "overexpression", of an acs gene encoding a polypeptide having acetyl-CoA synthetase activity when compared to the expression level in the parent *E. coli* from which the recombinant *E. coli* was derived. The expression level of acs can be determined using real-time PCR to determine the acs transcript levels in the *E. coli* as described in detail in Example 4 herein below.

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (EC 4.2.1.30) and a diol dehydratase (EC 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca,* and *Lactobacillus reuteri,* among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "β" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae, Citrobacter freundii*, and *Clostridium pasteurianum*. Each of these genes encode a polypeptide belonging to the family of type III alcohol dehydrogenases, which exhibits a conserved iron-binding motif, and has a preference for the NAD$^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+NAD$^+$ to 3-phospho-D-glyceroyl-phosphate+NADH+H$^+$. Typical of glyceraldehyde-3-phosphate dehydrogenase is EC 1.2.1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than NAD$^+$/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant *E. coli* disclosed herein. The carbon source may comprise monosaccharides such as glucose and fructose, oligosaccharides such as lactose or sucrose, and polysaccharides.

The terms "host cell" and "host bacterium" are used interchangeably herein and refer to a bacterium capable of receiving foreign or heterologous genes and capable of expressing those genes to produce an active gene product.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native promoter" refers to a promoter linked to a gene in the same manner in which it is normally found in a host microorganism.

The term "non-native promoter" refers to a promoter linked to a gene to which it is not normally linked.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*. 5:151-153 (1989); Higgins, D. G. et al., *Comput. Appl. Biosci.* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are recombinant *E. coli* that have the ability to produce glycerol and glycerol derived products and also have enhanced acetyl-CoA synthetase enzyme activity. The enhanced acetyl-CoA synthetase enzyme activity is due to overexpression of an acs gene encoding a polypeptide having acetyl-CoA synthetase activity. As a consequence of having enhanced acetyl-CoA synthetase enzyme activity, the recombinant *E. coli* disclosed herein produce less acetate during fermentation. The lower concentration of acetate in the fermentation broth simplifies the separation and purification of the desired products, i.e., glycerol and glycerol derived products such as 3-hydroxypropionic acid, methylglyoxal, 1,2-propanediol, or 1,3-propanediol.

The recombinant *E. coli* disclosed herein comprise a promoter operably linked to a nucleotide sequence encoding a polypeptide having acetyl-CoA synthetase enzyme activity. The promoter and nucleotide sequence encoding a polypeptide having acetyl-CoA synthetase enzyme activity are each independently either native or non-native. Specifically, the promoter can be non-native and the nucleotide sequence encoding a polypeptide having acetyl-CoA synthetase enzyme activity can be native; the promoter can be native and the nucleotide sequence encoding a polypeptide having acetyl-CoA synthetase enzyme activity can be non-native; both the promoter and the nucleotide sequence encoding a polypeptide having acetyl-CoA synthetase enzyme activity can be non-native; and both the promoter and the nucleotide sequence encoding a polypeptide having acetyl-CoA synthetase enzyme activity can be native if the recombinant *E. coli* comprises at least two copies of the promoter and the nucleotide sequence.

The acs gene is usually expressed at very low levels in *E. coli* K strains (Phue et al., *J. Biotechnol.* 109:21-30, 2004). One approach to enhancing the acetyl-Co synthetase activity in *E. coli* in order to reduce acetate accumulation during fermentation is to overexpress the native acs gene by replacing the native promoter with a non-native promoter. Therefore, in one embodiment the recombinant *E. coli* disclosed herein comprises a non-native promoter and a native nucleotide sequence encoding a polypeptide having acetyl-CoA synthetase enzyme activity.

In one embodiment, the native nucleotide sequence encoding a polypeptide having acetyl-CoA synthetase enzyme activity is the coding sequence of the acs gene from *E. coli* as set forth in SEQ ID NO:27, which encodes the polypeptide having the amino acid sequence set forth in SEQ ID NO:28. In one embodiment, the polypeptide having acetyl-CoA synthetase enzyme activity has at least 95% amino acid identity, based on the Clustal V method of alignment, when compared to the amino acid sequence set forth in SEQ ID NO:28.

Suitable non-native promoters are well known in the art and include, but are not limited to, CYC1, HIS3, GAL1, GAL10, ADH1, PGK, PHO5, GAPDH, ADC1, TRP1, URA3, LEU2, ENO, and lac, ara, tet, trp, IPL, IPR, T5, T7, tac, Pcat, and trc, amy, apr, and npr promoters. In one embodiment, the non-native promoter is a strong phage T5 promoter (Deuschle et al., *EMBO* 5:2987-2994, 1986). In one embodiment, the phage T5 promoter has a nucleotide sequence as set forth in SEQ ID NO:33. This sequence containing a T5 promoter, lacO site and ribosomal binding site can be synthesized from the pQE30 vector available from Qiagen (Valencia, Calif.). In another embodiment, the T5 promoter has a nucleotide sequence having at least 95% sequence identity, based on the BLASTN method of alignment, when compared to the nucleotide sequence set forth in SEQ ID NO:33

In another embodiment, the non-native promoter is a Pcat promoter found driving the expression of the chloramphenicol acetyl transferase encoding gene on plasmid R6/5 (Stuber et al., *Proc. Natl. Acad. Sci. USA*, 78:167-171, 1981). In one embodiment, the Pcat promoter has a nucleotide sequence as set forth in SEQ ID NO:34. In another embodiment, the Pcat promoter has a nucleotide sequence having at least 95% sequence identity, based on the BLASTN method of alignment, when compared to the nucleotide sequence set forth in SEQ ID NO:34.

In another embodiment, the recombinant E. coli disclosed herein comprises a non-native promoter and a non-native nucleotide sequence encoding a polypeptide having acetyl-CoA synthetase enzyme activity. Any of the non-native promoters listed above may be used. In one embodiment, the non-native promoter is a T5 promoter, as described above. In another embodiment, the promoter is a Pcat promoter, as described above.

The acs genes from various sources provide suitable non-native nucleotide sequences encoding a polypeptide having acetyl-CoA synthetase enzyme activity for use as disclosed herein. Examples of acs genes include, but are not limited to, acs genes from *Yersinia pestis*, *Salmonella typhimurium*, *Pseudomonas fluorescens*, and *Saccharomyces cerevisiae*.

In one embodiment, the nucleotide sequence encoding a polypeptide having acetyl-CoA synthetase enzyme activity is the coding sequence of the acs1 gene from *Saccharomyces cerevisiae* as set forth in SEQ ID NO:29, which encodes the polypeptide having the amino acid sequence set forth in SEQ ID NO:30. In one embodiment, the polypeptide having acetyl-CoA synthetase enzyme activity has at least 95% amino acid identity, based on the Clustal V method of alignment, when compared to the amino acid sequence set forth in SEQ ID NO:30.

In another embodiment, the nucleotide sequence encoding a polypeptide having acetyl-CoA synthetase enzyme activity is the coding sequence of the acs2 gene from *Saccharomyces cerevisiae* as set forth in SEQ ID NO:31, which encodes the polypeptide having the amino acid sequence set forth in SEQ ID NO:32. In one embodiment, the polypeptide having acetyl-CoA synthetase enzyme activity has at least 95% amino acid identity, based on the Clustal V method of alignment, when compared to the amino acid sequence set forth in SEQ ID NO:32.

In another embodiment, the recombinant E. coli disclosed herein comprises a native promoter and a non-native nucleotide sequence encoding a polypeptide having acetyl-CoA synthetase enzyme activity. Any of the non-native nucleotide sequences encoding a polypeptide having acetyl-CoA synthetase enzyme activity discussed above may be used with the native promoter.

In another embodiment, the recombinant E. coli disclosed herein comprises at least two copies of the native promoter and the native nucleotide sequence encoding a polypeptide having acetyl-CoA synthetase enzyme activity. At least two copies are necessary in order for the recombinant E. coli to have enhanced acetyl-CoA synthetase enzyme activity relative to the parent E. coli strain, which contains one copy of the native acs gene.

The coding sequence of acs genes encoding polypeptides having acetyl-CoA synthetase enzyme activity may be used to isolate nucleotide sequences encoding homologous polypeptides from the same or other microbial species. For example, homologs of the genes may be identified using sequence analysis software, such as BLASTN, to search publicly available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.*, 89: 392, (1992)). For example, the nucleotide sequences encoding the polypeptides having acetyl-CoA synthetase enzyme activity described above may be employed as a hybridization probe for the identification of homologs.

One of ordinary skill in the art will appreciate that genes encoding these polypeptides isolated from other sources may also be used in the recombinant E. coli disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding polypeptides having acetyl-CoA synthetase enzyme activity may be isolated using PCR (see, e.g., U.S. Pat. No. 4,683,202) and primers designed to bound the desired sequence, if this sequence is known. Other methods of gene isolation are well known to one skilled in the art such as by using degenerate primers or heterologous probe hybridization. The nucleotide sequences can also be chemically synthesized or purchased from vendors such as DNA2.0 Inc. (Menlo Park, Calif.).

Overexpression of an acs gene encoding a polypeptide having acetyl CoA synthetase enzyme activity may be effected using one of many methods known to one skilled in the art. For example, the native or non-native nucleotide sequence encoding the polypeptide described above may be introduced into the E. coli bacterium on at least one multicopy plasmid, or by integrating one or more copies of the nucleotide sequence into the host genome. The introduced coding region(s) that is (are) either on a plasmid(s) or in the genome may be expressed from at least one highly active promoter, as described above. An integrated coding region may either be introduced as a part of a chimeric gene having its own promoter, or it may be integrated adjacent to a highly active promoter that is endogenous to the genome or in a highly expressed operon.

In one embodiment, the recombinant E. coli disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host E. coli may be used that naturally produce glycerol. In addition, E. coli may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In another embodiment, the recombinant *E. coli* disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (EC 4.2.1.30), diol dehydratase (EC 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (EC 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:23, encoded protein sequence set forth in SEQ ID NO:24).

*E. coli* can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:

phosphoenolpyruvate carboxylase typically characterized as EC 4.1.1.31
cob(I)alamin adenosyltransferase, typically characterized as EC 2.5.1.17
non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:

aerobic respiration control protein
methylglyoxal synthase
acetate kinase
phosphotransacetylase
aldehyde dehydrogenase A
aldehyde dehydrogenase B
triosephosphate isomerase
phosphogluconate dehydratase In another embodiment, the recombinant *E. coli* disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. patent application Ser. No. 12/815,461. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the *E. coli* gene aldB (coding sequence set forth in SEQ ID NO:15); AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence asset forth in SEQ ID NO:19).

Many of the modifications described above to improve 1,3-propanediol production by a recombinant *E. coli* can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA)

prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/or regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, Curr. Opin. Biotechnol. (1999) 10:411; Ross, et al., J. Bacteriol. (1998) 180:5375; deHaseth, et al., J. Bacteriol. (1998) 180:3019; Smolke and Keasling, Biotechnol. Bioeng. (2002) 80:762; Swartz, Curr. Opin. Biotech. (2001) 12:195; and Ma, et al., J. Bacteriol. (2002) 184:5733.

Recombinant E. coli containing the necessary changes in gene expression for overexpression of acs and production of microbial products including glycerol and glycerol derivatives, as described above, may be constructed using techniques well known in the art, some of which are exemplified in the Examples herein.

The construction of the recombinant E. coli disclosed herein may be accomplished using a variety of vectors and transformation and expression cassettes suitable for the cloning, transformation and expression of coding regions of acs genes and the genes necessary to produce glycerol and glycerol-derived products, as described above. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of a polypeptide having acetyl-CoA synthetase enzyme activity, the nucleotide sequence encoding the polypeptide is linked operably through initiation codons to selected expression control regions such that expression results in the formation of the appropriate messenger RNA.

Particularly useful in the present invention are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from *Klebsiella pneumoniae* and from *Saccharomyces cerevisiae*. Each vector contains the open reading frames dhaB1, dhaB2, dhaB3, dhaX (coding sequence set forth in SEQ ID NO:25), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:35, SEQ ID NO:36, SEQ ID NO:37, SEQ ID NO:38, and SEQ ID NO:39, respectively. The differences between the vectors are illustrated in the chart below [the prefix "p-" indicates a promoter; the open reading frames contained within each "( )" represent the composition of an operon]:

pSYCO101 (SEQ ID NO:35):
   p-trc (Dar1_GPP2) in opposite orientation compared to the other 2 pathway operons,
   p-1.6 long GI (dhaB1_dhaB2_dhaB3_dhaX), and
   p-1.6 long GI (orfY_orfX_orfW).

pSYCO103 (SEQ ID NO:36):
   p-trc (Dar1_GPP2) same orientation compared to the other 2 pathway operons,
   p-1.5 long GI (dhaB1_dhaB2_dhaB3_dhaX), and
   p-1.5 long GI (orfY_orfX_orfW).

pSYCO106 (SEQ ID NO:37):
   p-trc (Dar1_GPP2) same orientation compared to the other 2 pathway operons,
   p-1.6 long GI (dhaB1_dhaB2_dhaB3_dhaX), and
   p-1.6 long GI (orfY_orfX_orfW).

pSYCO109 (SEQ ID NO:38):
   p-trc (Dar1_GPP2) same orientation compared to the other 2 pathway operons,
   p-1.6 long GI (dhaB1_dhaB2_dhaB3_dhaX), and
   p-1.6 long GI (orfY_orfX).

pSYCO400/AGRO (SEQ ID NO:39):
   p-trc (Dar1_GPP2) same orientation compared to the other 2 pathway operons,
   p-1.6 long GI (dhaB1_dhaB2_dhaB3_dhaX), and
   p-1.6 long GI (orfY_orfX).
   p-1.20 short/long GI (scrK) opposite orientation compared to the pathway operons.

Once suitable expression cassettes are constructed, they are used to transform appropriate host bacterium. Introduction of the cassette containing the coding regions into the host bacterium may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise a suitable carbon substrate. Suitable carbon substrates include, but are not limited to, monosaccharides such as glucose and fructose, oligosaccharides such as lactose or sucrose, and polysaccharides. In one embodiment, the carbon substrate is glucose.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae, Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Typically bacterial cells are grown at 25 to 40° C. in an appropriate medium. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In one embodiment, a process for making glycerol, 1,3-propanediol, and/or 3-hydroxypropionic acid using the recombinant E. coli described above is provided. The process comprises the steps of culturing a recombinant E. coli, as described above, in a suitable growth medium, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation. For example, 1,3-propanediol can be purified from the fermentation broth using the methods disclosed by Adkesson et al. (U.S. Patent Application Publication No. 2005/0069997).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and Methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.).

The meaning of abbreviations is as follows: "sec" means second(s), "min" means minute(s), "h" means hour(s), "nm" means nanometer(s), "µL" means microliter(s), "mL" means milliliter(s), "L" means liter(s), "mM" means millimolar, "M" means molar, "g" means gram(s), "µg" means microgram(s), "ng" means nanogram(s), "bp" means base pair(s), "kbp" means kilobase pair(s), "rpm" means revolutions per minute, "ATCC" means American Type Culture Collection, Manassas, Va., "OD" means optical density, "OD550" means the optical density measured at 550 nm, "g" means the gravitation constant, "HPLC" means high performance liquid chromatography.

TABLE 1

Primers used in the Examples

| Primer | Sequence | SEQ ID NO: |
|---|---|---|
| acsPdown-catR | CGATGTTGGCAGGAATGGTGTGTTTGTGAA TTTGGCTCATTTTAGCTTCCTTAGCTCCTG | 40 |
| acsPdown-T5R | CGATGTTGGCAGGAATGGTGTGTTTGTGAA TTTGGCTCATATGAGTTAATTTCTCCTCTT | 41 |
| acsPup-loxKan5' | GTTGTCTTTAATCAATTGTAAGTGCATGTA AAATACCACTGTGCGTAGTCGTTGGCAAGC | 42 |
| Pcat up | ATAAGAATGCGGCCGCTGACATTAACCTAT AAAAATAGGCGTATC | 43 |
| T5 up | ATAAGAATGCGGCCGCCTATAAAAATAGGC GTATCACGAGGC-CCTTTC | 44 |
| acs down | CCAGCTTTGTTTAAACTTACGATGGCATCG CGATAGCCTGCTTC | 45 |
| Pcat down acs1 | TGTACGGCAGAGGGCGACATTTTAGCTTCC TTAGCTCCTG | 46 |
| Pcat down acs2 | TTATGTTCCTTGATTGTCATTTTAGCTTCC TTAGCTCCTG | 47 |
| acs1 up | CAGGAGCTAAGGAAGCTAAAATGTCGCCCT CTGCCGTACA | 48 |
| acs1 down | CCAGCTTTGTTTAAACTTACAACTTGACCG AATCAATTAGAT GTC | 49 |
| acs2 up | CAGGAGCTAAGGAAGCTAAAATGACAATCA AGGAACATAA | 50 |
| acs2 down | CCAGCTTTGTTTAAACTTATTTCTTTTTTT GAGAGA | 51 |

Example 1

Recombinant *E. Coli* Strains in which the Native acs Promoter is Replaced with Stronger Constitutive Promoters This Example describes increasing the expression of the acs gene in *E. coli* by replacing the native acs promoter with stronger constitutive promoters.

The constitutive phage T5 (PT5) promoter (SEQ ID NO:33) (Yuan, L. Z., et al, 2006, *Metab. Eng.* 8, 79-90) and the Pcat promoter (SEQ ID NO:34) upstream of the chloramphenicol resistance gene from pBHR1 (MoBiTec GmbH, Goettingen, Germany), were synthesized by DNA 2.0 (Menlo Park, Calif.). The 157 bp PT5 promoter and the 253 bp Pcat promoter were cloned into the FseI and PstI sites of pMODlinker-Kan. The pMODlinker-Kan plasmid was constructed from pMODlinker-Spec, which is described by Viitanen et al. (U.S. Patent Application Publication No. 2009/0246876, Example 6). A DNA fragment, containing a $Kan^r$ gene and its promoter, that confers resistance to kanamycin ($Kan^r$) was inserted between the NotI and PacI sites of the pMOD-Linker-Spec plasmid, replacing the DNA fragment that confers resistance to spectinomycin ($Spec^r$). The source of the $Kan^r$ gene and its promoter was plasmid pZB188/kan-XylA, which is described by Viitanen et al. (U.S. Pat. No. 7,741,119, Example 4). The resulting plasmids pDCQ702 (SEQ ID NO:52) and pDCQ703 (SEQ ID NO:53) contained the PT5 or Pcat promoter, respectively, downstream of the $Kan^R$ gene flanked by loxP sites. Plasmids pDCQ702 or pDCQ703 were used as the template to amplify the 1255 bp $loxP-Kan^R-loxP-PT5$ cassette (SEQ ID NO:54) or the 1351 bp $loxP-Kan^R-loxP-Pcat$ cassette (SEQ ID NO:55) by PCR. For the reaction with pDCQ702 as template, the primers were acsPup-loxKan5' and acsPdown-T5R (see Table 1). For the reaction with pDCQ703 as template, the primers were acsPup-loxKan5' primer and acsPdown-catR (see Table 1).

PCR was done using the following cycling conditions: 95° C. for 5 min, 35 cycles of 95° C. for 30 sec, 58° C. for 30 sec, 72° C. for 2 min and 72° C. for 10 min. High fidelity PfuUltra® II Fusion HS DNA polymerase (Stratagene; La Jolla, Calif.) was used in the PCR reaction. The PCR products were purified using QIAquick PCR Purification kit (Qiagen; Valencia, Calif.). The purified $loxP-Kan^R-loxP-PT5$ cassette or the $loxP-Kan^R-loxP-Pcat$ cassette was integrated upstream of the acs locus in an *E. coli* K12 strain by Lambda Red recombination (Datsenko, K. A., and Wanner, B. L. 2000, *Proc. Natl. Acad. Sci. USA* 97, 6640-6645). This *E. coli* strain was a derivative of MG1655 (ATCC No. 47076) comprising disruptions in the endogenous araBAD operon and the poxB gene in the chromosome. Disruptions of the araBAD operon and the poxB gene are not relevant to the acs promoter replacement described here. Briefly, the purified PCR products were transformed into the MG1655-derived host strain containing the pRedET1 plasmid (Gene Bridges, Germany) encoding the lambda Red recombinases. The integrants were selected on Luria-Bertani (LB) plates containing 25 µg/mL kanamycin. PCR was used to confirm integration of the cassette upstream of the acs gene. The $Kan^R$ marker flanked by the loxP sites was removed by Cre recombinase introduced from the temperature sensitive pCre-tet plasmid (Gene Bridges, Germany). The resulting strains were designated QC1549 (Pcat promoter) and QC1550 (PT5 promoter).

Example 2

Cloning of the Overexpressed *E. Coli* acs Gene on pMTP1.6fucP Plasmid

The acs gene operably linked to either the PT5 or Pcat promoter was cloned into the pMTP1.6fucP plasmid, a fucP overexpression vector, downstream of the fucP gene.
Construction of the pMTP1.6fucP Plasmid The origin of replication of the large native plasmid pMT100, described in U.S. Patent Application Publication No. 2008/0194032, from *E. coli* strain ATCC No. 13281 was amplified by PCR using primers MTori1, set forth in SEQ ID NO:56, and MTori2, set forth in SEQ ID NO:57. A HindIII restriction enzyme recognition site was present in one of the PCR primers. The resulting PCR product was digested with the restriction enzymes DraI and HindIII and ligated to the SspI/HindIII fragment of pK194, described by Jobling and Holmes (*Nucleic Acids Res.* 18:5315, 1990), that contains a multiple cloning site and a kanamycin resistance gene. The resulting plasmid was named pMTori. To make plasmids pMTP1.5 and pMTP1.6, the EcoRI/HindIII fragment from pMTori1 was replaced with the EcoRI/HindIII fragment from the respective pMP38 plasmid, described in U.S. Pat. No. 7,132,527. The designations "1.5" and "1.6" refer to the variants of the glucose isomerase promoter described in U.S. Pat. No. 7,132,527. The coding sequence of the *E. coli* fucP gene, set forth in SEQ ID NO:58 was amplified by PCR from genomic DNA from *E. coli* strain MG1655 (available from The American Type Culture Collection as ATCC No: 47076) using the primer pair set forth in SEQ ID NOs:59 and 60. The resulting blunt fragment was ligated with HindIII-digested and blunted pMTP1.5 to generate pMTP1.5fucP (SEQ ID NO:61). The sequence of the plasmid was verified.

A pmeI restriction site was added to pMTP1.5fucP by ligation of a synthetic linker sequence (set forth in SEQ ID NO:62) with ScaI and NotI digested pMTP1.5fucP plasmids. The synthetic linker sequence had an overhang of ccgg at the 5' end of the reverse strand. The resulting plasmid was designated as pMTP1.5fucPpmeI.

The plasmid pMTP1.6fucP (SEQ ID NO: 63) was generated by digesting pMTP1.5fucPpmeI and pMTP1.6 with BstEII. The larger fragment from the pMTP1.5fucPpmeI digest and the smaller fragment from the pMTP1.6 digest were then ligated. The sequence of the resulting plasmid was verified.
Cloning of the Overexpressed *E. coli* acs Gene Genomic DNA of QC1549 and QC1550 (described in Example 1) was used as the template for separate PCR reactions. Primers Pcat up and acs down (see Table 1) were used to amplify the Pcat-acs from QC1549. Primers T5 up and acs down were used to amplify the PT5-acs from QC1550. The PCR conditions were similar to those described in Example 1. The PCR products were purified, and digested with NotI and PmeI. The vector plasmid pMTP1.6fucP was also digested with NotI and PmeI, and ligated with the Pcat-acs or PT5-acs fragment. The resulting plasmids were designated pDCQ804 (SEQ ID NO:64) and pDCQ805 (SEQ ID NO:65), respectively. Plasmid sequences were confirmed by sequencing.

Examples 3-6

Production of 1,3-Propanediol by Strains Overexpressing acs

*E. coli* strain TTab/pSYCO400Agro is a strain that is capable of producing 1,3-propanediol (PDO) and glycerol. TTab/pSYCO400Agro was transformed with the acs overexpression plasmids pDCQ804 and pDCQ805, or pMTP1.6fucP.
*E. Coli* Strain TTab pSYCO400/AGRO (a PTS Minus Strain)

Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:66 and SEQ ID NO:67 using pKD3 as the template. The primer SEQ ID NO:66 contains 80 bp of homology to the 5'-end of aldB and 20 bp of homology to pKD3. Primer SEQ ID NO:67 contains 80 bp of homology to the 3' end of aldB and 20 bp homology to pKD3. The PCR products were gel-purified and electroporated into MG1655/pKD46 competent cells (U.S. Pat. No. 7,371,558). Recombinant strains were selected on LB plates with 12.5 mg/L of chloroamphenicol. The deletion of the aldB gene was confirmed by PCR, using the primer pair SEQ ID NO:68 and SEQ ID NO:69. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:68 and SEQ ID NO:69 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:39), described in U.S. Pat. No. 7,524,660 (Example 4), to generate strain TTab pSYCO400/AGRO.

As described in the cited references, strain TTab is a derivative of *E. coli* strain FM5 (ATCC No. 53911) containing the following modifications:
deletion of glpK, gldA, ptsHI, crr, edd, arcA, mgsA, qor, ackA, pta, aldA and aldB genes;
upregulation of galP, glk, btuR, ppc, and yqhD genes; and
downregulation of gapA gene.
Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

Transformation of *E. Coli* Strain TTab pSYCO400/AGRO with acs Overexpression Plasmids TTab/pSYCO400Agro was transformed with the acs overexpression plasmids pDCQ804 and pDCQ805, or pMTP1.6fucP (Example 2), and transformants were selected by growth on LB-Agar containing 25 μg/mL kanamycin. The successful transformants were designated PDO3043, PDO3044 and PDO3042, respectively. Multiple transformants of each strain were picked and their growth phenotype was examined initially using a Bioscreen C growth chamber [Bioscreen, Helsinki, Finland].

Colonies of each strain from the transformation plates were first grown in 150 μL of LA medium (1% tryptone, 0.5% yeast extract, 0.05% sodium chloride) containing 100 μg/mL spectinomycin and 25 μg/mL kanamycin in a Costar 96-well U bottom plate (Corning Inc., Corning, N.Y.). The plate was incubated at 37° C. with shaking. The fresh overnight cultures were diluted 1:100 into MOPS-TM3 medium containing 10 g/L glucose in a Bioscreen honeycomb plate. MOPS-TM3 is a minimal medium containing 50 mM MOPS buffer pH6.8, 6.0 mM potassium phosphate buffer pH 6.8, 2.04 g/L citric acid dihydrate, 2 g/L magnesium sulfate heptahydrate, 0.033 g/L ferric ammonium citrate, 0.5 g/L yeast extract, 3 g/L ammonium sulfate, 0.002 g/L $CaCl_2.2H_2O$, 0.03 g $MnSO_4.H_2O$, 0.51 g/L NaCl, 1 mg/L $FeSO_4.7H_2O$, 1 mg/L $CoCl_2.6H_2O$, 1 mg/L $ZnSO_4.7H_2O$, 0.1 mg/L $CuSO_4.5H_2O$, 0.1 mg/L $H_3BO_4$, 0.1 mg/L $NaMoO_4.2H_2O$ and sufficient $NH_4OH$ to provide a final pH of 6.8. Vitamin $B_{12}$ and spectinomycin were added to the medium to a concentration of 0.1 mg/L and 100 μg/mL, respectively. The honeycomb plate was placed into the Bioscreen C instrument according to the manufacturer's instructions. The plate was incubated at 33° C. with constant shaking and the OD was recorded every 15 min. Growth curve data indicated that most isolates grew at a rate similar to the control strain, PDO3042.

Six independent clones from each strain and the TTab/pSYCO400Agro parent were selected for shake flask analysis. Fresh overnight cultures were inoculated into 12.5 mL MOPS-TM3 medium containing 10 g/L glucose plus 100 ng/mL Vitamin B12 and 100 μg/mL spectinomycin in shake flasks to an initial OD of 0.01. Cells were grown at 33° C. with shaking at 250 rpm for 24 hours. Cultures were centrifuged and the supernatants were added to 0.22 μm Spin-X centrifuge tube filters (Corning Inc., Corning, N.Y.) and centrifuged at 10,000 g for 1 min. The filtrates were analyzed by HPLC using a Waters Alliance 2690 HPLC system with refractive index detection. Samples were injected onto a Shodex SH-1011 column (8 mm×300 mm, purchased from Waters, Milford, Mass.) equipped with a Shodex SH-G guard column (6 mm×50 mm), temperature controlled at 50° C., using 0.01 N $H_2SO_4$ as mobile phase at a flow rate of 0.5 mL/min. Typically, the retention times of PDO and glycerol were 25.4 min and 20.1 min, respectively. The retention time of acetic acid was 22.4 min.

The results of the HPLC analyses are summarized in Table 2. Each value in the table represents the average of six cultures, except for TTab/pSYCO400Agro (Example 3, Comparative), where only one culture was grown. Standard deviations are indicated in parentheses. The results show that strain PDO3042 (Example 4, Comparative) containing the plasmid without acs accumulated similar amount of acetate as the parent TTab/pSYCO400Agro (Example 3, Comparative). Strains PDO3043 (Example 5) and PDO3044 (Example 6) with acs overexpression exhibited about 20% and 40% acetate reduction, respectively, relative to the control, strain PDO3042 (Example 4, Comparative). Furthermore, production of PDO and glycerol was not negatively affected in these acs overexpression strains. Strain PDO3044 (Example 6) with acs expressed by the stronger PT5 promoter showed more acetate reduction, consistent with the higher level of expression (see Example 7).

TABLE 2

Shake flask analysis of PDO production strains with and without acs overexpression

| EXAMPLE | Strain | Final OD550 | PDO (g/L) | Glycerol (g/L) | Acetic acid (mg/L) |
|---|---|---|---|---|---|
| 3, Comparative | TTab/pSYCO400Agro | 3.71 | 2.20 | 3.97 | 89.63 |
| 4, Comparative | PDO3042 | 3.68 (0.07) | 2.24 (0.07) | 4.01 (0.05) | 81.37 (6.19) |
| 5 | PDO3043 | 3.85 (0.05) | 2.26 (0.05) | 3.91 (0.04) | 67.11 (2.46) |
| 6 | PDO3044 | 2.42 (0.12) | 2.75 (0.09) | 4.00 (0.04) | 48.21 (3.63) |

Example 7

Analysis of acs Transcript Levels by Real-Time PCR

This Example demonstrates the increased expression of the acs gene in PDO3043 and PDO3044.

Fresh overnight cultures of strains TTab/pSYCO400Agro, PDO3042, PDO3043 and PDO3044 were inoculated into MOPS-TM3 medium containing 10 g/L glucose plus 100 ng/mL Vitamin B12 and appropriate antibiotics in shake flasks to an initial OD of 0.05. Cells were grown at 33° C. with shaking at 250 rpm for 4-5 hours until the OD reached approximately 0.5. A 2× volume of RNAprotect Bacteria Reagent (Qiagen, Valencia, Calif.) was immediately added to the cultures. The total RNA samples were prepared using RNeasy Mini Kit (Qiagen). Real time, reverse transcriptase (RT)-PCR was performed on an Applied Biosystems 7900 Sequence Detection System instrument using a two-step method (Applied Biosystems, Foster City, Calif.). In step 1, cDNA was synthesized from the provided RNA samples using random hexamers. The samples were first treated with DNase (Qiagen) for 15 min at room temperature, followed by inactivation for 5 min at 75° C. to eliminate any residual genomic DNA. The RNA was then reverse transcribed using the High Capacity cDNA Reverse Transcription Kit (Applied Biosystems) according to the manufacturer's recommended protocol. In step 2, the PCR reaction (20 µL) was run on the ABI 7900 using the following reagents: 10 µL of ABI Taq-Man® Universal PCR Master Mix without UNG (uracil N-glycosylase; PN 4326614), 0.2 µL each of forward and reverse primers (100 µM), 0.05 µL TaqMan® probe (100 µM), 2 µL RNA and 7.55 µL RNase-free water. The PCR primers and dual labeled TaqMan® probes were designed using Primer Express v2.0 software from Applied Biosystems and were purchased from Sigma-Genosys. The primer and probe sequences are shown in Table 3.

TABLE 3

Primer and Probe Sequences Used for Real-Time PCR

| Gene | Primer Name | Direction | Sequence (5' to 3') |
|---|---|---|---|
| 16S rRNA E. coli | 16s-518F | Forward | CCAGCAGCCGCGGTAAT (SEQ ID NO: 70) |
| | 16s-579R | Reverse | TGCGCTTTACGCCCAGT AAT (SEQ ID NO: 71) |
| | 16s-536T | Probe | CGGAGGGTGCAAGCGTT AATCGG (SEQ ID NO: 72) |
| E.coli acs | acs-18F | Forward | ACACACCATTCCTGCCA ACA (SEQ ID NO: 73) |
| | acs-89R | Reverse | TGTTGATACATCGCCTC GTACTG (SEQ ID NO: 74) |
| | acs-39T | Probe | CGCAGACCGTTGCCTGAT AAACCC (SEQ ID NO: 75) |

The following real time PCR thermal cycling conditions were used: 10 min at 95° C. followed by 40 cycles of 95° C. for 15 sec and 60° C. for 1 min. The samples were run at a concentration of 1 ng cDNA/reaction. A (−) reverse transcription RNA control of each sample was run with each primer set to confirm the absence of genomic DNA. All reactions were run in triplicate. The relative quantitation in the samples was calculated using the ΔΔCt method (see Applied Biosystems User Bulletin #2 "Relative Quantitation of Gene Expression", Dec. 11, 1997, updated October 2001). A linear regression was performed for each primer and probe set and the efficiencies were within 95-100%. The 16S rRNA gene was used to normalize the quantitation of the target gene for differences in the amount of total RNA added to each reaction. The results are summarized in Table 4. The relative quantitation (RQ) value is the fold increase in acs expression in the samples relative to the parent strain TTab/pSYCO400Agro. As shown by the data in Table 4, PDO3042 containing the pMTP1.6fucP vector control had about the same acs expression as the control strain, PDO392. PDO3043 containing acs expressed by the Pcat promoter showed about 63-fold increase of acs expression. PDO3044 containing acs expressed by the PT5 promoter showed about 149-fold increase of acs expression

TABLE 4

Relative Expression of acs in PDO Production Strains

| Strain | Relative Quantitation (RQ) |
|---|---|
| PDO392 | 1.00 |
| PDO3044 | 148.7 |
| PDO3043 | 63.15 |
| PDO3042 | 1.21 |

Examples 8-10

Overexpression of Yeast acs Genes in a PDO Production Strain

The yeast acs1 (SEQ ID NO:29) and acs2 (SEQ ID NO:31) genes from *Saccharomyces cerevisiae* were expressed in *E. coli* strain TTab/pSYCO400Agro.

The yeast acs1 or acs2 gene expressed from the Pcat promoter was cloned into pMTP1.6fucP, resulting in pDCQ806 (SEQ ID NO:76) and pDCQ807 (SEQ ID NO:77), respectively. The Pcat-acs1 or the Pcat-acs2 fragment was assembled by overlapping PCR as described below. The first round of PCR was used to amplify the individual element. The Pcat promoter was amplified from QC1549 template (Example 1) using Pcat up primer with Pcat down acs1 or Pcat down acs2 primer. The acs1 or acs2 gene was amplified from yeast genomic DNA using acs1 up with acs1 down primers or acs2 up and acs2 down primers. The second round of PCR was used to assemble the Pcat with the acs1 or acs2 gene. For Pcat-acs1, the Pcat (acs1) and acs1 PCR products from the first round were both added as templates with Pcat up primer and acs1 down primer. For Pcat-acs2, the Pcat (acs2) and acs2 PCR products from the first round were both added as templates with Pcat up primer and acs2 down primer. The PCR products from the second round were purified, and digested with NotI and PmeI. The restricted fragments were ligated with NotI and PmeI digested pMTP1.6fucP. The resulting pDCQ806 and pDCQ807 were confirmed by sequencing. Separate transformations of TTab/pSYCO400Agro with pDCQ806 and pDCQ807 yielded strains PDO3045 and PDO3046, respectively.

The effect of expression of yeast acs1 or acs2 was determined using HPLC analysis, as described in Examples 3-6. The HPLC results are summarized in Table 5. Each value in the table represents the average of six cultures. Standard deviations are indicated in parentheses. Expression of the yeast acs1 gene (strain PDO3045, Example 9) or the acs2 gene (strain PDO3046, Example 10) by the Pcat promoter on pMTP1.6fucP showed about 20% reduction of acetate in the shake flask analysis relative to the strain without the acs gene (strain PDO03042, Example 8, Comparative). Production of PDO and glycerol was not negatively affected in these acs expression strains.

TABLE 5

Shake Flask Analysis of PDO Production Strains Expressing the Yeast acs Genes by the Pcat Promoter

| Example | Strain | Final OD550 | PDO (g/L) | Glycerol (g/L) | Acetic acid (mg/L) |
|---|---|---|---|---|---|
| 8, Comparative | PDO3042 | 3.34 (0.05) | 2.45 (0.10) | 3.87 (0.08) | 76.62 (5.18) |
| 9 | PDO3045 | 3.28 (0.05) | 2.47 (0.05) | 3.89 (0.06) | 63.27 (2.56) |
| 10 | PDO3046 | 3.19 (0.05) | 2.53 (0.08) | 3.86 (0.08) | 60.66 (2.91) |

What is claimed is:

1. A recombinant *Escherichia coli* (*E. coli*) bacterium comprising a promoter operably linked to a nucleotide sequence encoding a polypeptide having acetyl-CoA synthetase enzyme activity, wherein the polypeptide has at least 95% sequence identity to an amino acid sequence selected from the group consisting of SEQ ID NO:28, SEQ ID NO:30, and SEQ ID NO:32, based on the Clustal V method of alignment and is classified as EC 6.2.1.1, wherein the promoter and nucleotide sequence are each independently native or non-native, wherein said recombinant *E. coli* has enhanced acetyl-CoA synthetase enzyme activity compared to a parent *E. coli* from which the recombinant *E. coli* was obtained, and said recombinant *E. coli* produces glycerol, 1,3-propanediol and/or 3-hydroxypropionic acid, and wherein if the promoter and nucleotide sequence are both native, said recombinant *E. coli* comprises at least two copies of the promoter and nucleotide sequence.

2. The recombinant *E. coli* bacterium of claim 1, comprising a non-native promoter and a native nucleotide sequence encoding a polypeptide having acetyl-CoA synthetase enzyme activity.

3. The recombinant *E. coli* bacterium of claim 2, wherein the non-native promoter is a phage T5 promoter or a Pcat promoter.

4. The recombinant *E. coli* bacterium of claim 3, wherein the phage T5 promoter has a nucleotide sequence having at least 95% sequence identity to the nucleotide sequence of SEQ ID NO:33, based on the BLASTN method of alignment.

5. The recombinant *E. coli* bacterium of claim 3, wherein the Pcat promoter has a nucleotide sequence having at least 95% sequence identity to the nucleotide sequence of SEQ ID NO:34, based on the BLASTN method of alignment.

6. A process for making glycerol, 1,3-propanediol, and/or 3-hydroxypropionic acid comprising:
   a) culturing the recombinant *E. coli* bacterium of claim 1 in a suitable growth medium; and
   b) recovering the glycerol, 1,3-propanediol, and/or 3-hydroxypropionic acid produced.

* * * * *

SEQUENCE LISTING

<160> NUMBER OF SEQ ID NOS: 77

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaagat gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110
```

```
Asp Ser Val Lys Asp Val Asp Ile Ile Val Phe Asn Ile Pro His Gln
            115                 120                 125
Phe Leu Pro Arg Ile Cys Ser Gln Leu Lys Gly His Val Asp Ser His
        130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                165                 170                 175
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
        195                 200                 205
Glu Gly Lys Asp Val Asp His Lys Val Leu Lys Ala Leu Phe His Arg
210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
370                 375                 380
Glu Leu Asp Leu His Glu Asp
385                 390

<210> SEQ ID NO 3
<211> LENGTH: 1323
<212> TYPE: DNA
<213> ORGANISM: Saccharomyces cerevisiae

<400> SEQUENCE: 3
atgcttgctg tcagaagatt aacaagatac acattcctta agcgaacgca tccggtgtta      60
tatactcgtc gtgcatataa aattttgcct tcaagatcta ctttcctaag aagatcatta     120
ttacaaacac aactgcactc aaagatgact gctcatacta atatcaaaca gcacaaacac     180
tgtcatgagg accatcctat cagaagatcg gactctgccg tgtcaattgt acatttgaaa     240
cgtgcgccct tcaaggttac agtgattggt tctggtaact ggggaccac catcgccaaa     300 gtcattgcgg aaaacacaga attgcattcc catatcttcg agccagaggt gagaatgtgg     360 gttttttgatg aaaagatcgg cgacgaaaat ctgacggata tcataaatac aagacaccag     420
aacgttaaat atctacccaa tattgacctg ccccataatc tagtggccga tcctgatctt     480
ttacactcca tcaagggtgc tgacatcctt gttttcaaca tccctcatca attttttacca     540
```

-continued

```
aacatagtca aacaattgca aggccacgtg gcccctcatg taagggccat ctcgtgtcta    600
aaagggttcg agttgggctc caagggtgtg caattgctat cctcctatgt tactgatgag    660
ttaggaatcc aatgtggcgc actatctggt gcaaacttgg caccggaagt ggccaaggag    720
cattggtccg aaaccaccgt ggcttaccaa ctaccaaagg attatcaagg tgatggcaag    780
gatgtagatc ataagatttt gaaattgctg ttccacagac cttacttcca cgtcaatgtc    840
atcgatgatg ttgctggtat atccattgcc ggtgccttga agaacgtcgt ggcacttgca    900
tgtggtttcg tagaaggtat gggatggggt aacaatgcct ccgcagccat tcaaaggctg    960
ggtttaggtg aaattatcaa gttcggtaga atgttttttcc cagaatccaa agtcgagacc   1020
tactatcaag aatccgctgg tgttgcagat ctgatcacca cctgctcagg cggtagaaac   1080
gtcaaggttg ccacatacat ggccaagacc ggtaagtcag ccttggaagc agaaaaggaa   1140
ttgcttaacg gtcaatccgc ccaagggata atcacatgca gagaagttca cgagtggcta   1200
caaacatgtg agttgaccca agaattccca ttattcgagg cagtctacca gatagtctac   1260
aacaacgtcc gcatggaaga cctaccggag atgattgaag agctagacat cgatgacgaa   1320
tag                                                                 1323
```

<210> SEQ ID NO 4
<211> LENGTH: 440
<212> TYPE: PRT
<213> ORGANISM: Saccharomyces cerevisiae

<400> SEQUENCE: 4

```
Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240
```

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
            435                 440

<210> SEQ ID NO 5
<211> LENGTH: 816
<212> TYPE: DNA
<213> ORGANISM: Saccharomyces cerevisiae

<400> SEQUENCE: 5
atgaaacgtt tcaatgtttt aaaatatatc agaacaacaa aagcaaatat acaaaccatc      60
gcaatgcctt tgaccacaaa acctttatct ttgaaaatca cgccgctct attcgatgtt     120 gacggtacca tcatcatctc tcaaccagcc attgctgctt tctggagaga tttcggtaaa     180
gacaagcctt acttcgatgc cgaacacgtt attcacatct ctcacggttg agaacttac     240 gatgccattg ccaagttcgc tccagacttt gctgatgaag aatacgttaa caagctagaa     300
ggtgaaatcc agaaaagta cggtgaacac tccatcgaag ttccaggtgc tgtcaagttg     360
tgtaatgctt tgaacgcctt gccaaaggaa aatgggctg tcgccacctc tggtacccgt     420
gacatggcca agaaatggtt cgacattttg aagatcaaga gaccagaata cttcatcacc     480
gccaatgatg tcaagcaagg taagcctcac ccagaaccat acttaaaggg tagaaacggt     540
ttgggtttcc caattaatga acaagaccca tccaaatcta aggttgttgt ctttgaagac     600
gcaccagctg gtattgctgc tggtaaggct gctggctgta aaatcgttgg tattgctacc     660
actttcgatt ggacttctt gaaggaaaag ggttgtgaca tcattgtcaa gaaccacgaa     720
tctatcagag tcggtgaata caacgctgaa accgatgaag tcgaattgat ctttgatgac     780
tacttatacg ctaaggatga cttgttgaaa tggtaa                               816

<210> SEQ ID NO 6
<211> LENGTH: 271
<212> TYPE: PRT

<213> ORGANISM: Saccharomyces cerevisiae

<400> SEQUENCE: 6

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65              70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145             150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225             230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
            260                 265                 270
```

<210> SEQ ID NO 7
<211> LENGTH: 753
<212> TYPE: DNA
<213> ORGANISM: Saccharomyces cerevisiae

<400> SEQUENCE: 7

```
atgggattga ctactaaacc tctatctttg aaagttaacg ccgctttgtt cgacgtcgac    60
ggtaccatta tcatctctca accagccatt gctgcattct ggagggattt cggtaaggac   120
aaaccttatt tcgatgctga acacgttatc caagtctcgc atggttggag aacgtttgat   180
gccattgcta agttcgctcc agactttgcc aatgaagagt atgttaacaa attagaagct   240
gaaattccgg tcaagtacgg tgaaaaatcc attgaagtcc aggtgcagt taagctgtgc   300 aacgctttga cgctctacc aaaagagaaa tgggctgtgg caacttccgg tacccgtgat   360
atggcacaaa atggttcga gcatctggga atcaggagac caaagtactt cattaccgct   420
aatgatgtca acagggtaa gcctcatcca gaaccatatc tgaagggcag gaatggctta   480
ggatatccga tcaatgagca agacccttcc aaatctaagg tagtagtatt tgaagacgct   540
```

```
ccagcaggta ttgccgccgg aaaagccgcc ggttgtaaga tcattggtat tgccactact    600
ttcgacttgg acttcctaaa ggaaaaaggc tgtgacatca ttgtcaaaaa ccacgaatcc    660
atcagagttg gcggctacaa tgccgaaaca gacgaagttg aattcatttt tgacgactac    720
ttatatgcta aggacgatct gttgaaatgg taa                                 753
```

<210> SEQ ID NO 8
<211> LENGTH: 250
<212> TYPE: PRT
<213> ORGANISM: Saccharomyces cerevisiae

<400> SEQUENCE: 8

```
Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250
```

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9

```
atg aaa aga tca aaa cga ttt gca gta ctg gcc cag cgc ccc gtc aat    48
Met Lys Arg Ser Lys Arg Phe Ala Val Leu Ala Gln Arg Pro Val Asn
1               5                   10                  15
```

```
cag gac ggg ctg att ggc gag tgg cct gaa gag ggg ctg atc gcc atg      96
Gln Asp Gly Leu Ile Gly Glu Trp Pro Glu Glu Gly Leu Ile Ala Met
         20                  25                  30 gac agc ccc ttt gac ccg gtc tct tca gta aaa gtg gac aac ggt ctg     144
Asp Ser Pro Phe Asp Pro Val Ser Ser Val Lys Val Asp Asn Gly Leu
             35                  40                  45 atc gtc gaa ctg gac ggc aaa cgc cgg gac cag ttt gac atg atc gac     192
Ile Val Glu Leu Asp Gly Lys Arg Arg Asp Gln Phe Asp Met Ile Asp
 50                  55                  60 cga ttt atc gcc gat tac gcg atc aac gtt gag cgc aca gag cag gca     240
Arg Phe Ile Ala Asp Tyr Ala Ile Asn Val Glu Arg Thr Glu Gln Ala
 65                  70                  75                  80 atg cgc ctg gag gcg gtg gaa ata gcc cgt atg ctg gtg gat att cac     288
Met Arg Leu Glu Ala Val Glu Ile Ala Arg Met Leu Val Asp Ile His
                 85                  90                  95 gtc agc cgg gag gag atc att gcc atc act acc gcc atc acg ccg gcc     336
Val Ser Arg Glu Glu Ile Ile Ala Ile Thr Thr Ala Ile Thr Pro Ala
            100                 105                 110 aaa gcg gtc gag gtg atg gcg cag atg aac gtg gtg gag atg atg atg     384
Lys Ala Val Glu Val Met Ala Gln Met Asn Val Val Glu Met Met Met
        115                 120                 125 gcg ctg cag aag atg cgt gcc cgc cgg acc ccc tcc aac cag tgc cac     432
Ala Leu Gln Lys Met Arg Ala Arg Arg Thr Pro Ser Asn Gln Cys His
130                 135                 140 gtc acc aat ctc aaa gat aat ccg gtg cag att gcc gct gac gcc gcc     480
Val Thr Asn Leu Lys Asp Asn Pro Val Gln Ile Ala Ala Asp Ala Ala
145                 150                 155                 160 gag gcc ggg atc cgc ggc ttc tca gaa cag gag acc acg gtc ggt atc     528
Glu Ala Gly Ile Arg Gly Phe Ser Glu Gln Glu Thr Thr Val Gly Ile
                165                 170                 175 gcg cgc tac gcg ccg ttt aac gcc ctg gcg ctg ttg gtc ggt tcg cag     576
Ala Arg Tyr Ala Pro Phe Asn Ala Leu Ala Leu Leu Val Gly Ser Gln
            180                 185                 190 tgc ggc cgc ccc ggc gtg ttg acg cag tgc tcg gtg gaa gag gcc acc     624
Cys Gly Arg Pro Gly Val Leu Thr Gln Cys Ser Val Glu Glu Ala Thr
        195                 200                 205 gag ctg gag ctg ggc atg cgt ggc tta acc agc tac gcc gag acg gtg     672
Glu Leu Glu Leu Gly Met Arg Gly Leu Thr Ser Tyr Ala Glu Thr Val
210                 215                 220 tcg gtc tac ggc acc gaa gcg gta ttt acc gac ggc gat gat acg ccg     720
Ser Val Tyr Gly Thr Glu Ala Val Phe Thr Asp Gly Asp Asp Thr Pro
225                 230                 235                 240 tgg tca aag gcg ttc ctc gcc tcg gcc tac gcc tcc cgc ggg ttg aaa     768
Trp Ser Lys Ala Phe Leu Ala Ser Ala Tyr Ala Ser Arg Gly Leu Lys
                245                 250                 255 atg cgc tac acc tcc ggc acc gga tcc gaa gcg ctg atg ggc tat tcg     816
Met Arg Tyr Thr Ser Gly Thr Gly Ser Glu Ala Leu Met Gly Tyr Ser
            260                 265                 270 gag agc aag tcg atg ctc tac ctc gaa tcg cgc tgc atc ttc att act     864
Glu Ser Lys Ser Met Leu Tyr Leu Glu Ser Arg Cys Ile Phe Ile Thr
        275                 280                 285 aaa ggc gcc ggg gtt cag gga ctg caa aac ggc gcg gtg agc tgt atc     912
Lys Gly Ala Gly Val Gln Gly Leu Gln Asn Gly Ala Val Ser Cys Ile
290                 295                 300 ggc atg acc ggc gct gtg ccg tcg ggc att cgg gcg gtg ctg gcg gaa     960
Gly Met Thr Gly Ala Val Pro Ser Gly Ile Arg Ala Val Leu Ala Glu
305                 310                 315                 320 aac ctg atc gcc tct atg ctc gac ctc gaa gtg gcg tcc gcc aac gac    1008
Asn Leu Ile Ala Ser Met Leu Asp Leu Glu Val Ala Ser Ala Asn Asp
                325                 330                 335
```

```
cag act ttc tcc cac tcg gat att cgc cgc acc gcg cgc acc ctg atg      1056
Gln Thr Phe Ser His Ser Asp Ile Arg Arg Thr Ala Arg Thr Leu Met
            340                 345                 350 cag atg ctg ccg ggc acc gac ttt att ttc tcc ggc tac agc gcg gtg      1104
Gln Met Leu Pro Gly Thr Asp Phe Ile Phe Ser Gly Tyr Ser Ala Val
        355                 360                 365 ccg aac tac gac aac atg ttc gcc ggc tcg aac ttc gat gcg gaa gat      1152
Pro Asn Tyr Asp Asn Met Phe Ala Gly Ser Asn Phe Asp Ala Glu Asp
    370                 375                 380 ttt gat gat tac aac atc ctg cag cgt gac ctg atg gtt gac ggc ggc      1200
Phe Asp Asp Tyr Asn Ile Leu Gln Arg Asp Leu Met Val Asp Gly Gly
385                 390                 395                 400 ctg cgt ccg gtg acc gag gcg gaa acc att gcc att cgc cag aaa gcg      1248
Leu Arg Pro Val Thr Glu Ala Glu Thr Ile Ala Ile Arg Gln Lys Ala
                405                 410                 415 gcg cgg gcg atc cag gcg gtt ttc cgc gag ctg ggg ctg ccg cca atc      1296
Ala Arg Ala Ile Gln Ala Val Phe Arg Glu Leu Gly Leu Pro Pro Ile
            420                 425                 430 gcc gac gag gag gtg gag gcc gcc acc tac gcg cac ggc agc aac gag      1344
Ala Asp Glu Glu Val Glu Ala Ala Thr Tyr Ala His Gly Ser Asn Glu
        435                 440                 445 atg ccg ccg cgt aac gtg gtg gag gat ctg agt gcg gtg gaa gag atg      1392
Met Pro Pro Arg Asn Val Val Glu Asp Leu Ser Ala Val Glu Glu Met
    450                 455                 460 atg aag cgc aac atc acc ggc ctc gat att gtc ggc gcg ctg agc cgc      1440
Met Lys Arg Asn Ile Thr Gly Leu Asp Ile Val Gly Ala Leu Ser Arg
465                 470                 475                 480 agc ggc ttt gag gat atc gcc agc aat att ctc aat atg ctg cgc cag      1488
Ser Gly Phe Glu Asp Ile Ala Ser Asn Ile Leu Asn Met Leu Arg Gln
                485                 490                 495 cgg gtc acc ggc gat tac ctg cag acc tcg gcc att ctc gat cgg cag      1536
Arg Val Thr Gly Asp Tyr Leu Gln Thr Ser Ala Ile Leu Asp Arg Gln
            500                 505                 510 ttc gag gtg gtg agt gcg gtc aac gac atc aat gac tat cag ggg ccg      1584
Phe Glu Val Val Ser Ala Val Asn Asp Ile Asn Asp Tyr Gln Gly Pro
        515                 520                 525 ggc acc ggc tat cgc atc tct gcc gaa cgc tgg gcg gag atc aaa aat      1632
Gly Thr Gly Tyr Arg Ile Ser Ala Glu Arg Trp Ala Glu Ile Lys Asn
    530                 535                 540 att ccg ggc gtg gtt cag ccc gac acc att gaa taa                      1668
Ile Pro Gly Val Val Gln Pro Asp Thr Ile Glu
545                 550                 555

<210> SEQ ID NO 10
<211> LENGTH: 555
<212> TYPE: PRT
<213> ORGANISM: Klebsiella pneumoniae

<400> SEQUENCE: 10

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
```

```
                    85                  90                  95
Val Ser Arg Glu Glu Ile Ile Ala Ile Thr Thr Ala Ile Thr Pro Ala
                100                 105                 110

Lys Ala Val Glu Val Met Ala Gln Met Asn Val Val Glu Met Met Met
            115                 120                 125

Ala Leu Gln Lys Met Arg Ala Arg Arg Thr Pro Ser Asn Gln Cys His
        130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Thr Thr Val Gly Ile
                165                 170                 175

Ala Arg Tyr Ala Pro Phe Asn Ala Leu Ala Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510
```

```
Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc     48
Val Gln Gln Thr Thr Gln Ile Gln Pro Ser Phe Thr Leu Lys Thr Arg
 1               5                  10                  15 gag ggc ggg gta gct tct gcc gat gaa cgc gcc gat gaa gtg gtg atc     96
Glu Gly Gly Val Ala Ser Ala Asp Glu Arg Ala Asp Glu Val Val Ile
             20                  25                  30 ggc gtc ggc cct gcc ttc gat aaa cac cag cat cac act ctg atc gat    144
Gly Val Gly Pro Ala Phe Asp Lys His Gln His His Thr Leu Ile Asp
         35                  40                  45 atg ccc cat ggc gcg atc ctc aaa gag ctg att gcc ggg gtg gaa gaa    192
Met Pro His Gly Ala Ile Leu Lys Glu Leu Ile Ala Gly Val Glu Glu
     50                  55                  60 gag ggg ctt cac gcc cgg gtg gtg cgc att ctg cgc acg tcc gac gtc    240
Glu Gly Leu His Ala Arg Val Val Arg Ile Leu Arg Thr Ser Asp Val
 65                  70                  75                  80 tcc ttt atg gcc tgg gat gcg gcc aac ctg agc ggc tcg ggg atc ggc    288
Ser Phe Met Ala Trp Asp Ala Ala Asn Leu Ser Gly Ser Gly Ile Gly
                 85                  90                  95 atc ggt atc cag tcg aag ggg acc acg gtc atc cat cag cgc gat ctg    336
Ile Gly Ile Gln Ser Lys Gly Thr Thr Val Ile His Gln Arg Asp Leu
            100                 105                 110 ctg ccg ctc agc aac ctg gag ctg ttc tcc cag gcg ccg ctg ctg acg    384
Leu Pro Leu Ser Asn Leu Glu Leu Phe Ser Gln Ala Pro Leu Leu Thr
        115                 120                 125 ctg gag acc tac cgg cag att ggc aaa aac gct gcg cgc tat gcg cgc    432
Leu Glu Thr Tyr Arg Gln Ile Gly Lys Asn Ala Ala Arg Tyr Ala Arg
    130                 135                 140 aaa gag tca cct tcg ccg gtg ccg gtg gtg aac gat cag atg gtg cgg    480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa    528
Pro Lys Phe Met Ala Lys Ala Ala Leu Phe His Ile Lys Glu Thr Lys
                165                 170                 175 cat gtg gtg cag gac gcc gag ccc gtc acc ctg cac atc gac tta gta    576
His Val Val Gln Asp Ala Glu Pro Val Thr Leu His Ile Asp Leu Val
            180                 185                 190 agg gag tga                                                        585
Arg Glu

<210> SEQ ID NO 12
<211> LENGTH: 194
<212> TYPE: PRT
<213> ORGANISM: Klebsiella pneumoniae

<400> SEQUENCE: 12

Val Gln Gln Thr Thr Gln Ile Gln Pro Ser Phe Thr Leu Lys Thr Arg
```

```
                 1               5                  10                 15
Glu Gly Gly Val Ala Ser Ala Asp Glu Arg Ala Asp Glu Val Val Ile
                20                  25                  30

Gly Val Gly Pro Ala Phe Asp Lys His Gln His His Thr Leu Ile Asp
                35                  40                  45

Met Pro His Gly Ala Ile Leu Lys Glu Leu Ile Ala Gly Val Glu Glu
 50                  55                  60

Glu Gly Leu His Ala Arg Val Val Arg Ile Leu Arg Thr Ser Asp Val
 65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
                100                 105                 110

Leu Pro Leu Ser Asn Leu Glu Leu Phe Ser Gln Ala Pro Leu Leu Thr
                115                 120                 125

Leu Glu Thr Tyr Arg Gln Ile Gly Lys Asn Ala Ala Arg Tyr Ala Arg
                130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
                180                 185                 190

Arg Glu

<210> SEQ ID NO 13
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

<400> SEQUENCE: 13 atg agc gag aaa acc atg cgc gtg cag gat tat ccg tta gcc acc cgc       48
Met Ser Glu Lys Thr Met Arg Val Gln Asp Tyr Pro Leu Ala Thr Arg
 1               5                  10                  15 tgc ccg gag cat atc ctg acg cct acc ggc aaa cca ttg acc gat att       96
Cys Pro Glu His Ile Leu Thr Pro Thr Gly Lys Pro Leu Thr Asp Ile
                20                  25                  30 acc ctc gag aag gtg ctc tct ggc gag gtg ggc ccg cag gat gtg cgg      144
Thr Leu Glu Lys Val Leu Ser Gly Glu Val Gly Pro Gln Asp Val Arg
            35                  40                  45 atc tcc cgc cag acc ctt gag tac cag gcg cag att gcc gag cag atg      192
Ile Ser Arg Gln Thr Leu Glu Tyr Gln Ala Gln Ile Ala Glu Gln Met
 50                  55                  60 cag cgc cat gcg gtg gcg cgc aat ttc cgc cgc gcg gcg gag ctt atc      240
Gln Arg His Ala Val Ala Arg Asn Phe Arg Arg Ala Ala Glu Leu Ile
 65                  70                  75                  80 gcc att cct gac gag cgc att ctg gct atc tat aac gcg ctg cgc ccg      288
Ala Ile Pro Asp Glu Arg Ile Leu Ala Ile Tyr Asn Ala Leu Arg Pro
                85                  90                  95 ttc cgc tcc tcg cag gcg gag ctg ctg gcg atc gcc gac gag ctg gag      336
Phe Arg Ser Ser Gln Ala Glu Leu Leu Ala Ile Ala Asp Glu Leu Glu
                100                 105                 110 cac acc tgg cat gcg aca gtg aat gcc gcc ttt gtc cgg gag tcg gcg      384
His Thr Trp His Ala Thr Val Asn Ala Ala Phe Val Arg Glu Ser Ala
                115                 120                 125
```

```
gaa gtg tat cag cag cgg cat aag ctg cgt aaa gga agc taa            426
Glu Val Tyr Gln Gln Arg His Lys Leu Arg Lys Gly Ser
    130                 135                 140
```

<210> SEQ ID NO 14
<211> LENGTH: 141
<212> TYPE: PRT
<213> ORGANISM: Klebsiella pneumoniae

<400> SEQUENCE: 14

```
Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140
```

<210> SEQ ID NO 15
<211> LENGTH: 1539
<212> TYPE: DNA
<213> ORGANISM: Escherichia coli
<220> FEATURE:
<221> NAME/KEY: CDS
<222> LOCATION: (1)..(1539)

<400> SEQUENCE: 15

```
atg acc aat aat ccc cct tca gca cag att aag ccc ggc gag tat ggt    48
Met Thr Asn Asn Pro Pro Ser Ala Gln Ile Lys Pro Gly Glu Tyr Gly
1               5                   10                  15 ttc ccc ctc aag tta aaa gcc cgc tat gac aac ttt att ggc ggc gaa    96
Phe Pro Leu Lys Leu Lys Ala Arg Tyr Asp Asn Phe Ile Gly Gly Glu
            20                  25                  30 tgg gta gcc cct gcc gac ggc gag tat tac cag aat ctg acg ccg gtg   144
Trp Val Ala Pro Ala Asp Gly Glu Tyr Tyr Gln Asn Leu Thr Pro Val
        35                  40                  45 acc ggg cag ctg ctg tgc gaa gtg gcg tct tcg ggc aaa cga gac atc   192
Thr Gly Gln Leu Leu Cys Glu Val Ala Ser Ser Gly Lys Arg Asp Ile
    50                  55                  60 gat ctg gcg ctg gat gct gcg cac aaa gtg aaa gat aaa tgg gcg cac   240
Asp Leu Ala Leu Asp Ala Ala His Lys Val Lys Asp Lys Trp Ala His
65                  70                  75                  80 acc tcg gtg cag gat cgt gcg gcg att ctg ttt aag att gcc gat cga   288
Thr Ser Val Gln Asp Arg Ala Ala Ile Leu Phe Lys Ile Ala Asp Arg
                85                  90                  95 atg gaa caa aac ctc gag ctg tta gcg aca gct gaa acc tgg gat aac   336
Met Glu Gln Asn Leu Glu Leu Leu Ala Thr Ala Glu Thr Trp Asp Asn
            100                 105                 110 ggc aaa ccc att cgc gaa acc agt gct gcg gat gta ccg ctg gcg att   384
Gly Lys Pro Ile Arg Glu Thr Ser Ala Ala Asp Val Pro Leu Ala Ile
```

-continued

```
                115                 120                 125
gac cat ttc cgc tat ttc gcc tcg tgt att cgg gcg cag gaa ggt ggg      432
Asp His Phe Arg Tyr Phe Ala Ser Cys Ile Arg Ala Gln Glu Gly Gly
    130                 135                 140 atc agt gaa gtt gat agc gaa acc gtg gcc tat cat ttc cat gaa ccg      480
Ile Ser Glu Val Asp Ser Glu Thr Val Ala Tyr His Phe His Glu Pro
145                 150                 155                 160 tta ggc gtg gtg ggg cag att atc ccg tgg aac ttc ccg ctg ctg atg      528
Leu Gly Val Val Gly Gln Ile Ile Pro Trp Asn Phe Pro Leu Leu Met
                165                 170                 175 gcg agc tgg aaa atg gct ccc gcg ctg gcg gcg ggc aac tgt gtg gtg      576
Ala Ser Trp Lys Met Ala Pro Ala Leu Ala Ala Gly Asn Cys Val Val
            180                 185                 190 ctg aaa ccc gca cgt ctt acc ccg ctt tct gta ctg cta atg gaa          624
Leu Lys Pro Ala Arg Leu Thr Pro Leu Ser Val Leu Leu Met Glu
        195                 200                 205 att gtc ggt gat tta ctg ccg ccg ggc gtg gtg aac gtg gtc aat ggc      672
Ile Val Gly Asp Leu Leu Pro Pro Gly Val Val Asn Val Val Asn Gly
    210                 215                 220 gca ggt ggg gta att ggc gaa tat ctg gcg acc tcg aaa cgc atc gcc      720
Ala Gly Gly Val Ile Gly Glu Tyr Leu Ala Thr Ser Lys Arg Ile Ala
225                 230                 235                 240 aaa gtg gcg ttt acc ggc tca acg gaa gtg ggc caa caa att atg caa      768
Lys Val Ala Phe Thr Gly Ser Thr Glu Val Gly Gln Gln Ile Met Gln
                245                 250                 255 tac gca acg caa aac att att ccg gtg acg ctg gag ttg ggc ggt aag      816
Tyr Ala Thr Gln Asn Ile Ile Pro Val Thr Leu Glu Leu Gly Gly Lys
            260                 265                 270 tcg cca aat atc ttc ttt gct gat gtg atg gat gaa gaa gat gcc ttt      864
Ser Pro Asn Ile Phe Phe Ala Asp Val Met Asp Glu Glu Asp Ala Phe
        275                 280                 285 ttc gat aaa gcg ctg gaa ggc ttt gca ctg ttt gcc ttt aac cag ggc      912
Phe Asp Lys Ala Leu Glu Gly Phe Ala Leu Phe Ala Phe Asn Gln Gly
    290                 295                 300 gaa gtt tgc acc tgt ccg agt cgt gct tta gtg cag gaa tct atc tac      960
Glu Val Cys Thr Cys Pro Ser Arg Ala Leu Val Gln Glu Ser Ile Tyr
305                 310                 315                 320 gaa cgc ttt atg gaa cgc gcc atc cgc cgt gtc gaa agc att cgt agc     1008
Glu Arg Phe Met Glu Arg Ala Ile Arg Arg Val Glu Ser Ile Arg Ser
                325                 330                 335 ggt aac ccg ctc gac agc gtg acg caa atg ggc gcg cag gtt tct cac     1056
Gly Asn Pro Leu Asp Ser Val Thr Gln Met Gly Ala Gln Val Ser His
            340                 345                 350 ggg caa ctg gaa acc atc ctc aac tac att gat atc ggt aaa aaa gag     1104
Gly Gln Leu Glu Thr Ile Leu Asn Tyr Ile Asp Ile Gly Lys Lys Glu
        355                 360                 365 ggc gct gac gtg ctc aca ggc ggg cgg cgc aag ctg ctg gaa ggt gaa     1152
Gly Ala Asp Val Leu Thr Gly Gly Arg Arg Lys Leu Leu Glu Gly Glu
    370                 375                 380 ctg aaa gac ggc tac tac ctc gaa ccg acg att ctg ttt ggt cag aac     1200
Leu Lys Asp Gly Tyr Tyr Leu Glu Pro Thr Ile Leu Phe Gly Gln Asn
385                 390                 395                 400 aat atg cgg gtg ttc cag gag gag att ttt ggc ccg gtg ctg gcg gtg     1248
Asn Met Arg Val Phe Gln Glu Glu Ile Phe Gly Pro Val Leu Ala Val
                405                 410                 415 acc acc ttc aaa acg atg gaa gaa gcg ctg gag ctg gcg aac gat acg     1296
Thr Thr Phe Lys Thr Met Glu Glu Ala Leu Glu Leu Ala Asn Asp Thr
            420                 425                 430 caa tat ggc ctg ggc gcg ggc gtc tgg agc cgc aac ggt aat ctg gcc     1344
Gln Tyr Gly Leu Gly Ala Gly Val Trp Ser Arg Asn Gly Asn Leu Ala
```

```
                        435                    440                      445
tat aag atg ggg cgc ggc ata cag gct ggg cgc gtg tgg acc aac tgt                      1392
Tyr Lys Met Gly Arg Gly Ile Gln Ala Gly Arg Val Trp Thr Asn Cys
    450                     455                     460 tat cac gct tac ccg gca cat gcg gcg ttt ggt ggc tac aaa caa tca                      1440
Tyr His Ala Tyr Pro Ala His Ala Ala Phe Gly Gly Tyr Lys Gln Ser
465                     470                     475                 480 ggt atc ggt cgc gaa acc cac aag atg atg ctg gag cat tac cag caa                      1488
Gly Ile Gly Arg Glu Thr His Lys Met Met Leu Glu His Tyr Gln Gln
                485                     490                     495 acc aag tgc ctg ctg gtg agc tac tcg gat aaa ccg ttg ggg ctg ttc                      1536
Thr Lys Cys Leu Leu Val Ser Tyr Ser Asp Lys Pro Leu Gly Leu Phe
            500                     505                     510 tga                                                                                   1539

<210> SEQ ID NO 16
<211> LENGTH: 512
<212> TYPE: PRT
<213> ORGANISM: Escherichia coli

<400> SEQUENCE: 16

Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
    50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
```

```
                      275                 280                 285
Phe Asp Lys Ala Leu Glu Gly Phe Ala Leu Phe Ala Phe Asn Gln Gly
    290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
    370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
    450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
            500                 505                 510

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17 atg tca gta ccc gtt caa cat cct atg tat atc gat gga cag ttt gtt      48
Met Ser Val Pro Val Gln His Pro Met Tyr Ile Asp Gly Gln Phe Val
1               5                   10                  15 acc tgg cgt gga gac gca tgg att gat gtg gta aac cct gct aca gag      96
Thr Trp Arg Gly Asp Ala Trp Ile Asp Val Val Asn Pro Ala Thr Glu
            20                  25                  30 gct gtc att tcc cgc ata ccc gat ggt cag gcc gag gat gcc cgt aag     144
Ala Val Ile Ser Arg Ile Pro Asp Gly Gln Ala Glu Asp Ala Arg Lys
        35                  40                  45 gca atc gat gca gca gaa cgt gca caa cca gaa tgg gaa gcg ttg cct     192
Ala Ile Asp Ala Ala Glu Arg Ala Gln Pro Glu Trp Glu Ala Leu Pro
    50                  55                  60 gct att gaa cgc gcc agt tgg ttg cgc aaa atc tcc gcc ggg atc cgc     240
Ala Ile Glu Arg Ala Ser Trp Leu Arg Lys Ile Ser Ala Gly Ile Arg
65                  70                  75                  80 gaa cgc gcc agt gaa atc agt gcg ctg att gtt gaa gaa ggg ggc aag     288
Glu Arg Ala Ser Glu Ile Ser Ala Leu Ile Val Glu Glu Gly Gly Lys
                85                  90                  95 atc cag cag ctg gct gaa gtc gaa gtg gct ttt act gcc gac tat atc     336
Ile Gln Gln Leu Ala Glu Val Glu Val Ala Phe Thr Ala Asp Tyr Ile
```

```
                Ile Gln Gln Leu Ala Glu Val Glu Val Ala Phe Thr Ala Asp Tyr Ile
                                100                 105                 110 gat tac atg gcg gag tgg gca cgg cgt tac gag ggc gag att att caa        384
Asp Tyr Met Ala Glu Trp Ala Arg Arg Tyr Glu Gly Glu Ile Ile Gln
            115                 120                 125 agc gat cgt cca gga gaa aat att ctt ttg ttt aaa cgt gcg ctt ggt        432
Ser Asp Arg Pro Gly Glu Asn Ile Leu Leu Phe Lys Arg Ala Leu Gly
        130                 135                 140 gtg act acc ggc att ctg ccg tgg aac ttc ccg ttc ttc ctc att gcc        480
Val Thr Thr Gly Ile Leu Pro Trp Asn Phe Pro Phe Phe Leu Ile Ala
145                 150                 155                 160 cgc aaa atg gct ccc gct ctt ttg acc ggt aat acc atc gtc att aaa        528
Arg Lys Met Ala Pro Ala Leu Leu Thr Gly Asn Thr Ile Val Ile Lys
                165                 170                 175 cct agt gaa ttt acg cca aac aat gcg att gca ttc gcc aaa atc gtc        576
Pro Ser Glu Phe Thr Pro Asn Asn Ala Ile Ala Phe Ala Lys Ile Val
            180                 185                 190 gat gaa ata ggc ctt ccg cgc ggc gtg ttt aac ctt gta ctg ggg cgt        624
Asp Glu Ile Gly Leu Pro Arg Gly Val Phe Asn Leu Val Leu Gly Arg
        195                 200                 205 ggt gaa acc gtt ggg caa gaa ctg gcg ggt aac cca aag gtc gca atg        672
Gly Glu Thr Val Gly Gln Glu Leu Ala Gly Asn Pro Lys Val Ala Met
210                 215                 220 gtc agt atg aca ggc agc gtc tct gca ggt gag aag atc atg gcg act        720
Val Ser Met Thr Gly Ser Val Ser Ala Gly Glu Lys Ile Met Ala Thr
225                 230                 235                 240 gcg gcg aaa aac atc acc aaa gtg tgt ctg gaa ttg ggg ggt aaa gca        768
Ala Ala Lys Asn Ile Thr Lys Val Cys Leu Glu Leu Gly Gly Lys Ala
                245                 250                 255 cca gct atc gta atg gac gat gcc gat ctt gaa ctg gca gtc aaa gcc        816
Pro Ala Ile Val Met Asp Asp Ala Asp Leu Glu Leu Ala Val Lys Ala
            260                 265                 270 atc gtt gat tca cgc gtc att aat agt ggg caa gtg tgt aac tgt gca        864
Ile Val Asp Ser Arg Val Ile Asn Ser Gly Gln Val Cys Asn Cys Ala
        275                 280                 285 gaa cgt gtt tat gta cag aaa ggc att tat gat cag ttc gtc aat cgg        912
Glu Arg Val Tyr Val Gln Lys Gly Ile Tyr Asp Gln Phe Val Asn Arg
290                 295                 300 ctg ggt gaa gcg atg cag gcg gtt caa ttt ggt aac ccc gct gaa cgc        960
Leu Gly Glu Ala Met Gln Ala Val Gln Phe Gly Asn Pro Ala Glu Arg
305                 310                 315                 320 aac gac att gcg atg ggg ccg ttg att aac gcc gcg gcg ctg gaa agg       1008
Asn Asp Ile Ala Met Gly Pro Leu Ile Asn Ala Ala Ala Leu Glu Arg
                325                 330                 335 gtc gag caa aaa gtg gcg cgc gca gta gaa gaa ggg gcg aga gtg gcg       1056
Val Glu Gln Lys Val Ala Arg Ala Val Glu Glu Gly Ala Arg Val Ala
            340                 345                 350 ttc ggt ggc aaa gcg gta gag ggg aaa gga tat tat tat ccg ccg aca       1104
Phe Gly Gly Lys Ala Val Glu Gly Lys Gly Tyr Tyr Tyr Pro Pro Thr
        355                 360                 365 ttg ctg ctg gat gtt cgc cag gaa atg tcg att atg cat gag gaa acc       1152
Leu Leu Leu Asp Val Arg Gln Glu Met Ser Ile Met His Glu Glu Thr
370                 375                 380 ttt ggc ccg gtg ctg cca gtt gtc gca ttt gac acg ctg gaa gat gct       1200
Phe Gly Pro Val Leu Pro Val Val Ala Phe Asp Thr Leu Glu Asp Ala
385                 390                 395                 400 atc tca atg gct aat gac agt gat tac ggc ctg acc tca tca atc tat       1248
Ile Ser Met Ala Asn Asp Ser Asp Tyr Gly Leu Thr Ser Ser Ile Tyr
                405                 410                 415 acc caa aat ctg aac gtc gcg atg aaa gcc att aaa ggg ctg aag ttt       1296
```

```
Thr Gln Asn Leu Asn Val Ala Met Lys Ala Ile Lys Gly Leu Lys Phe
            420                 425                 430 ggt gaa act tac atc aac cgt gaa aac ttc gaa gct atg caa ggc ttc    1344
Gly Glu Thr Tyr Ile Asn Arg Glu Asn Phe Glu Ala Met Gln Gly Phe
            435                 440                 445 cac gcc gga tgg cgt aaa tcc ggt att ggc ggc gca gat ggt aaa cat    1392
His Ala Gly Trp Arg Lys Ser Gly Ile Gly Gly Ala Asp Gly Lys His
        450                 455                 460 ggc ttg cat gaa tat ctg cag acc cag gtg gtt tat tta cag tct taa    1440
Gly Leu His Glu Tyr Leu Gln Thr Gln Val Val Tyr Leu Gln Ser
465                 470                 475
```

<210> SEQ ID NO 18
<211> LENGTH: 479
<212> TYPE: PRT
<213> ORGANISM: Escherichia coli

<400> SEQUENCE: 18

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300
```

-continued

```
Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
            325                 330                 335

Val Glu Gln Lys Val Ala Arg Ala Val Glu Glu Gly Ala Arg Val Ala
        340                 345                 350

Phe Gly Gly Lys Ala Val Glu Gly Lys Gly Tyr Tyr Tyr Pro Pro Thr
    355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475

<210> SEQ ID NO 19
<211> LENGTH: 1488
<212> TYPE: DNA
<213> ORGANISM: Escherichia coli
<220> FEATURE:
<221> NAME/KEY: CDS
<222> LOCATION: (1)..(1488)

<400> SEQUENCE: 19 atg aat ttt cat cat ctg gct tac tgg cag gat aaa gcg tta agt ctc      48
Met Asn Phe His His Leu Ala Tyr Trp Gln Asp Lys Ala Leu Ser Leu
1               5                   10                  15 gcc att gaa aac cgc tta ttt att aac ggt gaa tat act gct gcg gcg      96
Ala Ile Glu Asn Arg Leu Phe Ile Asn Gly Glu Tyr Thr Ala Ala Ala
            20                  25                  30 gaa aat gaa acc ttt gaa acc gtt gat ccg gtc acc cag gca ccg ctg     144
Glu Asn Glu Thr Phe Glu Thr Val Asp Pro Val Thr Gln Ala Pro Leu
        35                  40                  45 gcg aaa att gcc cgc ggc aag agc gtc gat atc gac cgt gcg atg agc     192
Ala Lys Ile Ala Arg Gly Lys Ser Val Asp Ile Asp Arg Ala Met Ser
    50                  55                  60 gca gca cgc ggc gta ttt gaa cgc ggc gac tgg tca ctc tct tct ccg     240
Ala Ala Arg Gly Val Phe Glu Arg Gly Asp Trp Ser Leu Ser Ser Pro
65                  70                  75                  80 gct aaa cgt aaa gcg gta ctg aat aaa ctc gcc gat tta atg gaa gcc     288
Ala Lys Arg Lys Ala Val Leu Asn Lys Leu Ala Asp Leu Met Glu Ala
                85                  90                  95 cac gcc gaa gag ctg gca ctg ctg gaa act ctc gac acc ggc aaa ccg     336
His Ala Glu Glu Leu Ala Leu Leu Glu Thr Leu Asp Thr Gly Lys Pro
            100                 105                 110 att cgt cac agt ctg cgt gat gat att ccc ggc gcg gcg cgc gcc att     384
Ile Arg His Ser Leu Arg Asp Asp Ile Pro Gly Ala Ala Arg Ala Ile
        115                 120                 125 cgc tgg tac gcc gaa gcg atc gac aaa gtg tat ggc gaa gtg gcg acc     432
Arg Trp Tyr Ala Glu Ala Ile Asp Lys Val Tyr Gly Glu Val Ala Thr
    130                 135                 140
```

```
acc agt agc cat gag ctg gcg atg atc gtg cgt gaa ccg gtc ggc gtg     480
Thr Ser Ser His Glu Leu Ala Met Ile Val Arg Glu Pro Val Gly Val
145                 150                 155                 160 att gcc gcc atc gtg ccg tgg aac ttc ccg ctg ttg ctg act tgc tgg     528
Ile Ala Ala Ile Val Pro Trp Asn Phe Pro Leu Leu Leu Thr Cys Trp
                165                 170                 175 aaa ctc ggc ccg gcg ctg gcg gcg gga aac agc gtg att cta aaa ccg     576
Lys Leu Gly Pro Ala Leu Ala Ala Gly Asn Ser Val Ile Leu Lys Pro
            180                 185                 190 tct gaa aaa tca ccg ctc agt gcg att cgt ctc gcg ggg ctg gcg aaa     624
Ser Glu Lys Ser Pro Leu Ser Ala Ile Arg Leu Ala Gly Leu Ala Lys
        195                 200                 205 gaa gca ggc ttg ccg gat ggt gtg ttg aac gtg gtg acg ggt ttt ggt     672
Glu Ala Gly Leu Pro Asp Gly Val Leu Asn Val Val Thr Gly Phe Gly
    210                 215                 220 cat gaa gcc ggg cag gcg ctg tcg cgt cat aac gat atc gac gcc att     720
His Glu Ala Gly Gln Ala Leu Ser Arg His Asn Asp Ile Asp Ala Ile
225                 230                 235                 240 gcc ttt acc ggt tca acc cgt acc ggg aaa cag ctg ctg aaa gat gcg     768
Ala Phe Thr Gly Ser Thr Arg Thr Gly Lys Gln Leu Leu Lys Asp Ala
                245                 250                 255 ggc gac agc aac atg aaa cgc gtc tgg ctg gaa gcg ggc ggc aaa agc     816
Gly Asp Ser Asn Met Lys Arg Val Trp Leu Glu Ala Gly Gly Lys Ser
            260                 265                 270 gcc aac atc gtt ttc gct gac tgc ccg gat ttg caa cag gcg gca agc     864
Ala Asn Ile Val Phe Ala Asp Cys Pro Asp Leu Gln Gln Ala Ala Ser
        275                 280                 285 gcc acc gca gca ggc att ttc tac aac cag gga cag gtg tgc atc gcc     912
Ala Thr Ala Ala Gly Ile Phe Tyr Asn Gln Gly Gln Val Cys Ile Ala
    290                 295                 300 gga acg cgc ctg ttg ctg gaa gag agc atc gcc gat gaa ttc tta gcc     960
Gly Thr Arg Leu Leu Leu Glu Glu Ser Ile Ala Asp Glu Phe Leu Ala
305                 310                 315                 320 ctg tta aaa cag cag gcg caa aac tgg cag ccg ggc cat cca ctt gat    1008
Leu Leu Lys Gln Gln Ala Gln Asn Trp Gln Pro Gly His Pro Leu Asp
                325                 330                 335 ccc gca acc acc atg ggc acc tta atc gac tgc gcc cac gcc gac tcg    1056
Pro Ala Thr Thr Met Gly Thr Leu Ile Asp Cys Ala His Ala Asp Ser
            340                 345                 350 gtc cat agc ttt att cgg gaa ggc gaa agc aaa ggg caa ctg ttg ttg    1104
Val His Ser Phe Ile Arg Glu Gly Glu Ser Lys Gly Gln Leu Leu Leu
        355                 360                 365 gat ggc cgt aac gcc ggg ctg gct gcc gcc atc ggc ccg acc atc ttt    1152
Asp Gly Arg Asn Ala Gly Leu Ala Ala Ala Ile Gly Pro Thr Ile Phe
    370                 375                 380 gtg gat gtg gac ccg aat gcg tcc tta agt cgc gaa gag att ttc ggt    1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag    1248
Pro Val Leu Val Val Thr Arg Phe Thr Ser Glu Glu Gln Ala Leu Gln
                405                 410                 415 ctt gcc aac gac agc cag tac ggc ctt ggc gcg gcg gta tgg acg cgc    1296
Leu Ala Asn Asp Ser Gln Tyr Gly Leu Gly Ala Ala Val Trp Thr Arg
            420                 425                 430 gac ctc tcc cgc gcg cac cgc atg agc cga cgc ctg aaa gcc ggt tcc    1344
Asp Leu Ser Arg Ala His Arg Met Ser Arg Arg Leu Lys Ala Gly Ser
        435                 440                 445 gtc ttc gtc aat aac tac aac gac ggc gat atg acc gtg ccg ttt ggc    1392
Val Phe Val Asn Asn Tyr Asn Asp Gly Asp Met Thr Val Pro Phe Gly
    450                 455                 460
```

```
ggc tat aag cag agc ggc aac ggt cgc gac aaa tcc ctg cat gcc ctt   1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga   1488
Glu Lys Phe Thr Glu Leu Lys Thr Ile Trp Ile Ser Leu Glu Ala
                485                 490                 495

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
    130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
    210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
```

```
                 340             345             350
Val His Ser Phe Ile Arg Glu Gly Glu Ser Lys Gly Gln Leu Leu Leu
            355             360             365

Asp Gly Arg Asn Ala Gly Leu Ala Ala Ala Ile Gly Pro Thr Ile Phe
        370             375             380

Val Asp Val Asp Pro Asn Ala Ser Leu Ser Arg Glu Glu Ile Phe Gly
385             390             395             400

Pro Val Leu Val Val Thr Arg Phe Thr Ser Glu Glu Ala Leu Gln
            405             410             415

Leu Ala Asn Asp Ser Gln Tyr Gly Leu Gly Ala Ala Val Trp Thr Arg
        420             425             430

Asp Leu Ser Arg Ala His Arg Met Ser Arg Leu Lys Ala Gly Ser
            435             440             445

Val Phe Val Asn Asn Tyr Asn Asp Gly Asp Met Thr Val Pro Phe Gly
        450             455             460

Gly Tyr Lys Gln Ser Gly Asn Gly Arg Asp Lys Ser Leu His Ala Leu
465             470             475             480

Glu Lys Phe Thr Glu Leu Lys Thr Ile Trp Ile Ser Leu Glu Ala
            485             490             495

<210> SEQ ID NO 21
<211> LENGTH: 1395
<212> TYPE: DNA
<213> ORGANISM: Escherichia coli

<400> SEQUENCE: 21
atgcctgacg ctaaaaaaca ggggcggtca acaaggcaa tgacgttttt cgtctgcttc      60
cttgccgctc tggcgggatt actctttggc ctggatatcg gtgtaattgc tggcgcactg     120
ccgtttattg cagatgaatt ccagattact cgcacacgc aagaatgggt cgtaagctcc     180
atgatgttcg gtgcggcagt cggtgcggtg ggcagcggct ggctctcctt taaactcggg     240
cgcaaaaaga gcctgatgat cggcgcaatt ttgtttgttg ccggttcgct gttctctgcg     300
gctgcgccaa cgttgaagt actgattctt cccgcgttc tactgggggct ggcggtgggt     360 gtggcctctt ataccgcacc gctgtacctc tctgaaattg cgccggaaaa aattcgtggc     420
agtatgatct cgatgtatca gttgatgatc actatcggga tcctcggtgc ttatcttttct     480 gataccgcct tcagctacac cggtgcatgg cgctggatgc tgggtgtgat tatcatcccg     540 gcaatttttgc tgctgattgg tgtcttcttc ctgccagaca gcccacgttg gtttgccgcc     600
aaacgccgtt ttgttgatgc cgaacgcgtg ctgctacgcc tgcgtgacac cagcgcggaa     660
gcgaaacgcg aactggatga atccgtgaa agttttgcagg ttaaacagag tggctgggcg     720
ctgtttaaag agaacagcaa cttccgccgc gcggtgttcc ttggcgtact gttgcaggta     780
atgcagcaat tcaccgggat gaacgtcatc atgtattacg cgccgaaaat cttcgaactg     840
gcgggttata ccaacactac cgagcaaatg tggggaccg tgattgtcgg cctgaccaac     900
gtacttgcca cctttatcgc aatcggcctt gttgaccgct ggggacgtaa accaacgcta     960
acgctgggct tcctggtgat ggctgctggc atgggcgtac tcggtacaat gatgcatatc    1020
ggtattcact ctccgtcggc gcagtatttc gccatcgcca tgctgctgat gtttattgtc    1080
ggttttgcca tgagtgccgg tccgctgatt tgggtactgt gctccgaaat tcagccgctg    1140
aaaggccgcg atttttggca cacctgctcc actgccacca actggattgc aacatgatc    1200 gttggcgcaa cgttcctgac catgctcaac acgctgggta acgccaacac cttcgggtg    1260 tatgcggctc tgaacgtact gtttatcctg ctgacattgt ggctggtacc ggaaaccaaa    1320
```
cacgtttcgc tggaacatat tgaacgtaat ctgatgaaag gtcgtaaact gcgcgaaata    1380
ggcgctcacg attaa                                                     1395

<210> SEQ ID NO 22
<211> LENGTH: 464
<212> TYPE: PRT
<213> ORGANISM: Escherichia coli

<400> SEQUENCE: 22

Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Phe Gly Leu Asp
                20                  25                  30

Ile Gly Val Ile Ala Gly Ala Leu Pro Phe Ile Ala Asp Glu Phe Gln
            35                  40                  45

Ile Thr Ser His Thr Gln Glu Trp Val Val Ser Met Met Phe Gly
        50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Pro Asn Val Glu Val Leu Ile Leu Ser Arg
                100                 105                 110

Val Leu Leu Gly Leu Ala Val Gly Val Ala Ser Tyr Thr Ala Pro Leu
            115                 120                 125

Tyr Leu Ser Glu Ile Ala Pro Glu Lys Ile Arg Gly Ser Met Ile Ser
        130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Leu Ile Gly Val Phe Phe Leu Pro
            180                 185                 190

Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
    210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
    290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro

```
                        355                 360                 365
Leu Ile Trp Val Leu Cys Ser Glu Ile Gln Pro Leu Lys Gly Arg Asp
            370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
    450                 455                 460

<210> SEQ ID NO 23
<211> LENGTH: 1164
<212> TYPE: DNA
<213> ORGANISM: Klebsiella pneumoniae

<400> SEQUENCE: 23
tcagaatgcc tggcggaaaa tcgcggcaat ctcctgctcg ttgcctttac gcgggttcga      60
gaacgcattg ccgtctttca gagccatctc cgccatgtag gggaagtcgg cctcttttac    120
tcccagatcg cgcagatgct gcggaatacc gatatccatc gacagacgcg tgatagcggc    180
gatggctttt ccgccgcgt cgagagtgga cagtccggtg atattttcgc ccatcagttc     240
agcgatatcg gcgaatttct ccgggttggc gatcaggttg tagcgggcca catgcggcag    300
caggacagcg ttggccacgc cgtgcggcat gtcgtacagg ccgcccagct ggtgcgccat    360
ggcgtgcacg tagccgaggt tggcgttatt gaaagccatc ccggccagca gagaggcata    420
ggccatgttt cccgcgcct gcagattgct gccgagggcc acggcctggc gcaggttgcg     480
ggcgatgagg cggatcgcct gcatggcggc ggcgtccgtc accgggttag cgtctttgga    540
gatataggcc tctacggcgt gggtcagggc atccatcccg gtcgccgcgg tcagggcggc    600
cggtttaccg atcatcagca gcggatcgtt gatagagacc gacggcaggt tgcgccagct    660
gacgatcaca aacttcactt tggttttcggt gttggtcagg acgcagtggc gggtgacctc    720
gctggcggtg ccggcggtgg tattgaccgc gacgataggc ggcagcgggt tggtcagggt    780
ctcgattccg gcatactggt acagatcgcc ctcatgggtg gcggcgatgc cgatgccttt    840
gccgcaatcg tgcgggctgc cgccgcccac ggtgacgatg atgtcgcact gttcgcggcg    900
aaacacggcg aggccgtcgc gcacgttggt gtctttcggg ttcggctcga cgccgtcaaa    960
gatcgccacc tcgatcccgg cctcccgcag ataatgcagg gttttgtcca ctgcgccatc   1020
tttaattgcc cgcaggcctt tgtcggtgac cagcagggct tttttccccc ccagcagctg   1080
gcagcgttcg ccgactacgg aaatggcgtt ggggccaaaa aagttaacgt ttggcaccag   1140
ataatcaaac atacgatagc tcat                                          1164

<210> SEQ ID NO 24
<211> LENGTH: 387
<212> TYPE: PRT
<213> ORGANISM: Klebsiella pneumoniae

<400> SEQUENCE: 24

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
```

20                  25                  30
Gly Lys Lys Ala Leu Leu Val Thr Asp Lys Gly Leu Arg Ala Ile Lys
            35                  40                  45
Asp Gly Ala Val Asp Lys Thr Leu His Tyr Leu Arg Glu Ala Gly Ile
 50                  55                  60
Glu Val Ala Ile Phe Asp Gly Val Glu Pro Asn Pro Lys Asp Thr Asn
 65                  70                  75                  80
Val Arg Asp Gly Leu Ala Val Phe Arg Arg Glu Gln Cys Asp Ile Ile
                85                  90                  95
Val Thr Val Gly Gly Gly Ser Pro His Asp Cys Gly Lys Gly Ile Gly
                100                 105                 110
Ile Ala Ala Thr His Glu Gly Asp Leu Tyr Gln Tyr Ala Gly Ile Glu
                115                 120                 125
Thr Leu Thr Asn Pro Leu Pro Pro Ile Val Ala Val Asn Thr Thr Ala
            130                 135                 140
Gly Thr Ala Ser Glu Val Thr Arg His Cys Val Leu Thr Asn Thr Glu
145                 150                 155                 160
Thr Lys Val Lys Phe Val Ile Val Ser Trp Arg Asn Leu Pro Ser Val
                165                 170                 175
Ser Ile Asn Asp Pro Leu Leu Met Ile Gly Lys Pro Ala Ala Leu Thr
                180                 185                 190
Ala Ala Thr Gly Met Asp Ala Leu Thr His Ala Val Glu Ala Tyr Ile
                195                 200                 205
Ser Lys Asp Ala Asn Pro Val Thr Asp Ala Ala Met Gln Ala Ile
                210                 215                 220
Arg Leu Ile Ala Arg Asn Leu Arg Gln Ala Val Ala Leu Gly Ser Asn
225                 230                 235                 240
Leu Gln Ala Arg Glu Asn Met Ala Tyr Ala Ser Leu Leu Ala Gly Met
                245                 250                 255
Ala Phe Asn Asn Ala Asn Leu Gly Tyr Val His Ala Met Ala His Gln
                260                 265                 270
Leu Gly Gly Leu Tyr Asp Met Pro His Gly Val Ala Asn Ala Val Leu
                275                 280                 285
Leu Pro His Val Ala Arg Tyr Asn Leu Ile Ala Asn Pro Glu Lys Phe
            290                 295                 300
Ala Asp Ile Ala Glu Leu Met Gly Glu Asn Ile Thr Gly Leu Ser Thr
305                 310                 315                 320
Leu Asp Ala Ala Glu Lys Ala Ile Ala Ala Ile Thr Arg Leu Ser Met
                325                 330                 335
Asp Ile Gly Ile Pro Gln His Leu Arg Asp Leu Gly Val Lys Glu Ala
                340                 345                 350
Asp Phe Pro Tyr Met Ala Glu Met Ala Leu Lys Asp Gly Asn Ala Phe
            355                 360                 365
Ser Asn Pro Arg Lys Gly Asn Glu Gln Glu Ile Ala Ala Ile Phe Arg
            370                 375                 380
Gln Ala Phe
385

<210> SEQ ID NO 25
<211> LENGTH: 1824
<212> TYPE: DNA
<213> ORGANISM: Klebsiella pneumoniae
<220> FEATURE:
<221> NAME/KEY: CDS
<222> LOCATION: (1)..(1824)

<400> SEQUENCE: 25

```
atg ccg tta ata gcc ggg att gat atc ggc aac gcc acc acc gag gtg      48
Met Pro Leu Ile Ala Gly Ile Asp Ile Gly Asn Ala Thr Thr Glu Val
1               5                   10                  15 gcg ctg gcg tcc gac tac ccg cag gcg agg gcg ttt gtt gcg agc ggg      96
Ala Leu Ala Ser Asp Tyr Pro Gln Ala Arg Ala Phe Val Ala Ser Gly
                20                  25                  30 atc gtc gcg acg acg ggc atg aaa ggg acg cgg gac aat atc gcc ggg     144
Ile Val Ala Thr Thr Gly Met Lys Gly Thr Arg Asp Asn Ile Ala Gly
            35                  40                  45 acc ctc gcc gcg ctg gag cag gcc ctg gcg aaa aca ccg tgg tcg atg     192
Thr Leu Ala Ala Leu Glu Gln Ala Leu Ala Lys Thr Pro Trp Ser Met
50                  55                  60 agc gat gtc tct cgc atc tat ctt aac gaa gcc gcg ccg gtg att ggc     240
Ser Asp Val Ser Arg Ile Tyr Leu Asn Glu Ala Ala Pro Val Ile Gly
65                  70                  75                  80 gat gtg gcg atg gag acc atc acc gag acc att atc acc gaa tcg acc     288
Asp Val Ala Met Glu Thr Ile Thr Glu Thr Ile Ile Thr Glu Ser Thr
                85                  90                  95 atg atc ggt cat aac ccg cag acg ccg ggc ggg gtg ggc gtt ggc gtg     336
Met Ile Gly His Asn Pro Gln Thr Pro Gly Gly Val Gly Val Gly Val
            100                 105                 110 ggg acg act atc gcc ctc ggg cgg ctg gcg acg ctg ccg gcg gcg cag     384
Gly Thr Thr Ile Ala Leu Gly Arg Leu Ala Thr Leu Pro Ala Ala Gln
        115                 120                 125 tat gcc gag ggg tgg atc gta ctg att gac gac gcc gtc gat ttc ctt     432
Tyr Ala Glu Gly Trp Ile Val Leu Ile Asp Asp Ala Val Asp Phe Leu
    130                 135                 140 gac gcc gtg tgg tgg ctc aat gag gcg ctc gac cgg ggg atc aac gtg     480
Asp Ala Val Trp Trp Leu Asn Glu Ala Leu Asp Arg Gly Ile Asn Val
145                 150                 155                 160 gtg gcg gcg atc ctc aaa aag gac gac ggc gtg ctg gtg aac aac cgc     528
Val Ala Ala Ile Leu Lys Lys Asp Asp Gly Val Leu Val Asn Asn Arg
                165                 170                 175 ctg cgt aaa acc ctg ccg gtg gtg gat gaa gtg acg ctg ctg gag cag     576
Leu Arg Lys Thr Leu Pro Val Val Asp Glu Val Thr Leu Leu Glu Gln
            180                 185                 190 gtc ccc gag ggg gta atg gcg gcg gtg gaa gtg gcc gcg ccg ggc cag     624
Val Pro Glu Gly Val Met Ala Ala Val Glu Val Ala Ala Pro Gly Gln
        195                 200                 205 gtg gtg cgg atc ctg tcg aat ccc tac ggg atc gcc acc ttc ttc ggg     672
Val Val Arg Ile Leu Ser Asn Pro Tyr Gly Ile Ala Thr Phe Phe Gly
    210                 215                 220 cta agc ccg gaa gag acc cag gcc atc gtc ccc atc gcc cgc gcc ctg     720
Leu Ser Pro Glu Glu Thr Gln Ala Ile Val Pro Ile Ala Arg Ala Leu
225                 230                 235                 240 att ggc aac cgt tcc gcg gtg gtg ctc aag acc ccg cag ggg gat gtg     768
Ile Gly Asn Arg Ser Ala Val Val Leu Lys Thr Pro Gln Gly Asp Val
                245                 250                 255 cag tcg cgg gtg atc ccg gcg ggc aac ctc tac att agc ggc gaa aag     816
Gln Ser Arg Val Ile Pro Ala Gly Asn Leu Tyr Ile Ser Gly Glu Lys
            260                 265                 270 cgc cgc gga gag gcc gat gtc gcc gag ggc gcg gaa gcc atc atg cag     864
Arg Arg Gly Glu Ala Asp Val Ala Glu Gly Ala Glu Ala Ile Met Gln
        275                 280                 285 gcg atg agc gcc tgc gct ccg gta cgc gac atc cgc ggc gaa ccg ggc     912
Ala Met Ser Ala Cys Ala Pro Val Arg Asp Ile Arg Gly Glu Pro Gly
    290                 295                 300 acc cac gcc ggc ggc atg ctt gag cgg gtg cgc aag gta atg gcg tcc     960
Thr His Ala Gly Gly Met Leu Glu Arg Val Arg Lys Val Met Ala Ser
```

```
                305                 310                 315                 320
ctg acc ggc cat gag atg agc gcg ata tac atc cag gat ctg ctg gcg            1008
Leu Thr Gly His Glu Met Ser Ala Ile Tyr Ile Gln Asp Leu Leu Ala
                    325                 330                 335 gtg gat acg ttt att ccg cgc aag gtg cag ggc ggg atg gcc ggc gag            1056
Val Asp Thr Phe Ile Pro Arg Lys Val Gln Gly Gly Met Ala Gly Glu
                340                 345                 350 tgc gcc atg gag aat gcc gtc ggg atg gcg gcg atg gtg aaa gcg gat            1104
Cys Ala Met Glu Asn Ala Val Gly Met Ala Ala Met Val Lys Ala Asp
            355                 360                 365 cgt ctg caa atg cag gtt atc gcc cgc gaa ctg agc gcc cga ctg cag            1152
Arg Leu Gln Met Gln Val Ile Ala Arg Glu Leu Ser Ala Arg Leu Gln
        370                 375                 380 acc gag gtg gtg gtg ggc ggc gtg gag gcc aac atg gcc atc gcc ggg            1200
Thr Glu Val Val Val Gly Gly Val Glu Ala Asn Met Ala Ile Ala Gly
385                 390                 395                 400 gcg tta acc act ccc ggc tgt gcg gcg ccg ctg gcg atc ctc gac ctc            1248
Ala Leu Thr Thr Pro Gly Cys Ala Ala Pro Leu Ala Ile Leu Asp Leu
                405                 410                 415 ggc gcc ggc tcg acg gat gcg gcg atc gtc aac gcg gag ggg cag ata            1296
Gly Ala Gly Ser Thr Asp Ala Ala Ile Val Asn Ala Glu Gly Gln Ile
                420                 425                 430 acg gcg gtc cat ctc gcc ggg gcg ggg aat atg gtc agc ctg ttg att            1344
Thr Ala Val His Leu Ala Gly Ala Gly Asn Met Val Ser Leu Leu Ile
            435                 440                 445 aaa acc gag ctg ggc ctc gag gat ctt tcg ctg gcg gaa gcg ata aaa            1392
Lys Thr Glu Leu Gly Leu Glu Asp Leu Ser Leu Ala Glu Ala Ile Lys
        450                 455                 460 aaa tac ccg ctg gcc aaa gtg gaa agc ctg ttc agt att cgt cac gag            1440
Lys Tyr Pro Leu Ala Lys Val Glu Ser Leu Phe Ser Ile Arg His Glu
465                 470                 475                 480 aat ggc gcg gtg gag ttc ttt cgg gaa gcc ctc agc ccg gcg gtg ttc            1488
Asn Gly Ala Val Glu Phe Phe Arg Glu Ala Leu Ser Pro Ala Val Phe
                485                 490                 495 gcc aaa gtg gtg tac atc aag gag ggc gaa ctg gtg ccg atc gat aac            1536
Ala Lys Val Val Tyr Ile Lys Glu Gly Glu Leu Val Pro Ile Asp Asn
                500                 505                 510 gcc agc ccg ctg gaa aaa att cgt ctc gtg cgc cgg cag gcg aaa gag            1584
Ala Ser Pro Leu Glu Lys Ile Arg Leu Val Arg Arg Gln Ala Lys Glu
            515                 520                 525 aaa gtg ttt gtc acc aac tgc ctg cgc gcg ctg cgc cag gtc tca ccc            1632
Lys Val Phe Val Thr Asn Cys Leu Arg Ala Leu Arg Gln Val Ser Pro
        530                 535                 540 ggc ggt tcc att cgc gat atc gcc ttt gtg gtg ctg gtg ggc ggc tca            1680
Gly Gly Ser Ile Arg Asp Ile Ala Phe Val Val Leu Val Gly Gly Ser
545                 550                 555                 560 tcg ctg gac ttt gag atc ccg cag ctt atc acg gaa gcc ttg tcg cac            1728
Ser Leu Asp Phe Glu Ile Pro Gln Leu Ile Thr Glu Ala Leu Ser His
                565                 570                 575 tat ggc gtg gtc gcc ggg cag ggc aat att cgg gga aca gaa ggg ccg            1776
Tyr Gly Val Val Ala Gly Gln Gly Asn Ile Arg Gly Thr Glu Gly Pro
                580                 585                 590 cgc aat gcg gtc gcc acc ggg ctg cta ctg gcc ggt cag gcg aat taa            1824
Arg Asn Ala Val Ala Thr Gly Leu Leu Leu Ala Gly Gln Ala Asn
            595                 600                 605

<210> SEQ ID NO 26
<211> LENGTH: 607
<212> TYPE: PRT
<213> ORGANISM: Klebsiella pneumoniae
```

<400> SEQUENCE: 26

```
Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Thr Glu Ser Thr
                85                  90                  95

Met Ile Gly His Asn Pro Gln Thr Pro Gly Gly Val Gly Val
                100                 105                 110

Gly Thr Thr Ile Ala Leu Gly Arg Leu Ala Thr Leu Pro Ala Ala Gln
                115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
                180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
        210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
                260                 265                 270

Arg Arg Gly Glu Ala Asp Val Ala Glu Gly Ala Glu Ala Ile Met Gln
                275                 280                 285

Ala Met Ser Ala Cys Ala Pro Val Arg Asp Ile Arg Gly Glu Pro Gly
        290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
                340                 345                 350

Cys Ala Met Glu Asn Ala Val Gly Met Ala Ala Met Val Lys Ala Asp
        355                 360                 365

Arg Leu Gln Met Gln Val Ile Ala Arg Glu Leu Ser Ala Arg Leu Gln
    370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415
```

| | | | | | | | | | | |
|---|---|---|---|---|---|---|---|---|---|---|
|Gly|Ala|Gly|Ser|Thr|Asp|Ala|Ala|Ile|Val|Asn|Ala|Glu|Gly|Gln|Ile|
| | | |420| | |425| | | |430| | | | | |

Thr Ala Val His Leu Ala Gly Ala Gly Asn Met Val Ser Leu Leu Ile
         435                 440                 445

Lys Thr Glu Leu Gly Leu Glu Asp Leu Ser Leu Ala Glu Ala Ile Lys
450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
                500                 505                 510

Ala Ser Pro Leu Glu Lys Ile Arg Leu Val Arg Arg Gln Ala Lys Glu
            515                 520                 525

Lys Val Phe Val Thr Asn Cys Leu Arg Ala Leu Arg Gln Val Ser Pro
        530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
                580                 585                 590

Arg Asn Ala Val Ala Thr Gly Leu Leu Leu Ala Gly Gln Ala Asn
            595                 600                 605

<210> SEQ ID NO 27
<211> LENGTH: 1959
<212> TYPE: DNA
<213> ORGANISM: Escherichia coli

<400> SEQUENCE: 27

```
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gccccggta atgtgtccat aaatggtac gaggacggca cgctgaatct ggcggcaaac     240
tgccttgacc gccatctgca agaaaacggc gatcgtaccg ccatcatctg ggaaggcgac     300
gacgccagcc agagcaaaca tatcagctat aaagagctgc accgcgacgt ctgccgcttc     360
gccaataccc tgctcgagct gggcattaaa aaggtgatg tggtggcgat ttatatgccg     420
atggtgccgg aagccgcggt tgcgatgctg gcctgcgccc gcattggcgc ggtgcattcg     480
gtgattttcg gcggcttctc gccggaagcc gttgccgggc gcattattga ttccaactca     540
cgactggtga tcacttccga cgaaggtgtg cgtgccgggc agtattcc gctgaagaaa     600
aacgttgatg acgcgctgaa aaacccgaac gtcaccagcg tagagcatgt ggtggtactg     660
aagcgtactg gcgggaaaat tgactggcag gaagggcgcg acctgtggtg gcacgacctg     720
gttgagcaag cgagcgatca gcaccaggcg aagagatga acgccgaaga tccgctgttt     780
attctctaca cctccggttc taccggtaag ccaaaaggtg tgctgcatac taccggcggt     840
tatctggtgt acgcggcgct gaccttaaa tatgtctttg attatcatcc gggtgatatc     900
tactggtgca ccgccgatgt gggctgggtg accggacaca gttacttgct gtacggcccg     960
ctggcctgcg gtcgaccac gctgatgttt gaaggcgtac ccaactggcc gacgcctgcc    1020
cgtatggcgc aggtggtgga caagcatcag gtcaatattc tctataccgc acccacggcg    1080
```

```
atccgcgcgc tgatggcgga aggcgataaa gcgatcgaag gcaccgaccg ttcgtcgctg    1140
cgcattctcg gttccgtggg cgagccaatt aacccggaag cgtgggagtg gtactggaaa    1200
aaaatcggca acgagaaatg tccggtggtc gatacctggt ggcagaccga accggcggt     1260
ttcatgatca ccccgctgcc tggcgctacc gagctgaaag ccggttcggc aacacgtccg    1320
ttcttcggcg tgcaaccggc gctggtcgat aacgaaggta acccgctgga ggggccacc     1380
gaaggtagcc tggtaatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtgga cgacgtgctg     1560
aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aacccgctc cggcaaaatt atgcgccgta ttctgcgcaa aattgcggcg     1860
ggcgatacca gcaacctggg cgatacctcg acgcttgccg atcctggcgt agtcgagaag    1920
ctgcttgaag agaagcaggc tatcgcgatg ccatcgtaa                           1959
```

<210> SEQ ID NO 28
<211> LENGTH: 652
<212> TYPE: PRT
<213> ORGANISM: Escherichia coli

<400> SEQUENCE: 28

```
Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
            20                  25                  30

Asn Val Pro Asp Thr Phe Trp Gly Glu Gln Gly Lys Ile Leu Asp Trp
        35                  40                  45

Ile Lys Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
            100                 105                 110

Leu His Arg Asp Val Cys Arg Phe Ala Asn Thr Leu Leu Glu Leu Gly
        115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
            180                 185                 190

Gly Arg Ser Ile Pro Leu Lys Lys Asn Val Asp Asp Ala Leu Lys Asn
        195                 200                 205

Pro Asn Val Thr Ser Val Glu His Val Val Val Leu Lys Arg Thr Gly
    210                 215                 220
```

```
Gly Lys Ile Asp Trp Gln Glu Gly Arg Asp Leu Trp Trp His Asp Leu
225                 230                 235                 240

Val Glu Gln Ala Ser Asp Gln His Gln Ala Glu Met Asn Ala Glu
                245                 250                 255

Asp Pro Leu Phe Ile Leu Tyr Thr Ser Gly Thr Gly Lys Pro Lys
                260                 265                 270

Gly Val Leu His Thr Thr Gly Gly Tyr Leu Val Tyr Ala Ala Leu Thr
                275                 280                 285

Phe Lys Tyr Val Phe Asp Tyr His Pro Gly Asp Ile Tyr Trp Cys Thr
290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
                340                 345                 350

Ile Leu Tyr Thr Ala Pro Thr Ala Ile Arg Ala Leu Met Ala Glu Gly
                355                 360                 365

Asp Lys Ala Ile Glu Gly Thr Asp Arg Ser Ser Leu Arg Ile Leu Gly
370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
                405                 410                 415

Glu Thr Gly Gly Phe Met Ile Thr Pro Leu Pro Gly Ala Thr Glu Leu
                420                 425                 430

Lys Ala Gly Ser Ala Thr Arg Pro Phe Phe Gly Val Gln Pro Ala Leu
                435                 440                 445

Val Asp Asn Glu Gly Asn Pro Leu Glu Gly Ala Thr Glu Gly Ser Leu
                450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
                500                 505                 510

Thr Gly Arg Val Asp Asp Val Leu Asn Val Ser Gly His Arg Leu Gly
                515                 520                 525

Thr Ala Glu Ile Glu Ser Ala Leu Val Ala His Pro Lys Ile Ala Glu
                530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
                580                 585                 590

Pro Asp Val Leu His Trp Thr Asp Ser Leu Pro Lys Thr Arg Ser Gly
                595                 600                 605

Lys Ile Met Arg Arg Ile Leu Arg Lys Ile Ala Ala Gly Asp Thr Ser
610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650
```

<210> SEQ ID NO 29
<211> LENGTH: 2142
<212> TYPE: DNA
<213> ORGANISM: Saccharomyces cerevisiae

<400> SEQUENCE: 29

| | | | | | | |
|---|---|---|---|---|---|---|
| atgtcgccct | ctgccgtaca | atcatcaaaa | ctagaagaac | agtcaagtga | aattgacaag | 60 |
| ttgaaagcaa | aaatgtccca | gtctgccgcc | actgcgcagc | agaagaagga | acatgagtat | 120 |
| gaacatttga | cttcggtcaa | gatcgtgcca | caacggccca | tctcagatag | actgcagccc | 180 |
| gcaattgcta | cccactattc | tccacacttg | gacgggttgc | aggactatca | gcgcttgcac | 240 |
| aaggagtcta | ttgaagaccc | tgctaagttc | ttcggttcta | aagctaccca | atttttaaac | 300 |
| tggtctaagc | cattcgataa | ggtgttcatc | ccagacccta | aaacgggcag | gccctccttc | 360 |
| cagaacaatg | catggttcct | caacggccaa | ttaaacgcct | gttacaactg | tgttgacaga | 420 |
| catgccttga | agactcctaa | caagaaagcc | attattttcg | aaggtgacga | gcctggccaa | 480 |
| ggctattcca | ttacctacaa | ggaactactt | gaagaagttt | gtcaagtggc | acaagtgctg | 540 |
| acttactcta | tgggcgttcg | caagggcgat | actgttgccg | tgtacatgcc | tatggtccca | 600 |
| gaagcaatca | taaccttgtt | ggccatttcc | cgtatcggtg | ccattcactc | cgtagtcttt | 660 |
| gccgggtttt | cttccaactc | cttgagagat | cgtatcaacg | atgggactc | taaagttgtc | 720 |
| atcactacag | atgaatccaa | cagaggtggt | aaagtcattg | agactaaaag | aattgttgat | 780 |
| gacgcgctaa | gagagacccc | aggcgtgaga | cacgtcttgg | tttatagaaa | gaccaacaat | 840 |
| ccatctgttg | ctttccatgc | ccccagagat | ttggattggg | caacagaaaa | gaagaaatac | 900 |
| aagacctact | atccatgcac | acccgttgat | tctgaggatc | cattattctt | gttgtatacg | 960 |
| tctggttcta | ctggtgcccc | caagggtgtt | caacattcta | ccgcaggtta | cttgctggga | 1020 |
| gctttgttga | ccatgcgcta | cacttttgac | actcaccaag | aagacgtttt | cttcacagct | 1080 |
| ggagacattg | gctggattac | aggccacact | tatgtggttt | atggtcccct | actatatggt | 1140 |
| tgtgccactt | tggtctttga | agggactcct | gcgtacccaa | attactcccg | ttattgggat | 1200 |
| attattgatg | aacacaaagt | cacccaattt | tatgttgcgc | caactgctttt | gcgtttgttg | 1260 |
| aaaagagctg | gtgattccta | catcgaaaat | cattccttaa | aatctttgcg | ttgcttgggt | 1320 |
| tcggtcggtg | agccaattgc | tgctgaagtt | tgggagtggt | actctgaaaa | aataggtaaa | 1380 |
| aatgaaatcc | ccattgtaga | cacctactgg | caaacagaat | ctggttcgca | tctggtcacc | 1440 |
| ccgctggctg | gtggtgttac | accaatgaaa | ccgggttctg | cctcattccc | cttcttcggt | 1500 |
| attgatgcag | ttgttcttga | ccctaacact | ggtgaagaac | ttaacaccag | ccacgcagag | 1560 |
| ggtgtccttg | ccgtcaaagc | tgcatggcca | tcatttgcaa | gaactatttg | gaaaaatcat | 1620 |
| gataggtatc | tagacactta | tttgaaccct | taccctggct | actatttcac | tggtgatggt | 1680 |
| gctgcaaagg | ataaggatgg | ttatatctgg | attttgggtc | gtgtagacga | tgtggtgaac | 1740 |
| gtctctggtc | accgtctgtc | taccgctgaa | attgaggctg | ctattatcga | agatccaatt | 1800 |
| gtggccgagt | gtgctgttgt | cggattcaac | gatgacttga | ctggtcaagc | agttgctgca | 1860 |
| tttgtggtgt | tgaaaaacaa | atctagttgg | tccaccgcaa | cagatgatga | attacaagat | 1920 |
| atcaagaagc | atttggtctt | tactgttaga | aagacatcg | ggccatttgc | cgcaccaaaa | 1980 |
| ttgatcattt | tagtggatga | cttgcccaag | acaagatccg | gcaaaattat | gagacgtatt | 2040 |
| ttaagaaaaa | tcctagcagg | agaaagtgac | caactaggcg | acgtttctac | attgtcaaac | 2100 |
| cctggcattg | ttagacatct | aattgattcg | gtcaagttgt | aa | | 2142 |

<210> SEQ ID NO 30
<211> LENGTH: 713
<212> TYPE: PRT
<213> ORGANISM: Saccharomyces cerevisiae

<400> SEQUENCE: 30

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Phe Gly Ser Lys Ala Thr
                85                  90                  95

Gln Phe Leu Asn Trp Ser Lys Pro Phe Asp Lys Val Phe Ile Pro Asp
            100                 105                 110

Pro Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
370                 375                 380

| | | | | | | | | | | | | | | |
|---|---|---|---|---|---|---|---|---|---|---|---|---|---|---|
|Val|Phe|Glu|Gly|Thr|Pro|Ala|Tyr|Pro|Asn|Tyr|Ser|Arg|Tyr|Trp|Asp|
|385| | | |390| | | |395| | | |400| | |

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
    450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe
                485                 490                 495

Pro Phe Phe Gly Ile Asp Ala Val Val Leu Asp Pro Asn Thr Gly Glu
            500                 505                 510

Glu Leu Asn Thr Ser His Ala Glu Gly Val Leu Ala Val Lys Ala Ala
        515                 520                 525

Trp Pro Ser Phe Ala Arg Thr Ile Trp Lys Asn His Asp Arg Tyr Leu
    530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
                565                 570                 575

Asp Val Val Asn Val Ser Gly His Arg Leu Ser Thr Ala Glu Ile Glu
            580                 585                 590

Ala Ala Ile Ile Glu Asp Pro Ile Val Ala Glu Cys Ala Val Val Gly
        595                 600                 605

Phe Asn Asp Asp Leu Thr Gly Gln Ala Val Ala Phe Val Val Leu
    610                 615                 620

Lys Asn Lys Ser Ser Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
            660                 665                 670

Ser Gly Lys Ile Met Arg Arg Ile Leu Arg Lys Ile Leu Ala Gly Glu
        675                 680                 685

Ser Asp Gln Leu Gly Asp Val Ser Thr Leu Ser Asn Pro Gly Ile Val
    690                 695                 700

Arg His Leu Ile Asp Ser Val Lys Leu
705                 710

<210> SEQ ID NO 31
<211> LENGTH: 2052
<212> TYPE: DNA
<213> ORGANISM: Saccharomyces cerevisiae

<400> SEQUENCE: 31
atgacaatca aggaacataa agtagtttat gaagctcaca cgtaaaggc tcttaaggct      60 cctcaacatt tttacaacag ccaacccggc aagggttacg ttactgatat gcaacattat     120
caagaaatgt atcaacaatc tatcaatgag ccagaaaaat tctttgataa gatggctaag    180
gaatacttgc attgggatgc tccatacacc aaagttcaat ctggttcatt gaacaatggt    240

```
gatgttgcat ggttttgaa cggtaaattg aatgcatcat acaattgtgt tgacagacat    300
gcctttgcta atcccgacaa gccagctttg atctatgaag ctgatgacga atccgacaac    360
aaaatcatca catttggtga attactcaga aaagtttccc aaatcgctgg tgtcttaaaa    420
agctggggcg ttaagaaagg tgacacagtg gctatctatt tgccaatgat ccagaagcg     480
gtcattgcta tgttggctgt ggctcgtatt ggtgctattc actctgttgt ctttgctggg    540
ttctccgctg gttcgttgaa agatcgtgtc gttgacgcta attctaaagt ggtcatcact    600
tgtgatgaag gtaaagagg tggtaagacc atcaacacta aaaaaattgt tgacgaaggt     660
ttgaacggag tcgatttggt ttcccgtatc ttggttttcc aaagaactgg tactgaaggt    720
attccaatga aggccggtag agattactgg tggcatgagg aggccgctaa gcagagaact    780
tacctacctc ctgttttcatg tgacgctgaa gatcctctat ttttattata cattccggt     840
tccactggtt ctccaaaggg tgtcgttcac actacaggtg gttatttatt aggtgccgct    900
ttaacaacta gatacgtttt tgatattcac ccagaagatg ttctcttcac tgccggtgac    960
gtcggctgga tcacgggtca cacctatgct ctatatggtc cattaacctt gggtaccgcc    1020
tcaataattt tcgaatccac tcctgcctac ccagattatg gtagatattg gagaattatc    1080
caacgtcaca aggctaccca tttctatgtg gctccaactg ctttaagatt aatcaaacgt    1140
gtaggtgaag ccgaaattgc caaatatgac acttcctcat acgtgtcttt gggttccgtc    1200
ggtgaaccaa tctctccaga cttatgggaa tggtatcatg aaaaagtggg taacaaaaac    1260
tgtgtcattt gtgacactat gtggcaaaca gagtctggtt ctcatttaat tgctcctttg    1320
gcaggtgctg tcccaacaaa acctggttct gctaccgtgc cattcttgg tattaacgct    1380
tgtatcattg accctgttac aggtgtggaa ttagaaggta atgatgtcga aggtgtcctt    1440
gccgttaaat caccatggcc atcaatggct agatctgttt ggaaccacca cgaccgttac    1500
atggatactt acttgaaacc ttatcctggt cactatttca caggtgatgg tgctggtaga    1560
gatcatgatg gttactactg gatcaggggt agagttgacg acgttgtaaa tgtttccggt    1620
catagattat ccacatcaga aattgaagca tctatctcaa atcacgaaaa cgtctcggaa    1680
gctgctgttg tcggtattcc agatgaattg accggtcaaa ccgtcgttgc atatgttttcc   1740
ctaaaagatg gttatctaca aaacaacgct actgaaggtg atgcagaaca catcacacca    1800
gataatttac gtagagaatt gatcttacaa gttaggggtg agattggtcc tttcgcctca    1860
ccaaaaacca ttattctagt tagagatcta ccaagaacaa ggtcaggaaa gattatgaga    1920
agagttctaa gaaaggttgc ttctaacgaa gccgaacagc taggtgaccT aactactttg    1980
gccaacccag aagttgtacc tgccatcatt tctgctgtag agaaccaatt tttctctcaa    2040
aaaaagaaat aa                                                        2052
```

<210> SEQ ID NO 32
<211> LENGTH: 683
<212> TYPE: PRT
<213> ORGANISM: Saccharomyces cerevisiae

<400> SEQUENCE: 32

```
Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
```

```
                  50                  55                  60
Trp Asp Ala Pro Tyr Thr Lys Val Gln Ser Gly Ser Leu Asn Asn Gly
 65                  70                  75                  80

Asp Val Ala Trp Phe Leu Asn Gly Lys Leu Asn Ala Ser Tyr Asn Cys
                 85                  90                  95

Val Asp Arg His Ala Phe Ala Asn Pro Asp Lys Pro Ala Leu Ile Tyr
                100                 105                 110

Glu Ala Asp Asp Glu Ser Asp Asn Lys Ile Ile Thr Phe Gly Glu Leu
                115                 120                 125

Leu Arg Lys Val Ser Gln Ile Ala Gly Val Leu Lys Ser Trp Gly Val
130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
                180                 185                 190

Ala Asn Ser Lys Val Val Ile Thr Cys Asp Glu Gly Lys Arg Gly Gly
                195                 200                 205

Lys Thr Ile Asn Thr Lys Lys Ile Val Asp Glu Gly Leu Asn Gly Val
                210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
                260                 265                 270

Leu Phe Leu Leu Tyr Thr Ser Gly Ser Thr Gly Ser Pro Lys Gly Val
                275                 280                 285

Val His Thr Thr Gly Gly Tyr Leu Leu Gly Ala Ala Leu Thr Thr Arg
                290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
                340                 345                 350

Tyr Gly Arg Tyr Trp Arg Ile Ile Gln Arg His Lys Ala Thr His Phe
                355                 360                 365

Tyr Val Ala Pro Thr Ala Leu Arg Leu Ile Lys Arg Val Gly Glu Ala
                370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
                420                 425                 430

Gly Ser His Leu Ile Ala Pro Leu Ala Gly Ala Val Pro Thr Lys Pro
                435                 440                 445

Gly Ser Ala Thr Val Pro Phe Phe Gly Ile Asn Ala Cys Ile Ile Asp
                450                 455                 460

Pro Val Thr Gly Val Glu Leu Glu Gly Asn Asp Val Glu Gly Val Leu
465                 470                 475                 480
```

```
Ala Val Lys Ser Pro Trp Pro Ser Met Ala Arg Ser Val Trp Asn His
            485                 490                 495

His Asp Arg Tyr Met Asp Thr Tyr Leu Lys Pro Tyr Pro Gly His Tyr
        500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
        530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
        610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
            675                 680

<210> SEQ ID NO 33
<211> LENGTH: 157
<212> TYPE: DNA
<213> ORGANISM: Bacteriophage T5

<400> SEQUENCE: 33
ctataaaaat aggcgtatca cgaggcccct tcgtcttcac ctcgagaaat cataaaaat      60 ttatttgctt tgtgagcgga taacaattat aatagattca attgtgagcg gataacaatt    120
tcacacagaa ttcattaaag aggagaaatt aactcat                             157

<210> SEQ ID NO 34
<211> LENGTH: 253
<212> TYPE: DNA
<213> ORGANISM: Escherichia coli

<400> SEQUENCE: 34
tgacattaac ctataaaaat aggcgtatca cgaggcccct tgcgccgaat aaatacctgt     60
gacggaagat cacttcgcag aataaataaa tcctggtgtc cctgttgata ccggaagcc    120 ctgggccaac ttttggcgaa aatgagacgt tgatcggcac gtaagaggtt ccaactttca   180
ccataatgaa ataagatcac taccgggcgt attttttgag ttatcgagat tttcaggagc   240
taaggaagct aaa                                                      253

<210> SEQ ID NO 35
<211> LENGTH: 13669
<212> TYPE: DNA
<213> ORGANISM: Artificial Sequence
<220> FEATURE:
<223> OTHER INFORMATION: Plasmid

<400> SEQUENCE: 35
```

```
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc gccgcgaagc ggcgtcggct tgaacgaatt   240
gttagacatt atttgccgac taccttggtg atctcgcctt tcacgtagtg gacaaattct   300
tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
acatccttcg gcgcgatttt gccggttact gcgctgtacc aaatgcggga caacgtaagc   480
actacatttc gctcatcgcc agcccagtcg ggcggcgagt tccatagcgt taaggtttca   540
tttagcgcct caaatagatc ctgttcagga accggatcaa agagttcctc cgccgctgga   600
cctaccaagg caacgctatg ttctcttgct tttgtcagca agatagccag atcaatgtcg   660
atcgtggctg gctcgaagat acctgcaaga atgtcattgc gctgccattc tccaaattgc   720
agttcgcgct tagctggata cgccacggaa tgatgtcgt cgtgcacaac aatggtgact   780
tctacagcgc ggagaatctc gctctctcca ggggaagccg aagtttccaa aaggtcgttg   840
atcaaagctc gccgcgttgt ttcatcaagc cttacggtca ccgtaaccag caaatcaata   900
tcactgtgtg gcttcaggcc gccatccact gcggagccgt acaaatgtac ggccagcaac   960
gtcggttcga gatggcgctc gatgacgcca actacctctg atagttgagt cgatacttcg  1020
gcgatcaccg cttccctcat gatgtttaac tttgttttag ggcgactgcc ctgctgcgta  1080
acatcgttgc tgctccataa catcaaacat cgacccacgg cgtaacgcgc ttgctgcttg  1140
gatgcccgag gcatagactg taccccaaaa aaacagtcat aacaagccat gaaaaccgcc  1200
actgcgccgt taccaccgct gcgttcggtc aaggttctgg accagttgcg tgagcgcata  1260
cgctacttgc attacagctt acgaaccgaa caggcttatg tccactgggt tcgtgccttc  1320
atccgttttcc acggtgtgcg tcacccggca accttgggca gcagcgaagt cgaggcattt  1380
ctgtcctggc tggcgaacga gcgcaaggtt tcggtctcca cgcatcgtca ggcattggcg  1440
gccttgctgt tcttctacgg caaggtgctg tgcacggatc tgccctggct tcaggagatc  1500
ggaagacctc ggccgtcgcg gcgcttgccg gtggtgctga ccccggatga agtggttcgc  1560
atcctcggtt ttctggaagg cgagcatcgt ttgttcgccc agcttctgta tggaacgggc  1620
atgcggatca gtgagggttt gcaactgcgg gtcaaggatc tggatttcga tcacggcacg  1680
atcatcgtgc gggagggcaa gggctccaag gatcgggcct tgatgttacc cgagagcttg  1740
gcacccagcc tgcgcgagca ggggaattaa ttcccacggg ttttgctgcc cgcaaacggg  1800
ctgttctggt gttgctagtt tgttatcaga atcgcagatc cggcttcagc cggtttgccg  1860
gctgaaagcg ctatttcttc cagaattgcc atgatttttt ccccacggga ggcgtcactg  1920
gctcccgtgt tgtcggcagc tttgattcga taagcagcat cgcctgtttc aggctgtcta  1980
tgtgtgactg ttgagctgta acaagttgtc tcaggtgttc aatttcatgt tctagttgct  2040
ttgtttttact ggtttcacct gttctattag gtgttacatg ctgttcatct gttacattgt  2100
cgatctgttc atggtgaaca gctttgaatg caccaaaaac tcgtaaaagc tctgatgtat  2160
ctatcttttt tacaccgttt tcatctgtgc atatggacag ttttcccttt gatatgtaac  2220
ggtgaacagt tgttctactt tgtttgttta gtcttgatgc ttcactgata gatacaagag  2280
ccataagaac ctcagatcct tccgtattta gccagtatgt tctctagtgt ggttcgttgt  2340
ttttgcgtga gccatgagaa cgaaccattg agatcatact tactttgcat gtcactcaaa  2400
```

```
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
attttatct ggttgttctc aagttcggtt acgagatcca tttgtctatc tagttcaact    2580
tggaaaatca acgtatcagt cgggcggcct cgcttatcaa ccaccaattt catattgctg   2640
taagtgttta atctttact tattggtttc aaaacccatt ggttaagcct tttaaactca    2700
tggtagttat tttcaagcat taacatgaac ttaaattcat caaggctaat ctctatattt   2760
gccttgtgag ttttctttg tgttagttct tttaataacc actcataaat cctcatagag    2820
tatttgtttt caaaagactt aacatgttcc agattatatt ttatgaattt ttttaactgg   2880
aaaagataag gcaatatctc ttcactaaaa actaattcta attttcgct tgagaacttg    2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtgggggtt gagtagtgcc acacagcata aaattagctt ggtttcatgc  3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacctt    3360
gctggaaaac ttgtaaattc tgctagaccc tctgtaaatt ccgctagacc tttgtgtgtt   3420
tttttgttt atattcaagt ggttataatt tatagaataa agaagaata aaaaagata     3480
aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttcgtga cattcagttc gctgcgctca cggctctggc    3720
agtgaatggg ggtaaatggc actacaggcg cctttttatgg attcatgcaa ggaaactacc  3780
cataatacaa gaaaagcccg tcacgggctt tcagggcgt tttatggcgg gtctgctatg    3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgccttga caatgccaca tcctgagcaa ataattcaac cactaaacaa    4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaa    4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
```

```
atgccggcgc catcaatgag ctgtgctggg ggctggagga gcaggggtc  cctgccaga   4860
ccataaccta tgacggaggc ggtgacgccg ctgcgctggg cgccctggcg gccagaagct   4920
cgccctgcg  ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gcccgtcaa  tcaggacggg ctgattggcg agtggcctga agaggggctg atcgccatgg   6000
acagccccct tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggacccc  tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc acctgatgc   6960
agatgctgcc gggcaccgac tttatttct  ccggctacag cgccggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga gcggaaaacc attgccattc   7140
gccagaaagc ggcgcgggcg atccaggcgg ttttccgcga gctggggctg ccgccaatcg   7200
```

```
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agcaacccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc    7800 gcattctgcg cacgtccgac gtctcccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccggcgggg tgggcgttgg    8940 cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccgggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
```

```
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca agtggtgta catcaaggag ggcgaactgg tgccgatcga    10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380 gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagagtac tggcgaaagg gggatgtgct gcaaggcgat taagttgggt aacgccaggg   10560
ttttcccagt cacgacgttg taaaacgacg gccagtgaat tcgagctcgg tacccggggc   10620
ggccgcgcta gcgcccgatc cagctggagt ttgtagaaac gcaaaaaggc catccgtcag   10680
gatggccttc tgcttaattt gatgcctggc agtttatggc gggcgtcctg cccgccaccc   10740
tccgggccgt tgcttcgcaa cgttcaaatc cgctcccggc ggatttgtcc tactcaggag   10800
agcgttcacc gacaaacaac agataaaacg aaaggcccag tctttcgact gagcctttcg   10860
ttttatttga tgcctggcag ttccctactc tcgcatgggg agaccccaca ctaccatcgg   10920
cgctacggcg tttcacttct gagttcggca tggggtcagg tgggaccacc gcgctactgc   10980
cgccaggcaa attctgtttt atcagaccgc ttctgcgttc tgatttaatc tgtatcaggc   11040
tgaaaatctt ctctcatccg ccaaaacagc caagcttgca tgcctgcagc ccgggttacc   11100
atttcaacag atcgtcctta gcatataagt agtcgtcaaa aatgaattca acttcgtctg   11160
tttcggcatt gtagccgcca actctgatgg attcgtggtt tttgacaatg atgtcacagc   11220 cttttttcctt taggaagtcc aagtcgaaag tagtggcaat accaatgatc ttacaaccgg   11280
cggcttttcc ggcggcaata cctgctggag cgtcttcaaa tactactacc ttagatttgg   11340
aagggtcttg ctcattgatc ggatatccta agccattcct gcccttcaga tatggttctg   11400
gatgaggctt accctgtttg acatcattag cggtaatgaa gtactttggt ctcctgattc   11460
ccagatgctc gaaccatttt tgtgccatat cacgggtacc ggaagttgcc acagcccatt   11520
tctcttttgg tagagcgttc aaagcgttgc acagcttaac tgcacctggg acttcaatgg   11580
atttttcacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggttttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggtcttcat tgggtagttg    11940 ttgtaaacga tttggtatac ggcttcaaat aatgggaagt cttcgacaga gccacatgtt   12000
```

```
tccaaccatt cgtgaacttc tttgcaggta attaaacctt gagcggattg gccattcaac   12060 aactccttt  cacattccca ggcgtcctta ccagaagtag ccattagcct agcaaccttg   12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttaccccagc ctagaccttc gacgaaacca   12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt tagcaccaac ttcaaaaccc   12600
tttagacagg agatagctct gacgtgtgaa tcaacatgac ctttcaattg ctacagata   12660 cggggcaaaa attgatgtgg aatgttaaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaacctt gaaaggcttt   12960
tcggcagcct tcaaagaaac agaagaggaa cttctctttc taccagcatt caagtggccg   13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgacacg aattatgcag tgatttacga   13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tccccctttc gccagctggc gtaatagcga agaggcccgc accgatcgcc   13500
cttcccaaca gttgcgcagc ctgaatgcg aatggcgcct gatgcggtat tttctcctta   13560
cgcatctgtg cggtatttca caccgcatat ggtgcactct cagtacaatc tgctctgatg   13620
ccgcatagtt aagccagccc cgacacccgc caacacccgc tgacgagct                13669
```

<210> SEQ ID NO 36
<211> LENGTH: 13543
<212> TYPE: DNA
<213> ORGANISM: Artificial Sequence
<220> FEATURE:
<223> OTHER INFORMATION: Plasmid

<400> SEQUENCE: 36

```
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc ccgcgaagc ggcgtcggct tgaacgaatt   240
gttagacatt atttgccgac taccttggtg atctcgcctt tcacgtagtg acaaattct   300 tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
```

-continued

```
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacgtcca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatctttt tacaccgttt tcatctgtgc atatggacag ttttccctt gatatgtaac     2220
ggtgaacagt tgttctactt tgtttgtta gtcttgatgc ttcactgata gatacaagag    2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttctttg tgttagttct tttaataacc actcataaat cctcatagag    2820
```

```
tatttgtttt caaaagactt aacatgttcc agattatatt ttatgaattt ttttaactgg    2880
aaaagataag gcaatatctc ttcactaaaa actaattcta attttttcgct tgagaacttg   2940 gcatagtttg tccactggaa aatctcaaag cctttaacca aaggattcct gatttccaca   3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtccttt cctttgagtt gtgggtatct gtaaattctg ctagaccttt     3360
gctggaaaac ttgtaaattc tgctagaccc tctgtaaatt ccgctagacc tttgtgtgtt    3420
ttttttgttt atattcaagt ggttataatt tatagaataa agaaagaata aaaaaagata    3480
aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat    3660
caggcacctg agtcgctgtc ttttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc     3900
acttcggatt atcccgtgac aggtcattca gactggctaa tgcacccagt aaggcagcgg   3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga ctatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800 atgccgcgc catcaatgag ctgtgctggg ggctggagga gcaggggtc ccctgccaga     4860 ccataaccta tgacggaggc ggtgacgccg ctgcgctggg cgcccctggcg gccagaaagct 4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacgcggca    5160 gccgcatcga gaaagaccat attcgcgtcg aggcctacgg caccgtcgat gaactgatat   5220
```

```
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc tttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga ctatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agagggctg atcgccatgg     6000 acagccccttt gacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga     6300 tgcgtgcccg ccggaccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcggtcacc ggcgattacc tgcagacctc ggccattctc gatcggcagt     7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
```

```
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccgcggcgc agtatgccga   9000 ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg catccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tgtgggcgg   9780 cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
```

```
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620
ttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgtttttca cattccacat caattttttgc   11160 cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt aattacctg caaagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctgggaatca ggagaccaaa gtacttcatt accgctaatg atgtcaaaca gggtaagcct   12420
```

```
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt catttttgac gactacttat atgctaagga cgatctgttg   12720
aaatggtaac ccgggctgca ggcatgcaag cttggctgtt ttggcggatg agagaagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
aaaacgaaag gctcagtcga aagactgggc ctttcgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta agcagaaggc   13140
catcctgacg gatggccttt ttgcgtttct acaaactcca gctggatcgg cgctagagt    13200 atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                    13543

<210> SEQ ID NO 37
<211> LENGTH: 13543
<212> TYPE: DNA
<213> ORGANISM: Artificial Sequence
<220> FEATURE:
<223> OTHER INFORMATION: Plasmid

<400> SEQUENCE: 37
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
```

```
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctgaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160 ctatctttt tacaccgttt tcatctgtgc atatggacag ttttcccttt gatatgtaac   2220
ggtgaacagt tgttctactt tgttttgtta gtccttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaagacttt aacatgttcc agattatatt ttatgaattt ttttaactgg   2880
aaaagataag gcaatatctc ttcactaaaa actaattcta attttcgct tgagaacttg   2940 gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
```

```
gctggaaaac ttgtaaattc tgctagaccc tctgtaaatt ccgctagacc tttgtgtgtt    3420 tttttttgttt atattcaagt ggttataatt tatagaataa agaaagaata aaaaagata    3480 aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc     3720
agtgaatggg ggtaaatggc actacaggcg cctttatgg attcatgcaa ggaaactacc     3780
cataatacaa gaaaagcccg tcacgggctt ctcagggcgt tttatggcgg gtctgctatg    3840
tggtgctatc tgacttttg ctgttcagca gttcctgccc tctgattttc agtctgacc      3900 acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcagggggtc ccctgccaga    4860
ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640 tagcaaaacac agaaaaaagc ccgcacctga cagtgcgggc tttttttttc ctaggcgatc   5700
tgtgctgttt gccacggtat gcagcaccag cgcgagatta tgggctcgca cgctcgactg    5760
```

```
tcggacgggg gcactggaac gagaagtcag gcgagccgtc acgcccttga caatgccaca      5820
tcctgagcaa ataattcaac cactaaacaa atcaaccgcg tttcccggag gtaaccaagc      5880 ttcaccttttt gagccgatga acaatgaaaa gatcaaaacg atttgcagta ctggcccagc     5940
gccccgtcaa tcaggacggg ctgattggcg agtggcctga agaggggctg atcgccatgg      6000 acagccccttt tgacccggtc tcttcagtaa aagtggacaa cggtctgatc gtcgaactgg    6060
acggcaaacg ccgggaccag tttgacatga tcgaccgatt tatcgccgat tacgcgatca     6120
acgttgagcg cacagagcag gcaatgcgcc tggaggcggt ggaaatagcc cgtatgctgg      6180
tggatattca cgtcagccgg gaggagatca ttgccatcac taccgccatc acgccggcca     6240
aagcggtcga ggtgatggcg cagatgaacg tggtggagat gatgatgcg ctgcagaaga      6300 tgcgtgcccg ccggacccc tccaaccagt gccacgtcac caatctcaaa gataatccgg      6360
tgcagattgc cgctgacgcc gccgaggccg ggatccgcgg cttctcagaa caggagacca     6420
cggtcggtat cgcgcgctac gcgccgttta acgccctggc gctgttggtc ggttcgcagt     6480
gcggccgccc cggcgtgttg acgcagtgct cggtggaaga ggccaccgag ctggagctgg     6540
gcatgcgtgg cttaaccagc tacgccgaga cggtgtcggt ctacggcacc gaagcggtat     6600
ttaccgacgg cgatgatacg ccgtggtcaa aggcgttcct cgcctcggcc tacgcctccc     6660
gcgggttgaa aatgcgctac acctccggca ccggatccga agcgctgatg gctattcgg      6720 agagcaagtc gatgctctac ctcgaatcgc gctgcatctt cattactaaa ggcgccgggg     6780
ttcagggact gcaaaacggc gcggtgagct gtatcggcat gaccggcgct gtgccgtcgg     6840
gcattcgggc ggtgctggcg gaaaacctga tcgcctctat gctcgacctc gaagtggcgt     6900
ccgccaacga ccagactttc tcccactcgg atattcgccg caccgcgcgc accctgatgc     6960
agatgctgcc gggcaccgac tttatttttct ccggctacag cgcggtgccg aactacgaca    7020
acatgttcgc cggctcgaac ttcgatgcgg aagattttga tgattacaac atcctgcagc     7080
gtgacctgat ggttgacggc ggcctgcgtc cggtgaccga ggcggaaacc attgccattc     7140
gccagaaagc ggcgcgggcg atccaggcgg ttttccgcga gctggggctg ccgccaatcg     7200
ccgacgagga ggtggaggcc gccacctacg cgcacggcag caacgagatg ccgccgcgta     7260
acgtggtgga ggatctgagt gcggtggaag agatgatgaa gcgcaacatc accgcctcg     7320 atattgtcgg cgcgctgagc cgcagcggct ttgaggatat cgccagcaat attctcaata     7380
tgctgcgcca gcgggtcacc ggcgattacc tgcagacctc ggccattctc gatcggcagt     7440
tcgaggtggt gagtgcggtc aacgacatca atgactatca ggggccgggc accggctatc     7500
gcatctctgc cgaacgctgg gcggagatca aaaatattcc gggcgtggtt cagcccgaca     7560
ccattgaata aggcggtatt cctgtgcaac agacaaccca aattcagccc tcttttaccc     7620
tgaaaacccg cgagggcggg gtagcttctg ccgatgaacg cgccgatgaa gtggtgatcg     7680
gcgtcggccc tgccttcgat aaacaccagc atcacactct gatcgatatg ccccatggcg     7740
cgatcctcaa agagctgatt gccggggtgg aagaagaggg gcttcacgcc cgggtggtgc     7800
gcattctgcg cacgtccgac gtctccttta tggcctggga tgcggccaac ctgagcggct     7860
cggggatcgg catcggtatc cagtcgaagg ggaccacggt catccatcag cgcgatctgc     7920
tgccgctcag caacctggag ctgttctccc aggcgccgct gctgacgctg agacctacc     7980 ggcagattgg caaaaacgct gcgcgctatg cgcgcaaaga gtcaccttcg ccggtgccgg      8040
tggtgaacga tcagatggtg cggccgaaat ttatggccaa agccgcgcta tttcatatca     8100
aagagaccaa acatgtggtg caggacgccg agcccgtcac cctgcacatc gacttagtaa     8160
```

```
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gaggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca agtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagcgtgc accaatgctt ctggcgtcag gcagccatcg gaagctgtgg tatggctgtg  10560
```

```
caggtcgtaa atcactgcat aattcgtgtc gctcaaggcg cactcccgtt ctggataatg    10620
ttttttgcgc cgacatcata acggttctgg caaatattct gaaatgagct gttgacaatt    10680
aatcatccgg ctcgtataat gtgtggaatt gtgagcggat aacaatttca cacaggaaac    10740
agaccatgac tagtaaggag gacaattcca tggctgctgc tgctgataga ttaaacttaa    10800
cttccggcca cttgaatgct ggtagaaaga gaagttcctc ttctgttcct ttgaaggctg    10860
ccgaaaagcc tttcaaggtt actgtgattg gatctggtaa ctggggtact actattgcca    10920
aggtggttgc cgaaaattgt aagggatacc cagaagtttt cgctccaata gtacaaatgt    10980
gggtgttcga agaagagatc aatggtgaaa aattgactga aatcataaat actagacatc    11040
aaaacgtgaa atacttgcct ggcatcactc tacccgacaa tttggttgct aatccagact    11100
tgattgattc agtcaaggat gtcgacatca tcgtttttcaa cattccacat caattttttgc    11160 cccgtatctg tagccaattg aaaggtcatg ttgattcaca cgtcagagct atctcctgtc    11220
taaagggttt tgaagttggt gctaaaggtg tccaattgct atcctcttac atcactgagg    11280
aactaggtat tcaatgtggt gctctatctg gtgctaacat tgccaccgaa gtcgctcaag    11340
aacactggtc tgaaacaaca gttgcttacc acattccaaa ggatttcaga ggcgagggca    11400
aggacgtcga ccataaggtt ctaaaggcct tgttccacag accttacttc cacgttagtg    11460
tcatcgaaga tgttgctggt atctccatct gtggtgcttt gaagaacgtt gttgccttag    11520
gttgtggttt cgtcgaaggt ctaggctggg gtaacaacgc ttctgctgcc atccaaagag    11580
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660 gaaacgacg aagttgaatt cattttttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
```

| | | | | |
|---|---|---|---|---|
| aaaacgaaag | gctcagtcga | aagactgggc | ctttcgtttt | atctgttgtt | tgtcggtgaa | 13020 |
| cgctctcctg | agtaggacaa | atccgccggg | agcggatttg | aacgttgcga | agcaacggcc | 13080 |
| cggagggtgg | cgggcaggac | gcccgccata | aactgccagg | catcaaatta | agcagaaggc | 13140 |
| catcctgacg | gatggccttt | ttgcgtttct | acaaactcca | gctggatcgg | gcgctagagt | 13200 |
| atacatttaa | atggtaccct | ctagtcaagg | ccttaagtga | gtcgtattac | ggactggccg | 13260 |
| tcgttttaca | acgtcgtgac | tgggaaaacc | ctggcgttac | ccaacttaat | cgccttgcag | 13320 |
| cacatccccc | tttcgccagc | tggcgtaata | gcgaagaggc | ccgcaccgat | cgcccttccc | 13380 |
| aacagttgcg | cagcctgaat | ggcgaatggc | gcctgatgcg | gtattttctc | cttacgcatc | 13440 |
| tgtgcggtat | ttcacaccgc | atatggtgca | ctctcagtac | aatctgctct | gatgccgcat | 13500 |
| agttaagcca | gccccgacac | ccgccaacac | ccgctgacga | gct | | 13543 |

<210> SEQ ID NO 38
<211> LENGTH: 13402
<212> TYPE: DNA
<213> ORGANISM: Artificial Sequence
<220> FEATURE:
<223> OTHER INFORMATION: Plamid

<400> SEQUENCE: 38

| | | | | | | |
|---|---|---|---|---|---|---|
| tagtaaagcc | ctcgctagat | tttaatgcgg | atgttgcgat | tacttcgcca | actattgcga | 60 |
| taacaagaaa | aagccagcct | ttcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |
| tccaactgat | ctgcgcgcga | ggccaagcga | tcttcttctt | gtccaagata | agcctgtcta | 360 |
| gcttcaagta | tgacgggctg | atactgggcc | ggcaggcgct | ccattgccca | gtcggcagcg | 420 |
| acatccttcg | gcgcgatttt | gccggttact | gcgctgtacc | aaatgcggga | caacgtaagc | 480 |
| actacatttc | gctcatcgcc | agcccagtcg | ggcggcgagt | tccatagcgt | taaggtttca | 540 |
| tttagcgcct | caaatagatc | ctgttcagga | accggatcaa | agagttcctc | cgccgctgga | 600 |
| cctaccaagg | caacgctatg | ttctcttgct | tttgtcagca | agatagccag | atcaatgtcg | 660 |
| atcgtggctg | gctcgaagat | acctgcaaga | atgtcattgc | gctgccattc | tccaaattgc | 720 |
| agttcgcgct | tagctggata | acgccacgga | atgatgtcgt | cgtgcacaac | aatggtgact | 780 |
| tctacagcgc | ggagaatctc | gctctctcca | ggggaagccg | aagtttccaa | aaggtcgttg | 840 |
| atcaaagctc | gccgcgttgt | ttcatcaagc | cttacggtca | ccgtaaccag | caaatcaata | 900 |
| tcactgtgtg | gcttcaggcc | gccatccact | gcggagccgt | acaaatgtac | ggccagcaac | 960 |
| gtcggttcga | gatggcgctc | gatgacgcca | actacctctg | atagttgagt | cgatacttcg | 1020 |
| gcgatcaccg | cttccctcat | gatgtttaac | tttgttttag | ggcgactgcc | ctgctgcgta | 1080 |
| acatcgttgc | tgctccataa | catcaaacat | cgacccacgg | cgtaacgcgc | ttgctgcttg | 1140 |
| gatgcccgag | gcatagactg | taccccaaaa | aaacagtcat | aacaagccat | gaaaaccgcc | 1200 |
| actgcgccgt | taccaccgct | gcgttcggtc | aaggttctgg | accagttgcg | tgagcgcata | 1260 |
| cgctacttgc | attacagctt | acgaaccgaa | caggcttatg | tccactgggt | tcgtgccttc | 1320 |
| atccgtttcc | acggtgtgcg | tcacccggca | accttgggca | gcagcgaagt | cgaggcattt | 1380 |
| ctgtcctggc | tggcgaacga | gcgcaaggtt | tcggtctcca | cgcatcgtca | ggcattggcg | 1440 |
| gccttgctgt | tcttctacgg | caaggtgctg | tgcacggatc | tgccctggct | tcaggagatc | 1500 |

```
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttttcgct tgagaacttg   2940 gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgatttttaa tcactatacc aattgagatg ggctagtcaa   3300
tgataattac tagtcctttt cctttgagtt gtgggtatct gtaaattctg ctagacccttt   3360 gctggaaaac ttgtaaattc tgctagaccc tctgtaaatt ccgctagacc tttgtgtgtt   3420 tttttttgttt atattcaagt ggttataatt tatagaataa agaaagaata aaaaagata   3480 aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg cctttttatgg attcatgcaa ggaaactacc   3780
cataatacaa gaaaagcccg tcacgggctt ctcagggcgt tttatggcgg gtctgctatg   3840
tggtgctatc tgacttttg ctgttcagca gttcctgccc tctgatttcc cagtctgacc   3900
```

```
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860
ccataaccta tgacggaggc ggtgacgccg ctgcgctggg cgccctggcg ccagaagct    4920
cgccctgcg gtgggtatc gggctcagcg cgtccggcga gatagccctc actcatgccc    4980
agctgccggc ggacgcgccg ctggctaccg gacacgtcac cgatagcgac gatcaactgc    5040
gtacgctcgc cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttcccggagg taaccaagct tcacctttg agccgatgaa    5760
caatgaaaag atcaaaacga tttgcagtac tggcccagcg ccccgtcaat caggacgggc    5820
tgattggcga gtggcctgaa gagggctga tcgccatgga cagccccttt gacccggtct    5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc ggacccccct    6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
```

```
cgccgtttaa cgccctggcg ctgttggtcg gttcgcagtg cggccgcccc ggcgtgttga   6360
cgcagtgctc ggtggaagag gccaccgagc tggagctggg catgcgtggc ttaaccagct   6420
acgccgagac ggtgtcggtc tacgcaccg aagcggtatt taccgacggc gatgatacgc    6480
cgtggtcaaa ggcgttcctc gcctcggcct acgcctcccg cgggttgaaa atgcgctaca   6540
cctccggcac cggatccgaa cgctgatgg gctattcgga gagcaagtcg atgctctacc    6600
tcgaatcgcg ctgcatcttc attactaaag gcgccggggt tcagggactg caaaacggcg   6660
cggtgagctg tatcggcatg accggcgctg tgccgtcggg cattcgggcg gtgctggcgg   6720
aaaacctgat cgcctctatg ctcgacctcg aagtggcgtc cgccaacgac cagactttct   6780
cccactcgga tattgccgc accgcgcgca ccctgatgca gatgctgccg ggcaccgact    6840
ttattttctc cggctacagc gcggtgccga actacgacaa catgttcgcc ggctcgaact   6900
tcgatgcgga agattttgat gattacaaca tcctgcagcg tgacctgatg gttgacggcg   6960
gcctgcgtcc ggtgaccgag gcggaaacca ttgccattcg ccagaaagcg gcgcgggcga   7020
tccaggcggt tttccgcgag ctggggctgc cgccaatcgc cgacgaggag gtggaggccg   7080
ccacctacgc gcacggcagc aacgagatgc cgccgcgtaa cgtggtggag gatctgagtg   7140
cggtggaaga gatgatgaag cgcaacatca ccggcctcga tattgtcggc gcgctgagcc   7200
gcagcggctt tgaggatatc gccagcaata ttctcaatat gctgcgccag cgggtcaccg   7260
gcgattacct gcagacctcg gccattctcg atcggcagtt cgaggtggtg agtgcggtca   7320
acgacatcaa tgactatcag gggccgggca ccggctatcg catctctgcc gaacgctggg   7380
cggagatcaa aaatattccg ggcgtggttc agcccgacac cattgaataa ggcggtattc   7440
ctgtgcaaca gacaacccaa attcagccct cttttaccct gaaaacccgc gagggcgggg   7500
tagcttctgc cgatgaacgc gccgatgaag tggtgatcgg cgtcggccct gccttcgata   7560
aacaccagca tcacactctg atcgatatgc cccatggcgc gatcctcaaa gagctgattg   7620
ccggggtgga agaagagggg cttcacgccc gggtggtgcg cattctgcgc acgtccgacg   7680
tctcctttat ggcctgggat gcggccaacc tgagcggctc ggggatcggc atcggtatcc   7740
agtcgaaggg gaccacggtc atccatcagc gcgatctgct gccgctcagc aacctggagc   7800
tgttctccca ggcgccgctg ctgacgctgg agacctaccg gcagattggc aaaaacgctg   7860
cgcgctatgc gcgcaaagag tcaccttcgc cggtgccggt ggtgaacgat cagatggtgc   7920
ggccgaaatt tatggccaaa gccgcgctat ttcatatcaa agagaccaaa catgtggtgc   7980
aggacgccga gcccgtcacc ctgcacatcg acttagtaag ggagtgacca tgagcgagaa   8040
aaccatgcgc gtgcaggatt atccgttagc caccgctgc ccggagcata tcctgacgcc    8100
taccggcaaa ccattgaccg atattaccct cgagaaggtg ctctctggcg aggtgggccc   8160
gcaggatgtg cggatctccc gccagaccct tgagtaccag gcgcagattg ccgagcagat   8220
gcagcgccat gcggtggcgc gcaatttccg ccgcgcggcg gagcttatcg ccattcctga   8280
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggc acgcgggaca atatcgccgg gaccctcgcc gcgctggagc aggccctggc   8640
gaaaacaccg tggtcgatga gcgatgtctc tcgcatctat cttaacgaag ccgcgccggt   8700
```

```
gattggcgat gtggcgatgg agaccatcac cgagaccatt atcaccgaat cgaccatgat    8760
cggtcataac ccgcagacgc cgggcggggt gggcgttggc gtggggacga ctatcgccct    8820
cgggcggctg cgacgctgc cggcggcgca gtatgccgag gggtggatcg tactgattga    8880
cgacgccgtc gatttccttg acgccgtgtg gtggctcaat gaggcgctcg accgggggat    8940
caacgtggtg gcggcgatcc tcaaaaagga cgacggcgtg ctggtgaaca accgcctgcg    9000
taaaccctg ccggtggtgg atgaagtgac gctgctggag caggtccccg aggggtaat    9060
ggcggcggtg gaagtggccg cgccgggcca ggtggtgcgg atcctgtcga atccctacgg    9120
gatcgccacc ttcttcgggc taagcccgga agagacccag gccatcgtcc ccatcgcccg    9180
cgccctgatt ggcaaccgtt ccgcggtggt gctcaagacc ccgcagggg atgtgcagtc    9240
gcgggtgatc ccggcgggca acctctacat tagcggcgaa aagcgccgcg agaggccga    9300
tgtcgccgag ggcgcggaag ccatcatgca ggcgatgagc gcctgcgctc cggtacgcga    9360
catccgcggc gaaccgggca cccacgccgg cggcatgctt gagcgggtgc gcaaggtaat    9420
ggcgtccctg accggccatg agatgagcgc gatatacatc caggatctgc tggcggtgga    9480
tacgtttatt ccgcgcaagg tgcagggcgg gatggccggc gagtgcgcca tggagaatgc    9540
cgtcgggatg gcggcgatgg tgaaagcgga tcgtctgcaa atgcaggtta tcgcccgcga    9600
actgagcgcc cgactgcaga ccgaggtggt ggtgggcggc gtggaggcca acatggccat    9660
cgccggggcg ttaaccactc ccggctgtgc ggcgccgctg gcgatcctcg acctcggcgc    9720
cggctcgacg gatgcggcga tcgtcaacgc ggaggggcag ataacggcgg tccatctcgc    9780
cggggcgggg aatatggtca gcctgttgat taaaaccgag ctgggcctcg aggatctttc    9840
gctggcggaa gcgataaaaa aatacccgct ggccaaagtg gaaagcctgt tcagtattcg    9900
tcacgagaat ggcgcggtgg agttctttcg ggaagccctc agcccggcgg tgttcgccaa    9960
agtggtgtac atcaaggagg gcgaactggt gccgatcgat aacgccagcc cgctggaaaa   10020
aattcgtctc gtgcgccggc aggcgaaaga gaaagtgttt gtcaccaact gcctgcgcgc   10080
gctgcgccag gtctcacccg gcggttccat tcgcgatatc gcctttgtgg tgctggtggg   10140
cggctcatcg ctggactttg agatcccgca gcttatcacg gaagccttgt cgcactatgg   10200
cgtggtcgcc gggcagggca atattcgggg aacagaaggg ccgcgcaatg cggtcgccac   10260
cgggctgcta ctggccggtc aggcgaatta acgggcgct cgcgccagcc tctaggtaca   10320
aataaaaaag gcacgtcaga tgacgtgcct ttttcttgt ctagcgtgca ccaatgcttc   10380
tggcgtcagg cagccatcgg aagctgtggt atggctgtgc aggtcgtaaa tcactgcata   10440
attcgtgtcg ctcaaggcgc actcccgttc tggataatgt ttttttgcgcc gacatcataa   10500
cggttctggc aaatattctg aaatgagctg ttgacaatta atcatccggc tcgtataatg   10560
tgtggaattg tgagcggata acaatttcac acaggaaaca gaccatgact agtaaggagg   10620
acaattccat ggctgctgct gctgatagat taaacttaac ttccggccac ttgaatgctg   10680
gtagaaagag aagttcctct tctgtttctt tgaaggctgc cgaaaagcct ttcaaggtta   10740
ctgtgattgg atctggtaac tggggtacta ctattgccaa ggtggttgcc gaaaattgta   10800
agggataccc agaagttttc gctccaatag tacaaatgtg ggtgttcgaa gaagagatca   10860
atggtgaaaa attgactgaa atcataaata ctagacatca aaacgtgaaa tacttgcctg   10920
gcatcactct acccgacaat ttggttgcta atccagactt gattgattca gtcaaggatg   10980
tcgacatcat cgtttttcaac attccacatc aattttttgcc ccgtatctgt agccaattga   11040
aaggtcatgt tgattcacac gtcagagcta tctcctgtct aaagggtttt gaagttggtg   11100
```

```
ctaaaggtgt ccaattgcta tcctcttaca tcactgagga actaggtatt caatgtggtg   11160
ctctatctgg tgctaacatt gccaccgaag tcgctcaaga acactggtct gaaacaacag   11220
ttgcttacca cattccaaag gatttcagag gcgagggcaa ggacgtcgac cataaggttc   11280
taaaggcctt gttccacaga ccttacttcc acgttagtgt catcgaagat gttgctggta   11340
tctccatctg tggtgctttg aagaacgttg ttgccttagg ttgtggtttc gtcgaaggtc   11400
taggctgggg taacaacgct tctgctgcca tccaaagagt cggtttgggt gagatcatca   11460
gattcggtca aatgttttc ccagaatcta gagaagaaac atactaccaa gagtctgctg   11520
gtgttgctga tttgatcacc acctgcgctg gtggtagaaa cgtcaaggtt gctaggctaa   11580
tggctacttc tggtaaggac gcctgggaat gtgaaaagga gttgttgaat ggccaatccg   11640
ctcaaggttt aattacctgc aaagaagttc acgaatggtt ggaaacatgt ggctctgtcg   11700
aagacttccc attatttgaa gccgtatacc aaatcgttta caacaactac ccaatgaaga   11760
acctgccgga catgattgaa gaattagatc tacatgaaga ttagatttat tggatccagg   11820
aaacagacta gaattatggg attgactact aaacctctat ctttgaaagt taacgccgct   11880
ttgttcgacg tcgacggtac cattatcatc tctcaaccag ccattgctgc attctggagg   11940
gatttcggta aggacaaacc ttatttcgat gctgaacacg ttatccaagt ctcgcatggt   12000
tggagaacgt ttgatgccat tgctaagttc gctccagact ttgccaatga agagtatgtt   12060
aacaaattag aagctgaaat tccggtcaag tacggtgaaa aatccattga agtcccaggt   12120
gcagttaagc tgtgcaacgc tttgaacgct ctaccaaaag agaaatgggc tgtggcaact   12180
tccggtaccc gtgatatggc acaaaaatgg ttcgagcatc tgggaatcag gagaccaaag   12240
tacttcatta ccgctaatga tgtcaaacag ggtaagcctc atccagaacc atatctgaag   12300
ggcaggaatg gcttaggata tccgatcaat gagcaagacc cttccaaatc taaggtagta   12360
gtatttgaag acgctccagc aggtattgcc gccggaaaag ccgccggttg taagatcatt   12420
ggtattgcca ctactttcga cttggacttc ctaaaggaaa aaggctgtga catcattgtc   12480
aaaaaccacg aatccatcag agttggcggc tacaatgccg aaacagacga agttgaattc   12540
atttttgacg actacttata tgctaaggac gatctgttga aatggtaacc cgggctgcag   12600
gcatgcaagc ttggctgttt tggcggatga gagaagattt tcagcctgat acagattaaa   12660
tcagaacgca gaagcggtct gataaaacag aatttgcctg gcggcagtag cgcggtggtc   12720
ccacctgacc ccatgccgaa ctcagaagtg aaacgccgta gcgccgatgg tagtgtgggg   12780
tctccccatg cgagagtagg gaactgccag gcatcaaata aaacgaaagg ctcagtcgaa   12840
agactgggcc tttcgtttta tctgttgttt gtcggtgaac gctctcctga gtaggacaaa   12900
tccgccggga gcggatttga acgttgcgaa gcaacggccc ggagggtggc gggcaggacg   12960
cccgccataa actgccaggc atcaaattaa gcagaaggcc atcctgacgg atggcctttt   13020
tgcgtttcta caaactccag ctggatcggg cgctagagta tacatttaaa tggtaccctc   13080
tagtcaaggc cttaagtgag tcgtattacg gactggccgt cgttttacaa cgtcgtgact   13140
gggaaaaccc tggcgttacc caacttaatc gccttgcagc acatccccct ttcgccagct   13200
ggcgtaatag cgaagaggcc cgcaccgatc gcccttccca acagttgcgc agcctgaatg   13260
gcgaatggcg cctgatgcgg tattttctcc ttacgcatct gtgcggtatt tcacaccgca   13320
tatggtgcac tctcagtaca atctgctctg atgccgcata gttaagccag ccccgacacc   13380
cgccaacacc cgctgacgag ct                                            13402
```

```
<210> SEQ ID NO 39
<211> LENGTH: 14443
<212> TYPE: DNA
<213> ORGANISM: Artificial Sequence
<220> FEATURE:
<223> OTHER INFORMATION: Plasmid

<400> SEQUENCE: 39
ttctgataac aaactagcaa caccagaaca gcccgtttgc gggcagcaaa acccgtggga      60
attaattccc ctgctcgcgc aggctgggtg ccaagctctc gggtaacatc aaggcccgat     120
ccttggagcc cttcttacag agatgaaaaa caaaccgcga cgccaggcgg catcgcggtc     180
tcagagatat gtttacgtag atcgaagagc accggtgttt aaacgccctt gacgatgcca     240
catcctgagc aaataattca accactaaac aaatcaaccg cgtttcccgg aggtaaccga     300
gctcatgatc ctgtgttgtg gtgaagccct gatcgacatg ctgccccggc agacgacgct     360
gggtgaggcg ggctttgccc cttacgcagg cggagcggtc ttcaacacgg caattgcgct     420
ggggcgtctt ggcgtccctt cagcctttt taccggtctt ccgacgaca tgatgggcga     480 tatcctgcgg gagaccctgc gggccagcaa ggtggatttc agctattgcg ccaccctgtc     540
gcgccccacc accattgcgt tcgttaagct ggttgatggc catgcgacct acgctttta     600 cgacgagaac accgccggcc ggatgatcac cgaggccgaa cttccggcct gggagcgga     660 ttgcgaagcg ctgcatttcg gcgccatcag ccttattccc gaaccctgcg gcagcaccta     720
tgaggcgctg atgacgcgcg agcatgagac ccgcgtcatc tcgctcgatc gaacattcg     780 tcccggcttc atccagaaca agcagtcgca catggcccgc atccgccgca tggcggcgat     840
gtctgacatc gtcaagttct cggatgagga cctggcgtgg ttcggtctgg aaggcgacga     900
ggacacgctt gcccgccact ggctgcacca cggtgcaaaa ctcgtcgttg tcacccgtgg     960
cgccaagggt gccgtggggtt acagcgccaa tctcaaggtg gaagtggcct ccgagcgcgt    1020
cgaagtggtc gatacggtcg cgccggcga tacgttcgat gccggcattc ttgcttcgct    1080
gaaaatgcag ggcctgctga ccaaagcgca ggtggcttcg ctgagcgaag agcagatcag    1140
aaaagctttg gcgcttggcg cgaaagccgc tgcggtcact gtctcgcggg ctggcgcaaa    1200
tccgcctttc gcgcatgaaa tcggtttgtg attaattaaa gcacgcagtc aaacaaaaaa    1260
cccgcgccat tgcgcgggtt tttttatgcc cgaaggcgcg ccagcacgca gtcaaacaaa    1320
aaacccgcgc cattgcgcgg gtttttttat gcccgaacgg ccgaggtctt ccgatctcct    1380
gaagccaggg cagatccgtg cacagcacct tgccgtagaa gaacagcaag gccgccaatg    1440
cctgacgatg cgtggagacc gaaaccttgc gctcgttcgc cagccaggac agaaatgcct    1500
cgacttcgct gctgcccaag gttgccgggt gacgcacacc gtggaaacgg atgaaggcac    1560
gaacccagtg gacataagcc tgttcggttc gtaagctgta atgcaagtag cgtatgcgct    1620
cacgcaactg gtccagaacc ttgaccgaac gcagcggtgg taacggcgca gtggcggttt    1680
tcatggcttg ttatgactgt ttttttgggg tacagtctat gcctcgggca tccaagcagc    1740
aagcgcgtta cgccgtgggt cgatgtttga tgttatggag cagcaacgat gttacgcagc    1800
agggcagtcg ccctaaaaca aagttaaaca tcatgaggga agcggtgatc gccgaagtat    1860
cgactcaact atcagaggta gttggcgtca tcgagcgcca tctcgaaccg acgttgctgg    1920
ccgtacattt gtacggctcc gcagtggatg gcggcctgaa gccacacagt gatattgatt    1980
tgctggttac ggtgaccgta aggcttgatg aaacaacgcg gcgagctttg atcaacgacc    2040
ttttggaaac ttcggcttcc cctggagaga gcgagattct ccgcgctgta gaagtcacca    2100
ttgttgtgca cgacgacatc attccgtggc gttatccagc taagcgcgaa ctgcaatttg    2160
```

```
gagaatggca gcgcaatgac attcttgcag gtatcttcga gccagccacg atcgacattg   2220
atctggctat cttgctgaca aaagcaagag aacatagcgt tgccttggta ggtccagcgg   2280
cggaggaact ctttgatccg gttcctgaac aggatctatt tgaggcgcta aatgaaacct   2340
taacgctatg gaactcgccg cccgactggg ctggcgatga gcgaaatgta gtgcttacgt   2400
tgtcccgcat ttggtacagc gcagtaaccg gcaaaatcgc gccgaaggat gtcgctgccg   2460
actgggcaat ggagcgcctg ccggcccagt atcagcccgt catacttgaa gctagacagg   2520
cttatcttgg acaagaagaa gatcgcttgg cctcgcgcgc agatcagttg gaagaatttg   2580
tccactacgt gaaaggcgag atcaccaagg tagtcggcaa ataatgtcta acaattcgtt   2640
caagccgacg ccgcttcgcg gcgcggctta actcaagcgt tagatgcact aagcacataa   2700
ttgctcacag ccaaactatc aggtcaagtc tgcttttatt atttttaagc gtgcataata   2760
agccctacac aaattgggag atatatcatg aaaggctggc ttttctttgt tatcgcaata   2820
gttggcgaag taatcgcaac atccgcatta aaatctagcg agggctttac taagctcgtc   2880
agcgggtgtt ggcgggtgtc ggggctggct taactatgcg gcatcagagc agattgtact   2940
gagagtgcac catatgcggt gtgaaatacc gcacagatgc gtaaggagaa ataccgcat   3000 caggcgccat cgccattca ggctgcgcaa ctgttgggaa gggcgatcgg tgcgggcctc   3060
ttcgctatta cgccagctgg cgaaagggg atgtgctgca aggcgattaa gttgggtaac   3120
gccagggttt tcccagtcac gacgttgtaa aacgacggcc agtccgtaat acgactcact   3180
taaggccttg actagagggt accatttaaa tgtatactct agcgcccgat ccagctggag   3240
tttgtagaaa cgcaaaaagg ccatccgtca ggatggcctt ctgcttaatt tgatgcctgg   3300
cagtttatgg cgggcgtcct gcccgccacc ctccggcccg ttgcttcgca acgttcaaat   3360
ccgctcccgg cggatttgtc ctactcagga gagcgttcac cgacaaacaa cagataaaac   3420
gaaaggccca gtctttcgac tgagcctttc gttttatttg atgcctggca gttccctact   3480
ctcgcatggg gagaccccac actaccatcg gcgctacggc gtttcacttc tgagttcggc   3540
atggggtcag gtgggaccac cgcgctactg ccgccaggca aattctgttt tatcagaccg   3600
cttctgcgtt ctgatttaat ctgtatcagg ctgaaaatct tctctcatcc gccaaaacag   3660
ccaagcttgc atgcctgcag cccgggttac catttcaaca gatcgtcctt agcatataag   3720
tagtcgtcaa aaatgaattc aacttcgtct gtttcggcat tgtagccgcc aactctgatg   3780
gattcgtggt ttttgacaat gatgtcacag ccttttttcct ttaggaagtc caagtcgaaa   3840
gtagtggcaa taccaatgat cttacaaccg gcggcttttc cggcggcaat acctgctgga   3900
gcgtcttcaa atactactac cttagatttg gaagggtctt gctcattgat cggatatcct   3960
aagccattcc tgcccttcag atatggttct ggatgaggct taccctgttt gacatcatta   4020
gcggtaatga agtactttgg tctcctgatt cccagatgct cgaaccattt ttgtgccata   4080
tcacgggtac cggaagttgc cacagcccat ttctcttttg gtagagcgtt caaagcgttg   4140
cacagcttaa ctgcacctgg gacttcaatg gattttttcac cgtacttgac cggaatttca   4200
gcttctaatt tgttaacata ctcttcattg gcaaagtctg gagcgaactt agcaatggca   4260
tcaaacgttc tccaaccatg cgagacttgg ataacgtgtt cagcatcgaa ataaggtttg   4320
tccttaccga aatccctcca gaatgcagca atggctggtt gagagatgat aatggtaccg   4380
tcgacgtcga acaaagcggc gttaactttc aaagatagag gtttagtagt caatcccata   4440
attctagtct gtttcctgga tccaataaat ctaatcttca tgtagatcta attcttcaat   4500
catgtccggc aggttcttca ttgggtagtt gttgtaaacg atttggtata cggcttcaaa   4560
```

```
taatgggaag tcttcgacag agccacatgt ttccaaccat tcgtgaactt ctttgcaggt    4620
aattaaacct tgagcggatt ggccattcaa caactccttt tcacattccc aggcgtcctt    4680
accagaagta gccattagcc tagcaacctt gacgtttcta ccaccagcgc aggtggtgat    4740
caaatcagca acaccagcag actcttggta gtatgtttct tctctagatt ctgggaaaaa    4800
catttgaccg aatctgatga tctcacccaa accgactctt tggatggcag cagaagcgtt    4860
gttaccccag cctagacctt cgacgaaacc acaacctaag gcaacaacgt tcttcaaagc    4920
accacagatg gagataccag caacatcttc gatgacacta acgtggaagt aaggtctgtg    4980
gaacaaggcc tttagaacct tatggtcgac gtccttgccc tcgcctctga aatcctttgg    5040
aatgtggtaa gcaactgttg tttcagacca gtgttcttga gcgacttcgg tggcaatgtt    5100
agcaccagat agagcaccac attgaatacc tagttcctca gtgatgtaag aggatagcaa    5160
ttggacacct ttagcaccaa cttcaaaacc ctttagacag gagatagctc tgacgtgtga    5220
atcaacatga cctttcaatt ggctacagat acggggcaaa aattgatgtg gaatgttgaa    5280
aacgatgatg tcgacatcct tgactgaatc aatcaagtct ggattagcaa ccaaattgtc    5340
gggtagagtg atgccaggca agtatttcac gttttgatgt ctagtattta tgatttcagt    5400 caattttca ccattgatct cttcttcgaa cacccacatt tgtactattg gagcgaaaac    5460
ttctgggtat cccttacaat tttcggcaac caccttggca atagtagtac cccagttacc    5520
agatccaatc acagtaacct tgaaaggctt ttcggcagcc ttcaaagaaa cagaagagga    5580
acttctcttt ctaccagcat tcaagtggcc ggaagttaag tttaatctat cagcagcagc    5640
agccatggaa ttgtcctcct tactagtcat ggtctgtttc ctgtgtgaaa ttgttatccg    5700
ctcacaattc cacacattat acgagccgga tgattaattg tcaacagctc atttcagaat    5760
atttgccaga accgttatga tgtcggcgca aaaaacatta tccagaacgg gagtgcgcct    5820
tgagcgacac gaattatgca gtgatttacg acctgcacag ccataccaca gcttccgatg    5880
gctgcctgac gccagaagca ttggtgcacg ctagacaaga aaaaaggcac gtcatctgac    5940
gtgccttttt tatttgtacc tagaggctgg cgcgagcgcc cgtttaattc gcctgaccgg    6000
ccagtagcag cccggtggcg accgcattgc gcggcccttc tgttccccga atattgccct    6060
gcccggcgac cacgccatag tgcgacaagg cttccgtgat aagctgcggg atctcaaagt    6120
ccagcgatga gccgcccacc agcaccacaa aggcgatatc gcgaatggaa ccgccgggtg    6180
agacctggcg cagcgcgcgc aggcagttgg tgacaaacac tttctctttc gcctgccggc    6240
gcacgagacg aattttttcc agcgggctgg cgttatcgat cggcaccagt tcgccctcct    6300
tgatgtacac cactttggcg aacaccgccg ggctgagggc ttcccgaaag aactccaccg    6360
cgccattctc gtgacgaata ctgaacaggc tttccacttt ggccagcggg tatttttta    6420 tcgcttccgc cagcgaaaga tcctcgaggc ccagctcggt tttaatcaac aggctgacca    6480
tattccccgc cccggcgaga tggaccgccg ttatctgccc ctccgcgttg acgatcgccg    6540
catccgtcga gccggcgccg aggtcgagga tcgccagcgg cgccgcacag ccgggagtgg    6600
ttaacgcccc ggcgatggcc atgttggcct ccacgccgcc caccaccacc tcggtctgca    6660
gtcgggcgct cagttcgcgg gcgataacct gcatttgcag acgatccgct ttcaccatcg    6720
ccgccatccc gacggcattc tccatggcgc actcgccggc catcccgccc tgcaccttgc    6780
gcggaataaa cgtatccacc gccagcagat cctggatgta tatcgcgctc atctcatggc    6840
cggtcaggga cgcccattac ttgcgcaccc gctcaagcat gccgcggcg tgggtgcccg    6900 gttcgccgcg gatgtcgcgt accggagcgc aggcgctcat cgcctgcatg atggcttccg    6960
```

```
cgccctcggc gacatcggcc tctccgcggc gcttttcgcc gctaatgtag aggttgcccg    7020
ccgggatcac ccgcgactgc acatccccct gcggggtctt gagcaccacc gcggaacggt    7080
tgccaatcag ggcgcgggcg atggggacga tggcctgggt ctcttccggg cttagcccga    7140
agaaggtggc gatcccgtag ggattcgaca ggatccgcac cacctggccc ggcgcggcca    7200
cttccaccgc cgccattacc ccctcgggga cctgctccag cagcgtcact tcatccacca    7260
ccggcagggt tttacgcagg cggttgttca ccagcacgcc gtcgtccttt ttgaggatcg    7320
ccgccaccac gttgatcccc cggtcgagcc cctcattgag ccaccacacg cgtcaagga    7380 aatcgacggc gtcgtcaatc agtacgatcc acccctcggc atactgcgcc gccggcagcg    7440
tcgccagccg cccgagggcg atagtcgtcc ccacgccaac gcccacccg cccggcgtct    7500 gcgggttatg accgatcatg gtcgattcgg tgataatggt ctcggtgatg gtctccatcg    7560
ccacatcgcc aataccggc gcggcttcgt taagatagat gcgagagaca tcgctcatcg    7620
accacggtgt tttcgccagg gcctgctcca gcgcggcgag ggtcccggcg atattgtccc    7680
gcgtcccttt catgcccgtc gtcgcgacga tcccgctggc aacaaacgcc ctcgcctgcg    7740
ggtagtcgga cgccagcgcc acctcggtgg tggcgttgcc gatatcaatc ccggctatta    7800
acggcatgct gacctccgct tagcttcctt tacgcagctt atgccgctgc tgatacactt    7860
ccgccgactc ccggacaaag gcggcattca ctgtcgcatg ccaggtgtgc tccagctcgt    7920
cggcgatcgc cagcagctcc gcctgcgagg agcggaacgg gcgcagcgcg ttatagatag    7980
ccagaatgcg ctcgtcagga atggcgataa gctccgccgc gcggcggaaa ttgcgcgcca    8040
ccgcatggcg ctgcatctgc tcggcaatct gcgcctggta ctcaagggtc tggcgggaga    8100
tccgcacatc ctgcgggccc acctcgccag agagcacctt ctcgagggta atatcggtca    8160
atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg cggctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520
ggtccccttc gactggatac cgatgccgat ccccgagccg ctcaggttgg ccgcatccca    8580
ggccataaag gagacgtcgg acgtgcgcag aatgcgcacc acccgggcgt gaagcccctc    8640
ttcttccacc ccggcaatca gctctttgag gatcgcgcca tggggcatat cgatcagagt    8700
gtgatgctgg tgtttatcga aggcagggcc gacgccgatc accacttcat cggcgcgttc    8760
atcggcagaa gctaccccgc cctcgcgggt tttcaggta aaagagggct gaatttgggt    8820
tgtctgttgc acaggaatac cgccttgttc aatggtgtcg ggctgaacca cgcccggaat    8880 attttgatc tccgcccagc gttcggcaga gatgcgatag ccggtgcccg gcccctgata    8940
gtcattgatg tcgttgaccg cactcaccac ctcgaactgc cgatcgaaaa tggccgaggt    9000
ctgcaggtaa tcgccggtga cccgctggcg cagcatattg agaatattgc tggcgatatc    9060
ctcaaagccg ctgcggctca gcgcgccgac aatatcgagg ccggtgatgt tgcgcttcat    9120
catctcttcc accgcactca gatcctccac cacgttacgc ggcggcatct cgttgctgcc    9180
gtgcgcgtag gtggcggcct ccacctcctc gtcggcgatt ggcggcagcc ccagctcgcg    9240
gaaaaccgcg tggatcgccc gcgccgcttt ctggcgaatg gcaatggttt ccgcctcggt    9300
caccggacgc aggccgccgt caaccatcag gtcacgctgc aggatgttgt aatcatcaaa    9360
```

```
atcttccgca tcgaagttcg agccggcgaa catgttgtcg tagttcggca ccgcgctgta   9420
gccggagaaa ataaagtcgg tgcccggcag catctgcatc agggtgcgcg cggtgcggcg   9480
aatatccgag tgggagaaag tctggtcgtt ggcggacgcc acttcgaggt cgagcataga   9540
ggcgatcagg ttttccgcca gcaccgcccg aatgcccgac ggcacagcgc cggtcatgcc   9600
gatacagctc accgcgccgt tttgcagtcc ctgaaccccg cgcctttag taatgaagat   9660 gcagcgcgat tcgaggtaga gcatcgactt gctctccgaa tagcccatca gcgcttcgga   9720
tccggtgccg gaggtgtagc gcattttcaa cccgcgggag gcgtaggccg aggcgaggaa   9780
cgcctttgac cacggcgtat catcgccgtc ggtaaatacc gcttcggtgc cgtagaccga   9840
caccgtctcg gcgtagctgg ttaagccacg catgcccagc tccagctcgg tggcctcttc   9900
caccgagcac tgcgtcaaca cgccggggcg gccgcactgc gaaccgacca acagcgccag   9960
ggcgttaaac ggcgcgtagc gcgcgatacc gaccgtggtc tcctgttctg agaagccgcg  10020
gatcccggcc tcggcggcgt cagcggcaat ctgcaccgga ttatctttga gattggtgac  10080
gtggcactgg ttgggagggg tccggcgggc acgcatcttc tgcagcgcca tcatcatctc  10140
caccacgttc atctgcgcca tcacctcgac cgctttggcc ggcgtgatgg cggtagtgat  10200
ggcaatgatc tcctcccggc tgacgtgaat atccaccagc atacgggcta tttccaccgc  10260
ctccaggcgc attgcctgct ctgtgcgctc aacgttgatc gcgtaatcgg cgataaatcg  10320
gtcgatcatg tcaaactggt cccggcgttt gccgtccagt tcgacgatca gaccgttgtc  10380 cactttact gaagagaccg ggtcaaaggg gctgtccatg gcgatcagcc cctcttcagg  10440
ccactcgcca atcagcccgt cctgattgac ggggcgctgg gccagtactg caaatcgttt  10500
tgatcttttc attgttcatc ggctcaaaag gtgaagcttg gttacctccg ggaaacgcgg  10560
ttgatttgtt tagtggttga attatttgct caggatgtgg cattgtcaag ggcgtgacgg  10620
ctcgcctgac ttctcgttcc agtgcccccg tccgacagtc gagcgtgcga gcccataatc  10680
tcgcgctggt gctgcatacc gtggcaaaca gcacagatcg cctaggaaaa aaaaagcccg  10740
cactgtcagg tgcgggcttt tttctgtgtt tgctaggcca gttcaagcgc aagcatcagg  10800
gtgcagctgg gcagaggcga gattcctccc cgggatcacg aactgtttta acgggccgct  10860
ctcggccata ttgcggtcga taagccgctc cagggcggtg atctcctctt cgccgatcgt  10920
ctggctcagg cgggtcaggc cccgcgcatc gctggccagt tcagccccca gcacgaacag  10980
cgtctgctga atatggtgca ggcttttccc cagcccggcg tcgcgggtcg tggcgtagca  11040
gacgcccagc tgggatatca gttcatcgac ggtgccgtag gcctcgacgc gaatatggtc  11100
tttctcgatg cggctgccgc cgtacagggc ggtggtgcct ttatccccgg tgcgggtata  11160
gatacgatac attcagtttc tctcacttaa cggcaggact ttaaccagct gcccggcgtt  11220
ggcgccgagc gtacgcagtt gatcgtcgct atcggtgacg tgtccggtag ccagcggcgc  11280
gtccgccggc agctgggcat gagtgagggc tatctcgccg gacgcgctga gcccgatacc  11340
cacccgcagg ggcgagcttc tggccgccag ggcgcccagc gcagcggcgt caccgcctcc  11400
gtcataggtt atggtctggc aggggacccc ctgctcctcc agccccagc acagctcatt  11460 gatggcgccg catggtgcc ccgcgcggatc gtaaaacagg cgtacgcctg gcggtgaaag  11520
cgacatgacg gtcccctcgt taacactcag aatgcctggc ggaacatacg atagctcata  11580
atataccttc tcgcttcagg ttataatgcg gaaaacaat ccagggcgca ctgggctaat  11640
aattgatcct gctcgaccgt accgccgcta acgccgacgg cgccaattac ctgctcatta  11700
aaaataactg gcaggccgcc gccaaaaata ataattcgct gttggttggt tagctgcaga  11760
```

```
ccgtacagag attgtcctgg ctggaccgct gacgtaattt catgggtacc ttgcttcagg   11820
ctgcaggcgc tccaggcttt attcagggaa atatcgcagc tggagacgaa ggcctcgtcc   11880
atccgctgga taagcagcgt gttgcctccg cggtcaacta cggaaaacac caccgccacg   11940
ttgatctcag tggctttttt ttccaccgcc gccgccattt gctgggcggc ggccagggtg   12000
attgtctgaa cttgttggct cttgttcatc attctctccc gcaagcttgg ttacctccgg   12060
gaaacgcggt tgatttgttt agtggttgaa ttatttgctc aggatgtggc attgtcaagg   12120
gcgtgacggc tcgcctgact tctcgttcca gtgcccccgt ccgacagtcg agcgtgcgag   12180
cccataatct cgcgctggtg ctgcataccg tggcaaacag cacagatcgc ctagcagtca   12240
aaagcctccg gtcggaggct tttgactatt taaatgaatt cccgacagta agacgggtaa   12300
gcctgttgat gataccgctg ccttactggg tgcattagcc agtctgaatg acctgtcacg   12360
ggataatccg aagtggtcag actggaaaat cagagggcag gaactgctga cagcaaaaa    12420
gtcagatagc accacatagc agaccccgcca taaaacgccc tgagaagccc gtgacgggct   12480
tttcttgtat tatgggtagt ttccttgcat gaatccataa aaggcgcctg tagtgccatt   12540
tacccccatt cactgccaga gccgtgagcg cagcgaactg aatgtcacga aaagacagc    12600
gactcaggtg cctgatggtc ggagacaaaa ggaatattca gcgatttgcc cgagcttgcg   12660
agggtgctac ttaagccttt agggttttaa ggtctgtttt gtagaggagc aaacagcgtt   12720
tgcgacatcc ttttgtaata ctgcggaact gactaaagta gtgagttata cacagggctg   12780
ggatctattc tttttatctt tttttattct ttctttattc tataaattat aaccacttga   12840
atataaacaa aaaaaacaca caaaggtcta gcggaattta cagagggtct agcagaattt   12900
acaagttttc cagcaaaggt ctagcagaat ttacagatac ccacaactca aaggaaaagg   12960
actagtaatt atcattgact agcccatctc aattggtata gtgattaaaa tcacctagac   13020
caattgagat gtatgtctga attagttgtt ttcaaagcaa atgaactagc gattagtcgc   13080
tatgacttaa cggagcatga aaccaagcta attttatgct gtgtggcact actcaacccc   13140
acgattgaaa accctacaag gaaagaacgg acggtatcgt tcacttataa ccaatacgct   13200
cagatgatga acatcagtag ggaaaatgct tatggtgtat tagctaaagc aaccagagag   13260
ctgatgacga gaactgtgga aatcaggaat cctttggtta aaggctttga gattttccag   13320
tggacaaaact atgccaagtt ctcaagcgaa aaattagaat tagttttag tgaagagata   13380
ttgccttatc ttttccagtt aaaaaaattc ataaaatata atctggaaca tgttaagtct   13440
tttgaaaaca aatactctat gaggatttat gagtggttat taaaagaact aacacaaaag   13500
aaaactcaca aggcaaatat agagattagc cttgatgaat ttaagttcat gttaatgctt   13560
gaaataact accatgagtt taaaaggctt aaccaatggg ttttgaaacc aataagtaaa   13620
gatttaaaca cttacagcaa tatgaaattg gtggttgata agcgaggccg cccgactgat   13680
acgttgattt tccaagttga actagataga caaatggatc tcgtaaccga acttgagaac   13740
aaccagataa aaatgaatgg tgacaaaata ccaacaacca ttacatcaga ttcctaccta   13800
cataacggac taagaaaaac actacacgat gctttaactg caaaaattca gctcaccagt   13860
tttgaggcaa aatttttgag tgacatgcaa agtaagtatg atctcaatgg ttcgttctca   13920
tggctcacgc aaaaacaacg aaccacacta gagaacatac tggctaaata cggaaggatc   13980
tgaggttctt atggctcttg tatctatcag tgaagcatca agactaacaa acaaaagtag   14040
aacaactgtt caccgttaca tatcaaaggg aaaactgtcc atatgcacag atgaaaacgg   14100
tgtaaaaaag atagatacat cagagctttt acgagttttt ggtgcattca aagctgttca   14160
```

```
ccatgaacag atcgacaatg taacagatga acagcatgta acacctaata gaacaggtga    14220
aaccagtaaa acaaagcaac tagaacatga aattgaacac ctgagacaac ttgttacagc    14280
tcaacagtca cacatagaca gcctgaaaca ggcgatgctg cttatcgaat caaagctgcc    14340
gacaacacgg gagccagtga cgcctcccgt ggggaaaaaa tcatggcaat tctggaagaa    14400
atagcgcttt cagccggcaa accggctgaa gccggatctg cga                     14443
```

```
<210> SEQ ID NO 40
<211> LENGTH: 60
<212> TYPE: DNA
<213> ORGANISM: Artificial Sequence
<220> FEATURE:
<223> OTHER INFORMATION: Primer

<400> SEQUENCE: 40
cgatgttggc aggaatggtg tgtttgtgaa tttggctcat tttagcttcc ttagctcctg    60
```

```
<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41
cgatgttggc aggaatggtg tgtttgtgaa tttggctcat atgagttaat ttctcctctt    60
```

```
<210> SEQ ID NO 42
<211> LENGTH: 60
<212> TYPE: DNA
<213> ORGANISM: Artificial Sequence
<220> FEATURE:
<223> OTHER INFORMATION: primer

<400> SEQUENCE: 42
gttgtcttta atcaattgta agtgcatgta aataccact gtgcgtagtc gttggcaagc    60
```

```
<210> SEQ ID NO 43
<211> LENGTH: 45
<212> TYPE: DNA
<213> ORGANISM: Artificial Sequence
<220> FEATURE:
<223> OTHER INFORMATION: Primer

<400> SEQUENCE: 43
ataagaatgc ggccgctgac attaacctat aaaaataggc gtatc                   45
```

```
<210> SEQ ID NO 44
<211> LENGTH: 48
<212> TYPE: DNA
<213> ORGANISM: Artificial Sequence
<220> FEATURE:
<223> OTHER INFORMATION: Primer

<400> SEQUENCE: 44
ataagaatgc ggccgcctat aaaaataggc gtatcacgag gccctttc                48
```

```
<210> SEQ ID NO 45
<211> LENGTH: 44
<212> TYPE: DNA
<213> ORGANISM: Artificial Sequence
<220> FEATURE:
<223> OTHER INFORMATION: Primer

<400> SEQUENCE: 45
```

```
ccagctttgt ttaaacttac gatggcatcg cgatagcctg cttc          44
```

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46

```
tgtacggcag agggcgacat tttagcttcc ttagctcctg               40
```

<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47

```
ttatgttcct tgattgtcat tttagcttcc ttagctcctg               40
```

<210> SEQ ID NO 48
<211> LENGTH: 40
<212> TYPE: DNA
<213> ORGANISM: Artificial Sequence
<220> FEATURE:
<223> OTHER INFORMATION: Primer

<400> SEQUENCE: 48

```
ttatgttcct tgattgtcat tttagcttcc ttagctcctg               40
```

<210> SEQ ID NO 49
<211> LENGTH: 45
<212> TYPE: DNA
<213> ORGANISM: Artificial Sequence
<220> FEATURE:
<223> OTHER INFORMATION: Primer

<400> SEQUENCE: 49

```
ccagctttgt ttaaacttac aacttgaccg aatcaattag atgtc         45
```

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50

```
caggagctaa ggaagctaaa atgacaatca aggaacataa              40
```

<210> SEQ ID NO 51
<211> LENGTH: 36
<212> TYPE: DNA
<213> ORGANISM: Artificial Sequence
<220> FEATURE:
<223> OTHER INFORMATION: Primer

<400> SEQUENCE: 51

```
ccagctttgt ttaaacttat ttcttttttt gagaga                  36
```

<210> SEQ ID NO 52
<211> LENGTH: 3772
<212> TYPE: DNA
<213> ORGANISM: Artificial Sequence
<220> FEATURE:
<223> OTHER INFORMATION: Plasmid

<400> SEQUENCE: 52

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgacagct gtctcttata cacatctcaa ccatcatcga tgaattttct cgggtgttct     360
cgcatattgg ctcgaattct acctgcagat gagttaattt ctcctcttta atgaattctg     420
tgtgaaattg ttatccgctc acaattgaat ctattataat tgttatccgc tcacaaagca     480
aataaatttt ttatgatttc tcgaggtgaa gacgaaaggg cctcgtgata cgcctatttt     540
tataggccg gccataactt cgtatagcat acattatacg aagttattta attaacacac     600
aacaggccaa gactacaaag gcgcgcttag aaaaactcat cgagcatcaa atgaaactgc     660
aatttattca tatcaggatt atcaatacca tatttttgaa aaagccgttt ctgtaatgaa     720
ggagaaaact caccgaggca gttccatagg atggcaagat cctggtatcg gtctgcgatt     780
ccgactcgtc caacatcaat acaacctatt aatttcccct cgtcaaaaat aaggttatca     840
agtgagaaat caccatgagt gacgactgaa tccggtgaga atggcaaaag tttatgcatt     900
tctttccaga cttgttcaac aggccagcca ttacgctcgt catcaaaatc actcgcatca     960
accaaaccgt tattcattcg tgattgcgcc tgagcgagac gaaatacgcg atcgctgtta    1020
aaaggacaat tacaaacagg aatcgaatgc aaccggcgca ggaacactgc cagcgcatca    1080
acaatatttt cacctgaatc aggatattct tctaatacct ggaatgctgt tttcccgggg    1140
atcgcagtgg tgagtaacca tgcatcatca ggagtacgga taaatgctt gatggtcgga    1200
agaggcataa attccgtcag ccagtttagt ctgaccatct catctgtaac atcattggca    1260
acgctacctt tgccatgttt cagaaacaac tctggcgcat cgggcttccc atacaatcga    1320
tagattgtcg cacctgattg cccgacatta tcgcgagccc atttataccc atataaatca    1380
gcatccatgt tggaatttaa tcgcggccta gagcaagacg tttcccgttg aatatggctc    1440
ataacacccc ttgtattact gtttatgtaa gcagacagtt ttattgttca tgaccaaaat    1500
cccttaacgt gagttttcgt tccactgagc gtcagacccc gtagaaaaga tcaaaggatc    1560
ttcttgagat cctttttttc tgcgcgtaat ctgctgctct agcggccgca aacttcgta    1620
tagcatacat tatacgaagt tatgcgatcg caagcttgcc aacgactacg cactagccaa    1680
caagagcttc agggttgaga tgtgtataag agacagctgt cttaatgaat cggccaacgc    1740
gcggggagag gcggtttgcg tattgggcgc tcttccgctt cctcgctcac tgactcgctg    1800
cgctcggtcg ttcggctgcg gcgagcggta tcagctcact caaaggcggt aatacggtta    1860
tccacagaat caggggataa cgcaggaaag aacatgtgag caaaaggcca gcaaaaggcc    1920
aggaaccgta aaaaggccgc gttgctggcg ttttccata ggctccgccc cctgacgag    1980
catcacaaaa atcgacgctc aagtcagagg tggcgaaacc cgacaggact ataaagatac    2040
caggcgtttc ccctggaag ctccctcgtg cgctctcctg ttccgaccct gccgcttacc    2100
ggatacctgt ccgcctttct cccttcggga agcgtggcgc tttctcatag ctcacgctgt    2160
aggtatctca gttcggtgta ggtcgttcgc tccaagctgg gctgtgtgca cgaaccccc    2220
gttcagcccg accgctgcgc cttatccggt aactatcgtc ttgagtccaa cccggtaaga    2280
```

```
cacgacttat cgccactggc agcagccact ggtaacagga ttagcagagc gaggtatgta    2340
ggcggtgcta cagagttctt gaagtggtgg cctaactacg gctacactag aaggacagta    2400
tttggtatct gcgctctgct gaagccagtt accttcggaa aaagagttgg tagctcttga    2460
tccggcaaac aaaccaccgc tggtagcggt ggttttttg tttgcaagca gcagattacg     2520
cgcagaaaaa aaggatctca agaagatcct ttgatctttt ctacgggtc tgacgctcag     2580 tggaacgaaa actcacgtta agggattttg gtcatgagat tatcaaaaag gatcttcacc    2640
tagatccttt taaattaaaa atgaagtttt aaatcaatct aaagtatata tgagtaaact    2700
tggtctgaca gttaccaatg cttaatcagt gaggcaccta tctcagcgat ctgtctattt    2760
cgttcatcca tagttgcctg actccccgtc gtgtagataa ctacgatacg ggagggctta    2820
ccatctggcc ccagtgctgc aatgataccg cgagacccac gctcaccggc tccagattta    2880
tcagcaataa accagccagc cggaagggcc gagcgcagaa gtggtcctgc aactttatcc    2940
gcctccatcc agtctattaa ttgttgccgg gaagctagag taagtagttc gccagttaat    3000
agtttgcgca acgttgttgc cattgctaca ggcatcgtgg tgtcacgctc gtcgtttggt    3060
atggcttcat tcagctccgg ttcccaacga tcaaggcgag ttacatgatc ccccatgttg    3120
tgcaaaaaag cggttagctc cttcggtcct ccgatcgttg tcagaagtaa gttggccgca    3180
gtgttatcac tcatggttat ggcagcactg cataattctc ttactgtcat gccatccgta    3240
agatgctttt ctgtgactgg tgagtactca accaagtcat tctgagaata gtgtatgcgg    3300
cgaccgagtt gctcttgccc ggcgtcaata cgggataata ccgcgccaca tagcagaact    3360
ttaaaagtgc tcatcattgg aaaacgttct tcggggcgaa aactctcaag gatcttaccg    3420
ctgttgagat ccagttcgat gtaacccact cgtgcaccca actgatcttc agcatctttt    3480
actttcacca gcgtttctgg gtgagcaaaa acaggaaggc aaaatgccgc aaaaaaggga    3540
ataagggcga cacggaaatg ttgaatactc atactcttcc ttttcaata ttattgaagc     3600 atttatcagg gttattgtct catgagcgga tacatatttg aatgtattta gaaaaataaa    3660 caaataggg ttccgcgcac atttccccga aaagtgccac ctgacgtcta agaaaccatt     3720
attatcatga cattaaccta taaaaatagg cgtatcacga ggccctttcg tc            3772

<210> SEQ ID NO 53
<211> LENGTH: 3868
<212> TYPE: DNA
<213> ORGANISM: Artificial Sequence
<220> FEATURE:
<223> OTHER INFORMATION: Plasmid

<400> SEQUENCE: 53
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgacagct gtctcttata cacatctcaa ccatcatcga tgaattttct cgggtgttct    360
cgcatattgg ctcgaattct acctgcagtt tagcttcctt agctcctgaa aatctcgata    420
actcaaaaaa tacgcccggt agtgatctta tttcattatg gtgaaagttg gaacctctta    480
cgtgccgatc aacgtctcat tttcgccaaa agttggccca gggcttcccg gtatcaacag    540
ggacaccagg atttatttat tctgcgaagt gatcttccgt cacaggtatt tattcggcgc    600
```

```
aaagggcctc gtgatacgcc tattttata  ggttaatgtc aggccggcca taacttcgta   660
tagcatacat tatacgaagt tatttaatta acacacaaca ggccaagact acaaaggcgc   720
gcttagaaaa actcatcgag catcaaatga aactgcaatt tattcatatc aggattatca   780
ataccatatt tttgaaaaag ccgtttctgt aatgaaggag aaaactcacc gaggcagttc   840
cataggatgg caagatcctg gtatcggtct gcgattccga ctcgtccaac atcaatacaa   900
cctattaatt tcccctcgtc aaaaataagg ttatcaagtg agaaatcacc atgagtgacg   960
actgaatccg gtgagaatgg caaaagttta tgcatttctt tccagacttg ttcaacaggc  1020
cagccattac gctcgtcatc aaaatcactc gcatcaacca aaccgttatt cattcgtgat  1080
tgcgcctgag cgagacgaaa tacgcgatcg ctgttaaaag acaattaca  acaggaatc   1140
gaatgcaacc ggcgcaggaa cactgccagc gcatcaacaa tattttcacc tgaatcagga  1200
tattcttcta atacctggaa tgctgttttc ccggggatcg cagtggtgag taaccatgca  1260
tcatcaggag tacggataaa atgcttgatg gtcggaagag gcataaattc cgtcagccag  1320
tttagtctga ccatctcatc tgtaacatca ttggcaacgc tacctttgcc atgtttcaga  1380
aacaactctg gcgcatcggg cttcccatac aatcgataga ttgtcgcacc tgattgcccg  1440
acattatcgc gagcccattt atacccatat aaatcagcat ccatgttgga atttaatcgc  1500
ggcctagagc aagacgtttc ccgttgaata tggctcataa caccccttgt attactgttt  1560
atgtaagcag acagttttat tgttcatgac caaaatccct taacgtgagt tttcgttcca  1620
ctgagcgtca gaccccgtag aaaagatcaa aggatcttct tgagatcctt ttttctgcg  1680
cgtaatctgc tgctctagcg gccgcataac ttcgtatagc atacattata cgaagttatg  1740
cgatcgcaag cttgccaacg actacgcact agccaacaag agcttcaggg ttgagatgtg  1800
tataagagac agctgtctta atgaatcggc caacgcgcgg ggagaggcgg tttgcgtatt  1860
gggcgctctt ccgcttcctc gctcactgac tcgctgcgct cggtcgttcg gctgcggcga  1920
gcggtatcag ctcactcaaa ggcggtaata cggttatcca cagaatcagg ggataacgca  1980
ggaaagaaca tgtgagcaaa aggccagcaa aaggccagga accgtaaaaa ggccgcgttg  2040
ctggcgtttt tccataggct ccgcccccct gacgagcatc acaaaaatcg acgctcaagt  2100
cagaggtggc gaaacccgac aggactataa agataccagg cgtttccccc tggaagctcc  2160
ctcgtgcgct ctcctgttcc gaccctgccg cttaccggat acctgtccgc ctttctccct  2220
tcgggaagcg tggcgctttc tcatagctca cgctgtaggt atctcagttc ggtgtaggtc  2280
gttcgctcca agctgggctg tgtgcacgaa ccccccgttc agcccgaccg ctgcgcctta  2340
tccggtaact atcgtcttga gtccaacccg gtaagacacg acttatcgcc actggcagca  2400
gccactggta acaggattag cagagcgagg tatgtaggcg gtgctacaga gttcttgaag  2460
tggtggccta actacggcta cactagaagg acagtatttg gtatctgcgc tctgctgaag  2520
ccagttacct tcggaaaaag agttggtagc tcttgatccg gcaaacaaac caccgctggt  2580
agcggtggtt tttttgtttg caagcagcag attacgcgca gaaaaaaagg atctcaagaa  2640
gatcctttga tcttttctac ggggtctgac gctcagtgga acgaaaactc acgttaaggg  2700
attttggtca tgagattatc aaaaaggatc ttcacctaga tccttttaaa ttaaaaatga  2760
agttttaaat caatctaaag tatatatgag taaacttggt ctgacagtta ccaatgctta  2820
atcagtgagg cacctatctc agcgatctgt ctatttcgtt catccatagt tgcctgactc  2880
cccgtcgtgt agataactac gatacgggag ggcttaccat ctggccccag tgctgcaatg  2940
ataccgcgag acccacgctc accggctcca gatttatcag caataaacca gccagccgga  3000
```

```
agggccgagc gcagaagtgg tcctgcaact ttatccgcct ccatccagtc tattaattgt    3060
tgccgggaag ctagagtaag tagttcgcca gttaatagtt tgcgcaacgt tgttgccatt    3120
gctacaggca tcgtggtgtc acgctcgtcg tttggtatgg cttcattcag ctccggttcc    3180
caacgatcaa ggcgagttac atgatccccc atgttgtgca aaaagcggt  tagctccttc    3240 ggtcctccga tcgttgtcag aagtaagttg gccgcagtgt tatcactcat ggttatggca    3300
gcactgcata attctcttac tgtcatgcca tccgtaagat gcttttctgt gactggtgag    3360
tactcaacca agtcattctg agaatagtgt atgcggcgac cgagttgctc ttgcccggcg    3420
tcaatacggg ataataccgc gccacatagc agaactttaa aagtgctcat cattggaaaa    3480
cgttcttcgg ggcgaaaact ctcaaggatc ttaccgctgt tgagatccag ttcgatgtaa    3540
cccactcgtg cacccaactg atcttcagca tctttactt  tcaccagcgt ttctgggtga    3600
gcaaaaacag gaaggcaaaa tgccgcaaaa aagggaataa gggcgacacg gaaatgttga    3660
atactcatac tcttcctttt tcaatattat tgaagcattt atcagggtta ttgtctcatg    3720
agcggataca tatttgaatg tatttagaaa aataaacaaa tagggggttcc gcgcacattt    3780 ccccgaaaag tgccacctga cgtctaagaa accattatta tcatgacatt aacctataaa    3840
aataggcgta tcacgaggcc ctttcgtc                                      3868
```

<210> SEQ ID NO 54
<211> LENGTH: 1255
<212> TYPE: DNA
<213> ORGANISM: Artificial Sequence
<220> FEATURE:
<223> OTHER INFORMATION: Plasmid

<400> SEQUENCE: 54

```
ataacttcgt ataatgtatg ctatacgaag ttatgcggcc gctagagcag cagattacgc      60
gcagaaaaaa aggatctcaa gaagatcctt tgatctttc  tacggggtct gacgctcagt     120
ggaacgaaaa ctcacgttaa gggattttgg tcatgaacaa taaaactgtc tgcttacata     180
aacagtaata caagggggtgt tatgagccat attcaacggg aaacgtcttg ctctaggccg     240
cgattaaatt ccaacatgga tgctgattta tatgggtata aatgggctcg cgataatgtc     300
gggcaatcag gtgcgacaat ctatcgattg tatgggaagc ccgatgcgcc agagttgttt     360
ctgaaacatg gcaaaggtag cgttgccaat gatgttacag atgagatggt cagactaaac     420
tggctgacgg aatttatgcc tcttccgacc atcaagcatt ttatccgtac tcctgatgat     480
gcatggttac tcaccactgc gatccccggg aaaacagcat tccaggtatt agaagaatat     540
cctgattcag gtgaaaatat tgttgatgcg ctggcagtgt tcctgcgccg gttgcattcg     600
attcctgttt gtaattgtcc ttttaacagc gatcgcgtat ttcgtctcgc tcaggcgcaa     660
tcacgaatga ataacggttt ggttgatgcg agtgattttg atgacgagcg taatggctgg     720
cctgttgaac aagtctggaa agaaatgcat aaacttttgc cattctcacc ggattcagtc     780
gtcactcatg gtgatttctc acttgataac cttattttg  acgaggggaa attaataggt     840
tgtattgatg ttggacgagt cggaatcgca gaccgatacc aggatcttgc catcctatgg     900
aactgcctcg gtgagttttc tccttcatta cagaaacggc ttttttcaaaa atatggtatt     960 gataatcctg atatgaataa attgcagttt catttgatgc tcgatgagtt tttctaagcg    1020 cgcccttttgta gtcttggcct gttgtgtgtt aattaaataa cttcgtataa tgtatgctat    1080
acgaagttat ggccggccct ataaaaatag gcgtatcacg aggcccttttc gtcttcacct    1140 cgagaaatca taaaaaattt atttgctttg tgagcggata acaattataa tagattcaat    1200
```
tgtgagcgga taacaatttc acacagaatt cattaaagag gagaaattaa ctcat      1255

<210> SEQ ID NO 55
<211> LENGTH: 1351
<212> TYPE: DNA
<213> ORGANISM: Artificial Sequence
<220> FEATURE:
<223> OTHER INFORMATION: Plasmid

<400> SEQUENCE: 55
ataacttcgt ataatgtatg ctatacgaag ttatgcggcc gctagagcag cagattacgc      60
gcagaaaaaa aggatctcaa gaagatcctt tgatcttttc tacggggtct gacgctcagt     120
ggaacgaaaa ctcacgttaa gggattttgg tcatgaacaa taaaactgtc tgcttacata     180
aacagtaata caagggtgt tatgagccat attcaacggg aaacgtcttg ctctaggccg     240
cgattaaatt ccaacatgga tgctgattta tatgggtata atgggctcg cgataatgtc     300
gggcaatcag gtgcgacaat ctatcgattg tatgggaagc ccgatgcgcc agagttgttt     360
ctgaaacatg gcaaaggtag cgttgccaat gatgttacag atgagatggt cagactaaac     420
tggctgacgg aatttatgcc tcttccgacc atcaagcatt ttatccgtac tcctgatgat     480
gcatggttac tcaccactgc gatccccggg aaaacagcat tccaggtatt agaagaatat     540
cctgattcag gtgaaaatat tgttgatgcg ctggcagtgt tcctgcgccg gttgcattcg     600
attcctgttt gtaattgtcc ttttaacagc gatcgcgtat tcgtctcgc tcaggcgcaa     660
tcacgaatga ataacggttt ggttgatgcg agtgattttg atgacgagcg taatggctgg     720
cctgttgaac aagtctggaa agaaatgcat aaacttttgc cattctcacc ggattcagtc     780
gtcactcatg gtgatttctc acttgataac cttatttttg acgaggggaa attaataggt     840
tgtattgatg ttggacgagt cggaatcgca gaccgatacc aggatcttgc catcctatgg     900
aactgcctcg gtgagttttc tccttcatta cagaaacggc ttttttcaaaa atatggtatt     960
gataatcctg atatgaataa attgcagttt catttgatgc tcgatgagtt tttctaagcg    1020
cgcctttgta gtcttggcct gttgtgtgtt aattaaataa cttcgtataa tgtatgctat    1080
acgaagttat ggccggcctg acattaacct ataaaaatag gcgtatcacg aggccctttg    1140
cgccgaataa atacctgtga cggaagatca cttcgcagaa taaataaatc ctggtgtccc    1200
tgttgatacc gggaagccct gggccaactt ttggcgaaaa tgagacgttg atcggcacgt    1260
aagaggttcc aactttcacc ataatgaaat aagatcacta ccgggcgtat tttttgagtt    1320
atcgagattt tcaggagcta aggaagctaa a                                   1351

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
ggatctaaag cagaaaaatc tgc                                             23

<210> SEQ ID NO 57
<211> LENGTH: 30
<212> TYPE: DNA
<213> ORGANISM: Artificial Seqeunce
<220> FEATURE:
<223> OTHER INFORMATION: Primer

<400> SEQUENCE: 57

```
ttcaagctta acaactgtt ctcccatacg                                    30

<210> SEQ ID NO 58
<211> LENGTH: 1317
<212> TYPE: DNA
<213> ORGANISM: Escherichia coli

<400> SEQUENCE: 58
atgggaaaca catcaataca aacgcagagt taccgtgcgg tagataaaga tgcagggcaa     60
agcagaagtt acattattcc attcgcgctg ctgtgctcac tgtttttct ttgggcggta    120 gccaataacc ttaacgacat tttattacct caattccagc aggcttttac gctgacaaat    180
ttccaggctg gcctgatcca atcggccttt tactttggtt atttcattat cccaatccct    240
gctgggatat tgatgaaaaa actcagttat aaagcaggga ttattaccgg ttattttta    300 tatgccttgg gtgctgcatt attctggccc gccgcagaaa taatgaacta caccttgttt    360
ttagttggcc tatttattat tgcagccgga ttaggttgtc tggaaactgc cgcaaaccct    420
tttgttacgg tattagggcc ggaaagtagt ggtcacttcc gcttaaatct tgcgcaaaca    480
tttaactcgt ttggcgcaat tatcgcggtt gtctttgggc aaagtcttat tttgtctaac    540
gtgccacatc aatcgcaaga cgttctcgat aaaatgtctc cagagcaatt gagtgcgtat    600
aaacacagcc tggtattatc ggtacagaca cctatatga tcatcgtggc tatcgtgtta    660
ctggtcgccc tgctgatcat gctgacgaaa ttcccggcat tgcagagtga taatcacagt    720
gacgccaaac aaggatcgtt ctccgcatcg ctttctcgcc tggcgcgtat tcgccactgg    780
cgctgggcgg tattagcgca attctgctat gtcggcgcac aaacggcctg ctggagctat    840
ttgattcgct acgctgtaga agaaattcca ggtatgactg caggctttgc cgctaactat    900
ttaaccggaa ccatggtgtg cttctttatt ggtcgtttca ccggtacctg gctcatcagt    960
cgcttcgcac cacacaaagt cctggccgcc tacgcattaa tcgctatggc actgtgcctg   1020
atctcagcct tcgctggcgg tcatgtgggc ttaatagccc tgactttatg cagcgccttt   1080
atgtcgattc agtacccaac aatcttctcg ctgggcatta agaatctcgg ccaggacacc   1140
aaatatggtt cgtccttcat cgttatgacc attattggcg gcggtattgt cactccggtc   1200
atgggttttg tcagtgacgc ggcgggcaac atcccactg ctgaactgat ccccgcactc   1260
tgcttcgcgg tcatctttat ctttgcccgt ttccgttctc aaacggcaac taactga     1317

<210> SEQ ID NO 59
<211> LENGTH: 25
<212> TYPE: DNA
<213> ORGANISM: Artificial Seqience
<220> FEATURE:
<223> OTHER INFORMATION: Primer

<400> SEQUENCE: 59
atgggaaaca catcaataca aacgc                                        25

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
cagctgtcag ttagttgccg tttgagaacg                                   30
```

<210> SEQ ID NO 61
<211> LENGTH: 5770
<212> TYPE: DNA
<213> ORGANISM: Artificial Sequence
<220> FEATURE:
<223> OTHER INFORMATION: Plasmid

<400> SEQUENCE: 61

| | | | | | |
|---|---|---|---|---|---|
| aaaaatagat | tttatttttt | tgatgcaggt | caagattgac | tcattagagg | tatcggtgag | 60 |
| gagacactgg | aagagaagag | atcgttgtaa | tgcttttcaa | attaacgtaa | agcgggtata | 120 |
| tttcggttgt | tattagctgc | gcagagggtg | gcactctgtg | gagcaaagcg | gcgaaagccg | 180 |
| gacggcagaa | tgcgccataa | ggcattcagg | agagatggca | tttacgggca | gtaagtcaga | 240 |
| agaccgaaga | tgttccggaa | gccataaaag | gaaaacccccc | acaatctttc | gacgaacttg | 300 |
| gcgggacgga | gaaagattat | gggggcctca | cagaatacgg | gtaaagtata | atgaaaccgt | 360 |
| accagagatt | caaccctgtg | cagtgtataa | atacacggca | caatcgctcc | gccataagcg | 420 |
| acagcttgtg | gcaggtctga | agaatactcc | atataacgca | gtacactgga | gtcagttagc | 480 |
| acccgaagag | cagatccgtt | tctgggaaga | ctatgaagcg | ggaagggcga | ccactttcct | 540 |
| ggttgaaccg | gaaaggaagc | gcacgaagcg | ccgtcgcggt | gagcactcca | ccaaacccaa | 600 |
| atgcgaaaat | ccgtcctggt | atcgtcctga | gcgctataag | gcgctgagcg | ggcagctcgg | 660 |
| gcacgcctac | aaccgtctgg | tgaaaaagga | cccggtgacc | ggcgagcaga | gcctgcgcat | 720 |
| gcacatgtct | ctgcatcctt | tttacgtgca | gaaacgaacg | tatgccggtc | gcaaatatgc | 780 |
| tttccgtccg | gaaaaacaac | gcctcctcga | tgccatctgg | ccggttctgg | tcagcttcag | 840 |
| tgatgcgggc | acacataccg | taggcatgag | tgtttcccgt | ctggccagag | aaatcagccc | 900 |
| gaaagacagc | aaggggaagg | ttattccgga | actggaagtg | acgtctcccc | gcctttcccg | 960 |
| tttgctggcc | gaacaggtac | gttttggtgt | gctgggtgtt | tcagaggaaa | ccctgtggga | 1020 |
| ccgtgaaacc | cgccagcgtc | tgccacgtta | cgtctggata | acaccggcag | gctggcagat | 1080 |
| gctgggcgtc | gacatggtaa | aacttcacga | acagcagcag | aaacgactgc | gtgaaagtga | 1140 |
| aatccgccag | cagctcattc | gggaaggtgt | tctgcgtgag | gatgaagata | tctccgtaca | 1200 |
| tgcggccaga | aaacgctggt | atctgcagcg | cagccaggat | gcactgaaac | accgtcgtgc | 1260 |
| aaaagcggca | gccagtaagc | gcgccagacg | cctgaagaaa | ctgcctgccg | accagcagat | 1320 |
| tcatgagatg | gcagagtatc | tcaggaagcg | tctgcctccg | gatgaagcct | atttttgttc | 1380 |
| cgatgaccat | ctgaagcgaa | tggccatcag | ggagttgcgt | cagcttgaac | tgacgctggc | 1440 |
| tgccccgcca | ccgcactaga | cagcaccatt | ccctcagcac | tgaatcatca | ccagccccctc | 1500 |
| cggggctttc | ggcgctggtt | ccgctcagcc | caaaatccgc | agtaatcacc | ttaaatcccc | 1560 |
| tcagaggggc | atatctgccc | ataaaaccac | gcatcagtca | tcagaacatg | gccacgtcgt | 1620 |
| ttcagttatc | cacataaatc | cgcaaacaaa | gaactttaag | aagctgcaaa | cctgaaacag | 1680 |
| caaacctgca | atatagtctt | aaccccatta | tttaatcccc | tgcgttgctt | cgccgcaggg | 1740 |
| aaaatcttta | tctctgagac | cactgtgaac | aaatacaaag | aggccttcgc | ttgcagcggc | 1800 |
| caaggccgcg | ccgtcagaa | tctaaaagca | cctcccacgc | tgatgcgcgg | gccccgaacc | 1860 |
| tcaccgttct | gaaaccacaa | caaaaaaaca | tcaggaataa | aaacaccaca | caaacgcagc | 1920 |
| accgtaccca | cccctcataa | ctgaaaagcg | aggccgcccc | cgcccgaagg | gcgggaacaa | 1980 |
| catcgctttt | aattatgaat | gttgtaacta | cattgtcatc | gctgccagtc | ttctggctgg | 2040 |
| aagtcctcag | tacacgctcg | taagcggccc | tgacggcccg | ctaacgcgga | gatacgcccc | 2100 |
| gactgcgggt | aaacccttgt | cgggaccact | ccgaccgcgc | acagaagcta | tttcatggct | 2160 |

```
gaagcgggta tggcttagca ggatggggat gggtaaggtg aaatctatca atcagtaccg    2220
gctgacgccg ggcttcggcg gttttgtttc tgtgccatat gtaacaacgg agtgccgcct    2280
tacatgcgct gacgcgcatt atttgccttg tttcgtctga aagtaatcac tatgattaaa    2340
tatgattaac agctaatcgg atatgcaaat gaaaaacaat accgcacaag caacaaaagt    2400
aattaccgcg catgtgccat tacctatggc tgataaagtc gaccagatgg ccgccagact    2460
ggaacgctcc cggggctgga ttatcaaaca ggcgctttct gcatggcttg cccaggagga    2520
ggagcgtaat cgcctgacgc tggaagccct ggacgatgtg acatccggac aggttatcga    2580
ccatcaggct gtacaggcct gggcggacag cctcagtact gacaatccgt taccggtgcc    2640
acgctgatgg aactgaagtg gaccagtaag gcgctttctg atttggcgcg gttatatgat    2700
tttctggtgc tgaccagtaa acctgcggcc gccagaacgg tgcagtccct gacacatgct    2760
ccggtcattc tgttaactca tccacgtatg ggagaacagt tgtttaagct cagctgtcag    2820
ttagttgccg tttgagaacg gaaacgggca aagataaaga tgaccgcgaa gcagagtgcg    2880
gggatcagtt cagcagtggg gatgttgccc gccgcgtcac tgacaaaacc catgaccgga    2940
gtgacaatac cgccgccaat aatggtcata acgatgaagg acgaaccata tttggtgtcc    3000
tggccgagat tcttaatgcc cagcgagaag attgttgggt actgaatcga cataaaggcg    3060
ctgcataaag tcagggctat taagcccaca tgaccgccag cgaaggctga gatcaggcac    3120
agtgccatag cgattaatgc gtaggcggcc aggactttgt gtggtgcgaa gcgactgatg    3180
agccaggtac cggtgaaacg accaataaag aagcacacca tggttccggt taaatagtta    3240
gcggcaaagc ctgcagtcat acctggaatt tcttctacag cgtagcgaat caaatagctc    3300
cagcaggcca tttgtgcgcc gacatagcag aattgcgcta ataccgccca cgccagtgg    3360 cgaatacgcg ccaggcgaga aagcgatgcg gagaacgatc cttgtttggc gtcactgtga    3420
ttatcactct gcaatgccgg gaatttcgtc agcatgatca gcagggcgac cagtaacacg    3480
atagccacga tgatcatata aggtgtctgt accgataata ccaggctgtg tttatacgca    3540
ctcaattgct ctgagacat tttatcgaga acgtcttgcg attgatgtgg cacgttagac    3600
aaaataagac tttgcccaaa gacaaccgcg ataattgcgc caaacgagtt aaatgtttgc    3660
gcaagattta agcggaagtg accactactt tccggcccta ataccgtaac aaaagggttt    3720
gcggcagttt ccagacaacc taatccggct gcaataataa ataggccaac taaaaacaag    3780
gtgtagttca ttatttctgc ggcgggccag aataatgcag cacccaaggc atataaaaat    3840
aacccggtaa taatccctgc tttataactg agttttttca tcaatatccc agcagggatt    3900
gggataatga aataaccaaa gtaaaaggcc gattggatca ggccagcctg gaaatttgtc    3960
agcgtaaaag cctgctggaa ttgaggtaat aaaatgtcgt taaggttatt ggctaccgcc    4020
caaagaaaaa acagtgagca cagcagcgcg aatggaataa tgtaacttct gctttgccct    4080
gcatctttat ctaccgcacg gtaactctgc gtttgtattg atgtgtttcc catagcttgg    4140
ttacctccgg gaaacgcggt tgatttgttt agtggttgaa ttatttgctc aggatgtggc    4200
atagtcaagg gcgtgacggc tcgcctgact tctcgttcca gtgcccccgt ccgacagtcg    4260
agcgtgcgag cccataatct cgcgctggtg ctgcataccg tggcaaacag cacagatcgc    4320
ctagggaatt cggcactggc cgtcgtttta caacgtcgtg actgggaaaa ccctggcgtt    4380
acccaactta atcgccttgc agcacatccc ctttcgcca gctggcgtaa tagcgaagag    4440
gcccgcaccg atcgcccttc ccaacagttg cgcagcctga atggcgaatg gcgcgataag    4500
ctagcttcac gctgccgcaa gcactcaggg cgcaagggct gctaaaggaa gcggaacacg    4560
```

```
tagaaagcca gtccgcagaa acggtgctga ccccggatga atgtcagcta ctgggctatc    4620
tggacaaggg aaaacgcaag cgcaaagaga aagcaggtag cttgcagtgg gcttacatgg    4680
cgatagctag actgggcggt tttatggaca gcaagcgaac cggaattgcc agctggggcg    4740
ccctctggta aggttgggaa gccctgcaaa gtaaactgga tggctttctt gccgccaagg    4800
atctgatggc gcaggggatc aagatctgat caagagacag gatgaggatc gtttcgcatg    4860
attgaacaag atggattgca cgcaggttct ccggccgctt gggtggagag gctattcggc    4920
tatgactggg cacaacagac aatcggctgc tctgatgccg ccgtgttccg gctgtcagcg    4980
caggggcgcc cggttctttt tgtcaagacc gacctgtccg gtgccctgaa tgaactccaa    5040
gacgaggcag cgcggctatc gtggctggcc acgacgggcg ttccttgcgc agctgtgctc    5100
gacgttgtca ctgaagcggg aagggactgg ctgctattgg gcgaagtgcc ggggcaggat    5160
ctcctgtcat ctcaccttgc tcctgccgag aaagtatcca tcatggctga tgcaatgcgg    5220
cggctgcata cgcttgatcc ggctacctgc ccattcgacc accaagcgaa acatcgcatc    5280
gagcgagcac gtactcggat ggaagccggt cttgtcgatc aggatgatct ggacgaagag    5340
catcaggggc tcgcgccagc cgaactgttc gccaggctca aggcgcggat gcccgacggc    5400
gaggatctcg tcgtgaccca tggcgatgcc tgcttgccga atatcatggt ggaaaatggc    5460
cgcttttctg gattcatcga ctgtggccgg ctgggtgtgg cggaccgcta tcaggacata    5520
gcgttggcta cccgtgatat tgctgaagag cttggcggcg aatgggctga ccgcttcctc    5580
gtgctttacg gtatcgccgc tcccgattcg cagcgcatcg ccttctatcg ccttcttgac    5640
gagttcttct gagcgggact ctggggttcg cgatgataag ctgtcaaaca tgagaattac    5700
aacttatatc gtatggggct gacttcaggt gctacatttg aagagataaa ttgcactgaa    5760
atctagaaat                                                            5770

<210> SEQ ID NO 62
<211> LENGTH: 109
<212> TYPE: DNA
<213> ORGANISM: Artificial Sequence
<220> FEATURE:
<223> OTHER INFORMATION: Synthetic Linker

<400> SEQUENCE: 62
actgacaatc cgttaccggt gccacgctga tggaactgaa gtggaccagt aaggcgcttt    60
ctgatttggc gcggttatat gattttctgg tgctgaccag taaacctgc                109

<210> SEQ ID NO 63
<211> LENGTH: 5695
<212> TYPE: DNA
<213> ORGANISM: Artificial Sequence
<220> FEATURE:
<223> OTHER INFORMATION: Primer

<400> SEQUENCE: 63
gtgaccggcg agcagagcct gcgcatgcac atgtctctgc atccttttta cgtgcagaaa    60
cgaacgtatg ccggtcgcaa atatgctttc cgtccggaaa acaacgcct cctcgatgcc    120 atctggccgg ttctggtcag cttcagtgat gcgggcacac ataccgtagg catgagtgtt    180
tcccgtctgg ccagagaaat cagcccgaaa gacagcaagg gaaggttat tccggaactg    240 gaagtgacgg tctcccgcct ttccgtttg ctggccgaac aggtacgttt tggtgtgctg    300
ggtgtttcag aggaaaccct gtgggaccgt gaaacccgcc agcgtctgcc acgttacgtc    360
tggataacac cggcaggctg gcagatgctg ggcgtcgaca tggtaaaact tcacgaacag    420
```

```
cagcagaaac gactgcgtga aagtgaaatc cgccagcagc tcattcggga aggtgttctg    480
cgtgaggatg aagatatctc cgtacatgcg gccagaaaac gctggtatct gcagcgcagc    540
caggatgcac tgaaacaccg tcgtgcaaaa gcggcagcca gtaagcgcgc cagacgcctg    600
aagaaactgc ctgccgacca gcagattcat gagatggcag agtatctcag gaagcgtctg    660
cctccggatg aagcctattt ttgttccgat gaccatctga agcgaatggc catcagggag    720
ttgcgtcagc ttgaactgac gctggctgcc ccgccaccgc actagacagc accattccct    780
cagcactgaa tcatcaccag cccctccggg gctttcggcg ctggttccgc tcagcccaaa    840
atccgcagta atcaccttaa atcccctcag aggggcatat ctgcccataa aaccacgcat    900
cagtcatcag aacatggcca cgtcgtttca gttatccaca taaatccgca aacaaagaac    960
tttaagaagc tgcaaacctg aaacagcaaa cctgcaatat agtcttaacc ccattattta   1020
atccctgcg ttgcttcgcc gcagggaaaa tctttatctc tgagaccact gtgaacaaat    1080
acaaagaggc cttcgcttgc agcggccaag gccgcgccgc tcagaatcta aaagcacctc   1140
ccacgctgat gcgcgggccc cgaacctcac cgttctgaaa ccacaacaaa aaacatcag    1200
gaataaaaac accacacaaa cgcagcaccg tacccacccc tcataactga aaagcgaggc   1260
cgcccccgcc cgaagggcgg gaacaacatc gcttttaatt atgaatgttg taactacatt   1320
gtcatcgctg ccagtcttct ggctggaagt cctcagtaca cgctcgtaag cggccctgac   1380
ggcccgctaa cgcggagata cgccccgact gcgggtaaac ccttgtcggg accactccga   1440
ccgcgcacag aagctatttc atggctgaag cgggtatggc ttagcaggat ggggatgggt   1500
aaggtgaaat ctatcaatca gtaccggctg acgccgggct tcggcggttt tgtttctgtg   1560
ccatatgtaa caacggagtg ccgccttaca tgcgctgacg cgcattattt gccttgtttc   1620
gtctgaaagt aatcactatg attaaatatg attaacagct aatcggatat gcaaatgaaa   1680
aacaataccg cacaagcaac aaaagtaatt accgcgcatg tgccattacc tatggctgat   1740
aaagtcgacc agatggccgc cagactggaa cgctcccggg gctggattat caaacaggcg   1800
ctttctgcat ggcttgccca ggaggaggag cgtaatcgcc tgacgctgga agccctggac   1860
gatgtgacat ccggacaggt tatcgaccat caggctgtac aggcctgggc ggacagcctc   1920
agtactgttt aaacgtaagg cgcttttctga tttgggcggc cgccagaacg gtgcagtccc   1980
tgacacatgc tccggtcatt ctgttaactc atccacgtat gggagaacag ttgtttaagc   2040
tcagctgtca gttagttgcc gtttgagaac ggaaacgggc aaagataaag atgaccgcga   2100
agcagagtgc ggggatcagt tcagcagtgg ggatgttgcc cgccgcgtca ctgacaaaac   2160
ccatgaccgg agtgacaata ccgccgccaa taatggtcat aacgatgaag gacgaaccat   2220
atttggtgtc ctggccgaga ttcttaatgc ccagcgagaa gattgttggg tactgaatcg   2280
acataaaggc gctgcataaa gtcagggcta ttaagcccac atgaccgcca gcgaaggctg   2340
agatcaggca cagtgccata gcgattaatg cgtaggcggc caggactttg tgtggtgcga   2400
agcgactgat gagccaggta ccggtgaaac gaccaataaa gaagcacacc atggttccgg   2460
ttaaatagtt agcggcaaag cctgcagtca tacctggaat tcttctaca gcgtagcgaa    2520
tcaaatagct ccagcaggcc gtttgtgcgc cgacatagca gaattgcgct aataccgccc   2580
agcgccagtg gcgaatacgc gccaggcgag aaagcgatgc ggagaacgat ccttgtttgg   2640
cgtcactgtg attatcactc tgcaatgccg ggaatttcgt cagcatgatc agcagggcga   2700
ccagtaacac gatagccacg atgatcatat aaggtgtctg taccgataat accaggctgt   2760
gtttatacgc actcaattgc tctggagaca ttttatcgag aacgtcttgc gattgatgtg   2820
```

```
gcacgttaga caaaataaga ctttgcccaa agacaaccgc gataattgcg ccaaacgagt   2880
taaatgtttg cgcaagattt aagcggaagt gaccactact ttccggccct aataccgtaa   2940
caaaagggtt tgcggcagtt tccagacaac ctaatccggc tgcaataata aataggccaa   3000
ctaaaaacaa ggtgtagttc attatttctg cggcgggcca gaataatgca gcacccaagg   3060
catataaaaa taacccggta ataatccctg ctttataact gagttttttc atcaatatcc   3120
cagcagggat tgggataatg aaataaccaa agtaaaaggc cgattggatc aggccagcct   3180
ggaaatttgt cagcgtaaaa gcctgctgga attgaggtaa taaaatgtcg ttaaggttat   3240
tggctaccgc ccaaagaaaa aacagtgagc acagcagcgc gaatggaata atgtaacttc   3300
tgctttgccc tgcatcttta tctaccgcac ggtaactctg cgtttgtatt gatgtgtttc   3360
ccatagcttg gttacctccg ggaaacgcgg ttgatttgtt tagtggttga attatttgct   3420
caggatgtgg cattgtcaag ggcgtgacgg ctcgcctgac ttctcgttcc agtgcccccg   3480
tccgacagtc gagcgtgcga gcccataatc tcgcgctggt gctgcatacc gtggcaaaca   3540
gcacagatcg cctagggaat tcggcactgg ccgtcgtttt acaacgtcgt gactgggaaa   3600
accctggcgt tacccaactt aatcgccttg cagcacatcc ccctttcgcc agctggcgta   3660
atagcgaaga ggcccgcacc gatcgccctt cccaacagtt gcgcagcctg aatggcgaat   3720
ggcgcgataa gctagcttca cgctgccgca agcactcagg gcgcaagggc tgctaaagga   3780
agcggaacac gtagaaagcc agtccgcaga acggtgctg accccggatg aatgtcagct   3840
actgggctat ctggacaagg gaaaacgcaa gcgcaaagag aaagcaggta gcttgcagtg   3900
ggcttacatg gcgatagcta gactgggcgg ttttatggac agcaagcgaa ccggaattgc   3960
cagctggggc gccctctggt aaggttggga agccctgcaa agtaaactgg atggcttttct  4020 tgccgccaag gatctgatgg cgcaggggat caagatctga tcaagagaca ggatgaggat   4080
cgtttcgcat gattgaacaa gatggattgc acgcaggttc tccggccgct tgggtggaga   4140
ggctattcgg ctatgactgg gcacaacaga caatcggctg ctctgatgcc gccgtgttcc   4200
ggctgtcagc gcaggggcgc ccggttcttt ttgtcaagac cgacctgtcc ggtgccctga   4260
atgaactcca agacgaggca gcgcggctat cgtggctggc cacgacgggc gttccttgcg   4320
cagctgtgct cgacgttgtc actgaagcgg gaagggactg gctgctattg ggcgaagtgc   4380
cggggcagga tctcctgtca tctcaccttg ctcctgccga gaaagtatcc atcatggctg   4440
atgcaatgcg gcggctgcat acgcttgatc cggctacctg cccattcgac caccaagcga   4500
aacatcgcat cgagcgagca cgtactcgga tggaagccgg tcttgtcgat caggatgatc   4560
tggacgaaga gcatcagggg ctcgcgccag ccgaactgtt cgccaggctc aaggcgcgga   4620
tgcccgacgg cgaggatctc gtcgtgaccc atggcgatgc ctgcttgccg aatatcatgg   4680
tggaaaatgg ccgcttttct ggattcatcg actgtggccg ctgggtgtg gcggaccgct   4740 atcaggacat agcgttggct acccgtgata ttgctgaaga gcttggcggc gaatgggctg   4800
accgcttcct cgtgctttac ggtatcgccg ctcccgattc gcagcgcatc gccttctatc   4860
gccttcttga cgagttcttc tgagcgggac tctggggttc gcgatgataa gctgtcaaac   4920
atgagaatta caacttatat cgtatggggc tgacttcagg tgctacattt gaagagataa   4980
attgcactga aatctagaaa taaaaataga ttttatttt ttgatgcagg tcaagattga   5040
ctcattagag gtatcggtga ggagacactg gaagagaaga gatcgttgta atgcttttca   5100
aattaacgta aagcgggtat atttcggttg ttattagctg cgcagagggt ggcactctgt   5160
ggagcaaagc ggcgaaagcc ggacggcaga atgcgccata aggcattcag gagagatggc   5220
```

-continued

```
atttacgggc agtaagtcag aagaccgaag atgttccgga agccataaaa ggaaaacccc    5280
cacaatcttt cgacgaactt ggcgggacgg agaaagatta tgggggcctc acagaatacg    5340
ggtaaagtat aatgaaaccg taccagagat tcaaccctgt gcagtgtata aatacacggc    5400
acaatcgctc cgccataagc gacagcttgt ggcaggtctg aagaatactc catataacgc    5460
agtacactgg agtcagttag cacccgaaga gcagatccgt ttctgggaag actatgaagc    5520
gggaagggcg accactttcc tggttgaacc ggaaaggaag cgcacgaagc gccgtcgcgg    5580
tgagcactcc accaaaccca aatgcgaaaa tccgtcctgg tatcgtcctg agcgctataa    5640
ggcgctgagc gggcagctcg ggcacgccta caaccgtctg gtgaaaaagg acccg         5695
```

<210> SEQ ID NO 64
<211> LENGTH: 7886
<212> TYPE: DNA
<213> ORGANISM: Artificial Sequence
<220> FEATURE:
<223> OTHER INFORMATION: Plasmid

<400> SEQUENCE: 64

```
gtgaccggcg agcagagcct gcgcatgcac atgtctctgc atccttttta cgtgcagaaa      60
cgaacgtatg ccggtcgcaa atatgctttc cgtccggaaa acaacgcct cctcgatgcc     120 atctggccgt ttctggtcag cttcagtgat gcgggcacac ataccgtagg catgagtgtt     180
tcccgtctgg ccagagaaat cagcccgaaa gacagcaagg ggaaggttat tccggaactg     240
gaagtgacgg tctcccgcct ttcccgtttg ctggccgaac aggtacgttt tggtgtgctg     300
ggtgtttcag aggaaaccct gtgggaccgt gaaacccgcc agcgtctgcc acgttacgtc     360
tggataacac cggcaggctg gcagatgctg ggcgtcgaca tggtaaaact tcacgaacag     420
cagcagaaac gactgcgtga agtgaaatc cgccagcagc tcattcggga aggtgttctg     480
cgtgaggatg aagatatctc cgtacatgcg gccagaaaac gctggtatct gcagcgcagc     540
caggatgcac tgaaacaccg tcgtgcaaaa gcggcagcca gtaagcgcgc cagacgcctg     600
aagaaactgc ctgccgacca gcagattcat gagatggcag agtatctcag gaagcgtctg     660
cctccggatg aagcctattt tgttccgat gaccatctga agcgaatggc catcagggag     720
ttgcgtcagc ttgaactgac gctggctgcc ccgccaccgc actagacagc accattccct     780
cagcactgaa tcatcaccag cccctccggg gctttcggcg ctggttccgc tcagcccaaa     840
atccgcagta atcaccttaa atccctcag agggggcatat ctgcccataa accacgcat     900 cagtcatcag aacatggcca cgtcgtttca gttatccaca taaatccgca acaaagaac     960 tttaagaagc tgcaaacctg aaacagcaaa cctgcaatat agtcttaacc ccattattta    1020 atccctgcg ttgcttcgcc gcagggaaaa tctttatctc tgagaccact gtgaacaaat    1080 acaagaggc cttcgcttgc agcggccaag gccgcgccgc tcagaatcta aaagcacctc    1140
ccacgctgat gcgcgggccc cgaacctcac cgttctgaaa ccacaacaaa aaacatcag    1200 gaataaaaac accacacaaa cgcagcaccg tacccacccc tcataactga aaagcgaggc    1260
cgcccccgcc cgaagggcgg gaacaacatc gctttttaat tatgaatgttg taactacatt    1320 gtcatcgctg ccagtcttct ggctggaagt cctcagtaca cgctcgtaag cggccctgac    1380
ggcccgctaa cgcggagata cgccccgact gcgggtaaac ccttgtcggg accactccga    1440
ccgcgcacag aagctatttc atggctgaag cgggtatggc ttagcaggat ggggatgggt    1500
aaggtgaaat ctatcaatca gtaccggctg acgccgggct tcggcggttt tgtttctgtg    1560
ccatatgtaa caacggagtg ccgccttaca tgcgctgacg cgcattattt gccttgtttc    1620
```

```
gtctgaaagt aatcactatg attaaatatg attaacagct aatcggatat gcaaatgaaa   1680
aacaataccg cacaagcaac aaaagtaatt accgcgcatg tgccattacc tatggctgat   1740
aaagtcgacc agatggccgc cagactggaa cgctcccggg gctggattat caaacaggcg   1800
ctttctgcat ggcttgccca ggaggaggag cgtaatcgcc tgacgctgga agccctggac   1860
gatgtgacat ccggacaggt tatcgaccat caggctgtac aggcctgggc ggacagcctc   1920
agtactgttt aaacttacga tggcatcgcg atagcctgct tctcttcaag cagcttctcg   1980
actacgccag gatcggcaag cgtcgaggta tcgcccaggt tgctggtatc gcccgccgca   2040
attttgcgca gaatacggcg cataattttg ccggagcggg ttttaggcag ggagtcggtc   2100
cagtgcagca cgtctggcgt cgccagcggg ccaatctctt tacgcaccca gttgcggact   2160
tctgcgtaca gttctggtga cggttcctcc ccgtgattaa gcgtgacgta ggcgtagatc   2220
gcctgacctt taatattgtg cggaataccf actacggcgg cttcggcaat cttcggatgc   2280
gccaccagcg ccgactcaat ctctgccgtc ccagacggt gaccggagac gttcagcacg   2340
tcgtccacac gcccggttat ccagtaatag ccatcttcat cgcgacgcgc gccgtcgccg   2400
ctgaaataca tattttttgaa ggtggagaag taggtctgtt caaaacgttc gtgatcgcca   2460
aacagcgtac gcgcctgacc cggccaggag tcggtgatta ccaggctacc ttcggtggcc   2520
ccctccagcg ggttaccttc gttatcgacc agcgccggtt gcacgccgaa gaacggacgt   2580
gttgccgaac cggctttcag ctcggtagcg ccaggcagcg gggtgatcat gaaaccgccg   2640
gtttcggtct gccaccaggt atcgaccacc ggacatttct cgttgccgat ttttttccag   2700
taccactccc acgcttccgg gttaattggc tcgcccacgg aaccgagaat gcgcagcgac   2760
gaacggtcgg tgccttcgat cgctttatcg ccttccgcca tcagcgcgcg gatcgccgtg   2820
ggtgcggtat agagaatatt gacctgatgc ttgtccacca cctgcgccat acgggcaggc   2880
gtcggccagt tgggtacgcc ttcaaacatc agcgtggtcg caccgcaggc cagcgggccg   2940
tacagcaagt aactgtgtcc ggtcacccag cccacatcgg cggtgcacca gtagatatca   3000
cccggatgat aatcaaagac atatttaaag gtcagcgccg cgtacaccag ataaccgccg   3060
gtagtatgca gcacacccttt tggcttaccg gtagaaccgg aggtgtagag aataaacagc   3120
ggatcttcgg cgttcatctc ttccgcctgg tgctgatcgc tcgcttgctc aaccaggtcg   3180
tgccaccaca ggtcgcgccc ttcctgccag tcaattttcc cgccagtacg cttcagtacc   3240
accacatgct ctacgctggt gacgttcggg tttttcagcg cgtcatcaac gttttttcttc   3300 agcggaatac tgcgcccggc acgcacacct tcgtcggaag tgatcaccag tcgtgagttg   3360
gaatcaataa tgcgcccggc aacggcttcc ggcgagaagc cgccgaaaat caccgaatgc   3420
accgcgccaa tgcgggcgca ggccagcatc gcaaccgcgg cttccggcac catcggcata   3480
taaatcgcca ccacatcacc ttttttaatg cccagctcga gcagggtatt ggcgaagcgg   3540
cagacgtcgc ggtgcagctc tttatagctg atatgtttgc tctggctggc gtcgtcgcct   3600
tcccagatga tggcggtacg atcgccgttt tcttgcagat ggcggtcaag gcagtttgcc   3660
gccagattca gcgtgccgtc ctcgtaccat ttaatggaca cattaccggg ggcaaaggag   3720
gtgtttttca ccttctggta aggtttgatc cagtcaagaa ttttttccctg ttcgccccag   3780 aaggtatcag gtacgttaat agattgttga tacatcgcct cgtactgctg agggtttatc   3840
aggcaacggt ctgcgatgtt ggcaggaatg gtgtgttgt gaatttggct cattttagct   3900
tcctagcctc ctgaaaatct cgataactca aaaaatacgc ccggtagtga tcttatttca   3960
ttatggtgaa agttggaacc tcttacgtgc cgatcaacgt ctcattttcg ccaaaagttg   4020
```

-continued

```
gcccagggct tcccggtatc aacagggaca ccaggattta tttattctgc gaagtgatct    4080
tccgtcacag gtatttattc ggcgcaaagg gcctcgtgat acgcctattt ttataggtta    4140
atgtcagcgg ccgccagaac ggtgcagtcc ctgacacatg ctccggtcat tctgttaact    4200
catccacgta tgggagaaca gttgtttaag ctcagctgtc agttagttgc cgtttgagaa    4260
cggaaacggg caaagataaa gatgaccgcg aagcagagtg cggggatcag ttcagcagtg    4320
gggatgttgc ccgccgcgtc actgacaaaa cccatgaccg gagtgacaat accgccgcca    4380
ataatggtca taacgatgaa ggacgaacca tatttggtgt cctggccgag attcttaatg    4440
cccagcgaga agattgttgg gtactgaatc gacataaagg cgctgcataa agtcagggct    4500
attaagccca catgaccgcc agcgaaggct gagatcaggc acagtgccat agcgattaat    4560
gcgtaggcgg ccaggacttt gtgtggtgcg aagcgactga tgagccaggt accggtgaaa    4620
cgaccaataa agaagcacac catggttccg gttaaatagt tagcggcaaa gcctgcagtc    4680
atacctggaa tttcttctac agcgtagcga atcaaatagc tccagcaggc cgtttgtgcg    4740
ccgacatagc agaattgcgc taataccgcc cagcgccagt ggcgaatacg cgccaggcga    4800
gaaagcgatg cggagaacga tccttgtttg gcgtcactgt gattatcact ctgcaatgcc    4860
gggaatttcg tcagcatgat cagcagggcg accagtaaca cgatagccac gatgatcata    4920
taaggtgtct gtaccgataa taccaggctg tgtttatacg cactcaattg ctctggagac    4980
attttatcga gaacgtcttg cgattgatgt ggcacgttag acaaaataag actttgccca    5040
aagacaaccg cgataattgc gccaaacgag ttaaatgttt gcgcaagatt taagcggaag    5100
tgaccactac tttccggccc taataccgta acaaagggt tgcggcagt ttccagacaa    5160 cctaatccgg ctgcaataat aaataggcca actaaaaaca aggtgtagtt cattatttct    5220
gcggcgggcc agaataatgc agcacccaag gcatataaaa ataacccggt aataatccct    5280
gctttataac tgagttttt catcaatatc ccagcaggga ttgggataat gaaataacca    5340
aagtaaaagg ccgattggat caggccagcc tggaaatttg tcagcgtaaa agcctgctgg    5400
aattgaggta ataaaatgtc gttaaggtta ttggctaccg cccaaagaaa aaacagtgag    5460
cacagcagcg cgaatggaat aatgtaactt ctgctttgcc ctgcatcttt atctaccgca    5520
cggtaactct gcgtttgtat tgatgtgttt cccatagctt ggttacctcc gggaaacgcg    5580
gttgatttgt ttagtggttg aattatttgc tcaggatgtg gcattgtcaa gggcgtgacg    5640
gctcgcctga cttctcgttc cagtgccccc gtccgacagt cgagcgtgcg agcccataat    5700
ctcgcgctgg tgctgcatac cgtggcaaac agcacagatc gcctagggaa ttcggcactg    5760
gccgtcgttt tacaacgtcg tgactgggaa aaccctggcg ttacccaact taatcgcctt    5820
gcagcacatc ccccttcgc cagctggcgt aatagcgaag aggcccgcac cgatcgccct    5880
tcccaacagt tgcgcagcct gaatggcgaa tggcgcgata gctagcttc acgctgccgc    5940 aagcactcag ggcgcaaggg ctgctaaagg aagcggaaca cgtagaaagc cagtccgcag    6000
aaacggtgct gaccccggat gaatgtcagc tactgggcta tctggacaag gaaaacgca    6060 agcgcaaaga gaaagcaggt agcttgcagt gggcttacat ggcgatagct agactgggcg    6120
gttttatgga cagcaagcga accggaattg ccagctgggg cgccctctgg taaggttggg    6180
aagccctgca aagtaaactg gatggctttc ttgccgccaa ggatctgatg gcgcagggga    6240
tcaagatctg atcaagagac aggatgagga tcgtttcgca tgattgaaca agatggattg    6300
cacgcaggtt ctccggccgc ttgggtggag aggctattcg gctatgactg gcacaacag    6360 acaatcggct gctctgatgc cgccgtgttc cggctgtcag cgcaggggcg cccggttctt    6420
```

```
tttgtcaaga ccgacctgtc cggtgccctg aatgaactcc aagacgaggc agcgcggcta    6480
tcgtggctgg ccacgacggg cgttccttgc gcagctgtgc tcgacgttgt cactgaagcg    6540
ggaagggact ggctgctatt gggcgaagtg ccggggcagg atctcctgtc atctcaccttt   6600 gctcctgccg agaaagtatc catcatggct gatgcaatgc ggcggctgca tacgcttgat    6660
ccggctacct gcccattcga ccaccaagcg aaacatcgca tcgagcgagc acgtactcgg    6720
atggaagccg tcttgtcga tcaggatgat ctggacgaag agcatcaggg gctcgcgcca    6780
gccgaactgt tcgccaggct caaggcgcgc atgcccgacg cgaggatct cgtcgtgacc    6840 catgcgatg cctgcttgcc gaatatcatg gtggaaaatg gccgcttttc tggattcatc     6900
gactgtggcc ggctgggtgt ggcggaccgc tatcaggaca tagcgttggc tacccgtgat    6960
attgctgaag agcttggcgg cgaatgggct gaccgcttcc tcgtgcttta cggtatcgcc    7020
gctcccgatt cgcagcgcat cgccttctat cgccttcttg acgagttctt ctgagcggga    7080
ctctggggtt cgcgatgata agctgtcaaa catgagaatt acaacttata tcgtatgggg    7140
ctgacttcag gtgctacatt tgaagagata aattgcactg aaatctagaa ataaaaatag    7200 atttatttt tttgatgcag gtcaagattg actcattaga ggtatcggtg aggagacact      7260
ggaagagaag agatcgttgt aatgcttttc aaattaacgt aaagcgggta tatttcggtt    7320
gttattagct gcgcagaggg tggcactctg tggagcaaag cggcgaaagc cggacggcag    7380
aatgcgccat aaggcattca ggagagatgg catttacggg cagtaagtca gaagaccgaa    7440
gatgttccgg aagccataaa aggaaaaccc ccacaatctt tcgacgaact ggcgcggacg     7500
gagaaagatt atgggggcct cacagaatac gggtaaagta taatgaaacc gtaccagaga    7560
ttcaaccctg tgcagtgtat aaatacacgg cacaatcgct ccgccataag cgacagcttg     7620
tggcaggtct gaagaatact ccatataacg cagtacactg gagtcagtta gcacccgaag     7680
agcagatccg tttctgggaa gactatgaag cgggaagggc gaccactttc ctggttgaac    7740
cggaaaggaa gcgcacgaag cgccgtcgcg gtgagcactc caccaaaccc aaatgcgaaa    7800
atccgtcctg gtatcgtcct gagcgctata aggcgctgag cgggcagctc gggcacgcct    7860
acaaccgtct ggtgaaaaag gacccg                                          7886

<210> SEQ ID NO 65
<211> LENGTH: 7790
<212> TYPE: DNA
<213> ORGANISM: Artificial Sequence
<220> FEATURE:
<223> OTHER INFORMATION: Plasmid

<400> SEQUENCE: 65
gtgaccggcg agcagagcct gcgcatgcac atgtctctgc atccttttta cgtgcagaaa      60
cgaacgtatg ccggtcgcaa atatgctttc cgtccggaaa acaacgcct cctcgatgcc      120 atctggccgg ttctggtcag cttcagtgat gcgggcacac ataccgtagg catgagtgtt     180
tcccgtctgg ccagagaaat cagcccgaaa gacagcaagg ggaaggttat tccggaactg     240
gaagtgacgg tctcccgcct ttcccgtttg ctggccgaac aggtacgttt tggtgtgctg    300
ggtgtttcag aggaaaccct gtgggaccgt gaaacccgcc agcgtctgcc acgttacgtc     360
tggataacac cggcaggctg gcagatgctg gcgtcgaca tggtaaaact tcacgaacag     420
cagcagaaac gactgcgtga agtgaaatc gccagcagc tcattcggga aggtgttctg      480
cgtgaggatg aagatatctc cgtacatgcg gccagaaaac gctggtatct gcagcgcagc    540
caggatgcac tgaaacaccg tcgtgcaaaa gcggcagcca gtaagcgcgc cagacgcctg    600
```

```
aagaaactgc ctgccgacca gcagattcat gagatggcag agtatctcag gaagcgtctg    660
cctccggatg aagcctattt ttgttccgat gaccatctga agcgaatggc catcagggag    720
ttgcgtcagc ttgaactgac gctggctgcc ccgccaccgc actagacagc accattccct    780
cagcactgaa tcatcaccag cccctccggg gctttcggcg ctggttccgc tcagcccaaa    840
atccgcagta atcaccttaa atcccctcag aggggcatat ctgcccataa aaccacgcat    900
cagtcatcag aacatggcca cgtcgtttca gttatccaca taaatccgca aacaaagaac    960
tttaagaagc tgcaaacctg aaacagcaaa cctgcaatat agtcttaacc ccattattta   1020
atcccctgcg ttgcttcgcc gcagggaaaa tctttatctc tgagaccact gtgaacaaat   1080
acaaagaggc cttcgcttgc agcggccaag gccgcgccgc tcagaatcta aaagcacctc   1140
ccacgctgat gcgcgggccc cgaacctcac cgttctgaaa ccacaacaaa aaaacatcag   1200
gaataaaaac accacacaaa cgcagcaccg tacccacccc tcataactga aaagcgaggc   1260
cgcccccgcc cgaagggcgg gaacaacatc gcttttaatt atgaatgttg taactacatt   1320
gtcatcgctg ccagtcttct ggctggaagt cctcagtaca cgctcgtaag cggccctgac   1380
ggcccgctaa cgcggagata cgccccgact gcgggtaaac ccttgtcggg accactccga   1440
ccgcgcacag aagctatttc atggctgaag cgggtatggc ttagcaggat ggggatgggt   1500
aaggtgaaat ctatcaatca gtaccggctg acgccgggct tcggcggttt tgtttctgtg   1560
ccatatgtaa caacggagtg ccgccttaca tgcgctgacg cgcattattt gccttgtttc   1620
gtctgaaagt aatcactatg attaaatatg attaacagct aatcggatat gcaaatgaaa   1680
aacaataccg cacaagcaac aaaagtaatt accgcgcatg tgccattacc tatggctgat   1740
aaagtcgacc agatggccgc cagactgaaa cgctcccggg gctggattat caaacaggcg   1800 cttttctgcat ggcttgccca ggaggaggag cgtaatcgcc tgacgctgga agccctggac   1860
gatgtgacat ccggacaggt tatcgaccat caggctgtac aggcctgggc ggacagcctc   1920
agtactgttt aaacttacga tggcatcgcg atagcctgct tctcttcaag cagcttctcg   1980
actacgccag gatcggcaag cgtcgaggta tcgcccaggt tgctggtatc gcccgccgca   2040
attttgcgca gaatacggcg cataattttg ccggagcggg ttttaggcag ggagtcggtc   2100
cagtgcagca cgtctggcgt cgccagcggg ccaatctctt tacgcaccca gttgcggact   2160
tctgcgtaca gttctggtga cggttcctcc ccgtgattaa gcgtgacgta ggcgtagatc   2220
gcctgacctt taatattgtg cggaatacct actacggcgg cttcggcaat cttcggatgc   2280
gccaccagcg ccgactcaat ctctgccgtc cccagacggt gaccggagac gttcagcacg   2340
tcgtccacac gcccggttat ccagtaatag ccatcttcat cgcgacgcgc gccgtcgccg   2400
ctgaaataca tatttttgaa ggtggagaag taggtctgtt caaaacgttc gtgatcgcca   2460
aacagcgtac gcgcctgacc cggccaggag tcggtgatta ccaggctacc ttcggtggcc   2520
ccctccagcg ggttaccttc gttatcgacc agcgccggtt gcacgccgaa gaacggacgt   2580
gttgccgaac cggctttcag ctcggtagcg ccaggcagcg gggtgatcat gaaaccgccg   2640
gtttcggtct gccaccaggt atcgaccacc ggacatttct cgttgccgat ttttttccag   2700
taccactccc acgcttccgg gttaattggc tcgcccacgg aaccgagaat gcgcagcgac   2760
gaacggtcgg tgccttcgat cgctttatcg ccttccgcca tcagcgcgcg gatcgccgtg   2820
ggtgcggtat agagaatatt gacctgatgc ttgtccacca cctgcgccat acgggcaggc   2880 gtcgccagt tgggtacgcc ttcaaacatc agcgtggtcg caccgcaggc cagcgggccc   2940
tacagcaagt aactgtgtcc ggtcacccag cccacatcgg cggtgcacca gtagatatca   3000
```

```
cccggatgat aatcaaagac atatttaaag gtcagcgccg cgtacaccag ataaccgccg   3060
gtagtatgca gcacaccttt tggcttaccg gtagaaccgg aggtgtagag aataaacagc   3120
ggatcttcgg cgttcatctc ttccgcctgg tgctgatcgc tcgcttgctc aaccaggtcg   3180
tgccaccaca ggtcgcgccc ttcctgccag tcaattttcc cgccagtacg cttcagtacc   3240
accacatgct ctacgctggt gacgttcggg ttttcagcg cgtcatcaac gttttcttc     3300 agcggaatac tgcgcccggc acgcacacct tcgtcggaag tgatcaccag tcgtgagttg   3360
gaatcaataa tgcgcccggc aacggcttcc ggcgagaagc cgccgaaaat caccgaatgc   3420
accgcgccaa tgcgggcgca ggccagcatc gcaaccgcgg cttccggcac catcggcata   3480
taaatcgcca ccacatcacc ttttttaatg cccagctcga gcagggtatt ggcgaagcgg   3540
cagacgtcgc ggtgcagctc tttatagctg atatgtttgc tctggctggc gtcgtcgcct   3600
tcccagatga tggcggtacg atcgccgttt tcttgcagat ggcggtcaag gcagtttgcc   3660
gccagattca gcgtgccgtc ctcgtaccat ttaatggaca cattaccggg ggcaaaggag   3720 gtgttttca ccttctggta aggtttgatc cagtcaagaa ttttcccctg ttcgccccag    3780
aaggtatcag gtacgttaat agattgttga tacatcgcct cgtactgctg agggtttatc   3840
aggcaacggt ctgcgatgtt ggcaggaatg gtgtgtttgt gaatttggct catatgagtt   3900
aatttctcct ctttaatgaa ttctgtgtga aattgttatc cgctcacaat tgaatctatt   3960
ataattgtta tccgctcaca aagcaaataa atttttatg atttctcgag gtgaagacga    4020
aagggcctcg tgatacgcct atttttatag gcggccgcca gaacggtgca gtccctgaca   4080
catgctccgg tcattctgtt aactcatcca cgtatgggag aacagttgtt taagctcagc   4140
tgtcagttag ttgccgtttg agaacggaaa cgggcaaaga taaagatgac cgcgaagcag   4200
agtgcgggga tcagttcagc agtggggatg ttgcccgccg cgtcactgac aaaacccatg   4260
accggagtga caataccgcc gccaataatg gtcataacga tgaaggacga accatatttg   4320
gtgtcctggc cgagattctt aatgcccagc gagaagattg ttgggtactg aatcgacata   4380
aaggcgctgc ataaagtcag ggctattaag cccacatgac cgccagcgaa ggctgagatc   4440
aggcacagtg ccatagcgat taatgcgtag gcggccagga cttgtgtgg tgcgaagcga    4500 ctgatgagcc aggtaccggt gaaacgacca ataaagaagc acaccatggt tccggttaaa   4560
tagttagcgg caaagcctgc agtcatacct ggaatttctt ctacagcgta gcgaatcaaa   4620
tagctccagc aggccgtttg tgcgccgaca tagcagaatt gcgctaatac cgcccagcgc   4680
cagtggcgaa tacgcgccag gcgagaaagc gatgcggaga acgatccttg tttggcgtca   4740
ctgtgattat cactctgcaa tgccgggaat ttcgtcagca tgatcagcag ggcgaccagt   4800
aacacgatag ccacgatgat catataaggt gtctgtaccg ataataccag gctgtgttta   4860
tacgcactca attgctctgg agacatttta tcgagaacgt cttgcgattg atgtggcacg   4920
ttagacaaaa taagactttg cccaaagaca accgcgataa ttgcgccaaa cgagttaaat   4980
gtttgcgcaa gatttaagcg gaagtgacca ctactttccg gccctaatac cgtaacaaaa   5040
gggtttgcgg cagtttccag acaacctaat ccggctgcaa taataaatag gccaactaaa   5100
aacaaggtgt agttcattat ttctgcggcg ggccagaata atgcagcacc caaggcatat   5160
aaaaataacc cggtaataat ccctgcttta taactgagtt ttttcatcaa tatcccagca   5220
gggattggga taatgaaata accaaagtaa aaggccgatt ggatcaggcc agcctggaaa   5280
tttgtcagcg taaaagcctg ctggaattga ggtaataaaa tgtcgttaag gttattggct   5340
accgcccaaa gaaaaaacag tgagcacagc agcgcgaatg gaataatgta acttctgctt   5400
```

```
tgccctgcat ctttatctac cgcacggtaa ctctgcgttt gtattgatgt gtttcccata    5460
gcttggttac ctccgggaaa cgcggttgat ttgtttagtg gttgaattat ttgctcagga    5520
tgtggcattg tcaagggcgt gacggctcgc ctgacttctc gttccagtgc ccccgtccga    5580
cagtcgagcg tgcgagccca taatctcgcg ctggtgctgc ataccgtggc aaacagcaca    5640
gatcgcctag ggaattcggc actggccgtc gttttacaac gtcgtgactg ggaaaaccct    5700
ggcgttaccc aacttaatcg ccttgcagca catccccctt tcgccagctg gcgtaatagc    5760
gaagaggccc gcaccgatcg cccttcccaa cagttgcgca gcctgaatgg cgaatgcgc    5820 gataagctag cttcacgctg ccgcaagcac tcagggcgca agggctgcta aaggaagcgg    5880
aacacgtaga aagccagtcc gcagaaacgg tgctgacccc ggatgaatgt cagctactgg    5940
gctatctgga caagggaaaa cgcaagcgca aagagaaagc aggtagcttg cagtgggctt    6000
acatggcgat agctagactg gcggtttta tggacagcaa gcgaaccgga attgccagct    6060
ggggcgccct ctggtaaggt tgggaagccc tgcaaagtaa actggatggc tttcttgccg    6120
ccaaggatct gatggcgcag gggatcaaga tctgatcaag agacaggatg aggatcgttt    6180
cgcatgattg aacaagatgg attgcacgca ggttctccgg ccgcttgggt ggagaggcta    6240
ttcggctatg actgggcaca acagacaatc ggctgctctg atgccgccgt gttccggctg    6300
tcagcgcagg ggcgcccggt tctttttgtc aagaccgacc tgtccggtgc cctgaatgaa    6360
ctccaagacg aggcagcgcg gctatcgtgg ctggccacga cgggcgttcc ttgcgcagct    6420
gtgctcgacg ttgtcactga agcgggaagg gactggctgc tattgggcga agtgccgggg    6480
caggatctcc tgtcatctca ccttgctcct gccgagaaag tatccatcat ggctgatgca    6540
atgcggcggc tgcatacgct tgatccggct acctgcccat tcgaccacca agcgaaacat    6600
cgcatcgagc gagcacgtac tcggatggaa gccggtcttg tcgatcagga tgatctggac    6660
gaagagcatc aggggctcgc gccagccgaa ctgttcgcca ggctcaaggc gcggatgccc    6720
gacggcgagg atctcgtcgt gacccatggc gatgcctgct tgccgaatat catggtggaa    6780
aatggccgct tttctggatt catcgactgt ggccggctgg gtgtggcgga ccgctatcag    6840
gacatagcgt tggctacccg tgatattgct gaagagcttg gcggcgaatg ggctgaccgc    6900
ttcctcgtgc tttacggtat cgccgctccc gattcgcagc gcatcgcctt ctatcgcctt    6960
cttgacgagt tcttctgagc gggactctgg ggttcgcgat gataagctgt caaacatgag    7020
aattacaact tatatcgtat ggggctgact tcaggtgcta catttgaaga gataaattgc    7080
actgaaatct agaaataaaa atagatttta tttttttgat gcaggtcaag attgactcat    7140
tagaggtatc ggtgaggaga cactggaaga gaagagatcg ttgtaatgct tttcaaatta    7200
acgtaaagcg ggtatatttc ggttgttatt agctgcgcag agggtggcac tctgtggagc    7260
aaagcggcga agccggacg gcagaatgcg ccataaggca ttcaggagag atggcattta    7320
cgggcagtaa gtcagaagac cgaagatgtt ccggaagcca taaaaggaaa accccacaa    7380 tctttcgacg aacttggcgg gacggagaaa gattatgggg gcctcacaga atacgggtaa    7440
agtataatga aaccgtacca gagattcaac cctgtgcagt gtataaatac acggcacaat    7500
cgctccgcca taagcgacag cttgtggcag gtctgaagaa tactccatat aacgcagtac    7560
actggagtca gttagcaccc gaagagcaga tccgttcctg ggaagactat gaagcggaa    7620 gggcgaccac tttcctggtt gaaccggaaa ggaagcgcac gaagcgccgt cgcggtgagc    7680
actccaccaa acccaaatgc gaaaatccgt cctggtatcg tcctgagcgc tataaggcgc    7740
tgagcgggca gctcgggcac gcctacaacc gtctggtgaa aaaggacccg             7790
```

<210> SEQ ID NO 66
<211> LENGTH: 100
<212> TYPE: DNA
<213> ORGANISM: Artificial Sequence
<220> FEATURE:
<223> OTHER INFORMATION: Primer

<400> SEQUENCE: 66
cgtctaccct tgttatacct cacaccgcaa ggagacgatc atgaccaata atccccttc      60 agcacagatt aagcccggcg gtgtaggctg gagctgcttc                          100

<210> SEQ ID NO 67
<211> LENGTH: 100
<212> TYPE: DNA
<213> ORGANISM: Artificial Sequence
<220> FEATURE:
<223> OTHER INFORMATION: Primer

<400> SEQUENCE: 67
gcatcaggca atgaataccc aatgcgacca gcttcttata tcagaacagc cccaacggtt     60
tatccgagta gctcaccagc catatgaata tcctccttag                          100

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
atgaccaata atccccttc ag                                               22

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
gcttcttata tcagaacagc c                                               21

<210> SEQ ID NO 70
<211> LENGTH: 17
<212> TYPE: DNA
<213> ORGANISM: Artificial Sequence
<220> FEATURE:
<223> OTHER INFORMATION: Primer

<400> SEQUENCE: 70
ccagcagccg cggtaat                                                    17

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
tgcgctttac gcccagtaat                                                 20

<210> SEQ ID NO 72
<211> LENGTH: 23

```
<212> TYPE: DNA
<213> ORGANISM: Artificial Sequence
<220> FEATURE:
<223> OTHER INFORMATION: TaqMan fluorescently labled probe
<220> FEATURE:
<221> NAME/KEY: misc_feature
<222> LOCATION: (1)..(1)
<223> OTHER INFORMATION: Labled with 6FAM(TM) fluorescein reagent
<220> FEATURE:
<221> NAME/KEY: misc_feature
<222> LOCATION: (23)..(23)
<223> OTHER INFORMATION: Labled with TAMRA
      (6-carboxytetramethylrhodamine)

<400> SEQUENCE: 72
cggagggtgc aagcgttaat cgg                                           23

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
acacaccatt cctgccaaca                                               20

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
tgttgataca tcgcctcgta ctg                                           23

<210> SEQ ID NO 75
<211> LENGTH: 24
<212> TYPE: DNA
<213> ORGANISM: Artificial Sequence
<220> FEATURE:
<223> OTHER INFORMATION: TaqMan fluorescently labled probe
<220> FEATURE:
<221> NAME/KEY: misc_feature
<222> LOCATION: (1)..(1)
<223> OTHER INFORMATION: Labeled with 6FAM(TM) fluorescein reagent
<220> FEATURE:
<221> NAME/KEY: misc_feature
<222> LOCATION: (24)..(24)
<223> OTHER INFORMATION: Labeled with TAMRA
      (6-carboxytetramethylrhodamine)

<400> SEQUENCE: 75
cgcagaccgt tgcctgataa accc                                          24

<210> SEQ ID NO 76
<211> LENGTH: 8069
<212> TYPE: DNA
<213> ORGANISM: Artificial Sequence
<220> FEATURE:
<223> OTHER INFORMATION: Plasmid

<400> SEQUENCE: 76
gtgaccggcg agcagagcct gcgcatgcac atgtctctgc atccttttta cgtgcagaaa      60
cgaacgtatg ccggtcgcaa atatgctttc cgtccggaaa aacaacgcct cctcgatgcc     120
atctggcctg ttctggtcag cttcagtgat gcgggcacac ataccgtagg catgagtgtt     180
tcccgtctgg ccagagaaat cagcccgaaa gacagcaagg ggaaggttat tccggaactg     240
```

```
gaagtgacgg tctcccgcct ttcccgtttg ctggccgaac aggtacgttt tggtgtgctg    300
ggtgtttcag aggaaaccct gtgggaccgt gaaacccgcc agcgtctgcc acgttacgtc    360
tggataacac cggcaggctg gcagatgctg ggcgtcgaca tggtaaaact tcacgaacag    420
cagcagaaac gactgcgtga aagtgaaatc cgccagcagc tcattcggga aggtgttctg    480
cgtgaggatg aagatatctc cgtacatgcg gccagaaaac gctggtatct gcagcgcagc    540
caggatgcac tgaaacaccg tcgtgcaaaa gcggcagcca gtaagcgcgc cagacgcctg    600
aagaaactgc ctgccgacca gcagattcat gagatggcag agtatctcag gaagcgtctg    660
cctccggatg aagcctattt ttgttccgat gaccatctga agcgaatggc catcagggag    720
ttgcgtcagc ttgaactgac gctggctgcc ccgccaccgc actagacagc accattccct    780
cagcactgaa tcatcaccag cccctccggg gctttcggcg ctggttccgc tcagcccaaa    840
atccgcagta atcaccttaa atcccctcag aggggcatat ctgcccataa aaccacgcat    900
cagtcatcag aacatggcca cgtcgtttca gttatccaca taaatccgca aacaaagaac    960
tttaagaagc tgcaaacctg aaacagcaaa cctgcaatat agtcttaacc ccattattta   1020
atccccctgcg ttgcttcgcc gcagggaaaa tctttatctc tgagaccact gtgaacaaat   1080
acaagaggc cttcgcttgc agcggccaag gccgcgccgc tcagaatcta aaagcacctc    1140
ccacgctgat gcgcgggccc cgaacctcac cgttctgaaa ccacaacaaa aaacatcag    1200
gaataaaaac accacacaaa cgcagcaccg tacccacccc tcataactga aaagcgaggc    1260
cgccccgcc cgaagggcgg gaacaacatc gcttttaatt atgaatgttg taactacatt    1320
gtcatcgctg ccagtcttct ggctggaagt cctcagtaca cgctcgtaag cggccctgac    1380
ggcccgctaa cgcggagata cgccccgact gcgggtaaac ccttgtcggg accactccga    1440
ccgcgcacag aagctatttc atggctgaag cgggtatggc ttagcaggat ggggatgggt    1500
aaggtgaaat ctatcaatca gtaccggctg acgccgggct tcggcggttt tgtttctgtg    1560
ccatatgtaa caacggagtg ccgccttaca tgcgctgacg cgcattattt gccttgtttc    1620
gtctgaaagt aatcactatg attaaatatg attaacagct aatcggatat gcaaatgaaa   1680
aacaataccg cacaagcaac aaaagtaatt accgcgcatg tgccattacc tatggctgat    1740
aaagtcgacc agatggccgc cagactgaaa cgctcccggg gctggattat caaacaggcg    1800
ctttctgcat ggcttgccca ggaggaggag cgtaatcgcc tgacgctgga agccctggac    1860
gatgtgacat ccggacaggt tatcgaccat caggctgtac aggcctgggc ggacagcctc    1920
agtactgttt aaacttacaa cttgaccgaa tcaattagat gtctaacaat gccagggttt    1980
gacaatgtag aaacgtcgcc tagttggtca ctttctcctg ctaggatttt tcttaaaata   2040
cgtctcataa ttttgccgga tcttgtcttg ggcaagtcat ccactaaaat gatcaatttt    2100
ggtgcggcaa atggcccgat gtcttttcta acagtaaaga ccaaatgctt cttgatatct    2160
tgtaattcat catctgttgc ggtggaccaa ctagatttgt ttttcaacac cacaaatgca    2220
gcaactgctt gaccagtcaa gtcatcgttg aatccgacaa cagcacactc ggccacaatt    2280
ggatcttcga taatagcagc ctcaatttca gcggtagaca gacggtgacc agagacgttc    2340
accacatcgt ctacacgacc caaaatccag atataaccat ccttatcctt tgcagcacca    2400
tcaccagtga aatagtagcc agggtaaggg ttcaaataag tgtctagata cctatcatga    2460
tttttccaaa tagttcttgc aaatgatggc catgcagctt tgacggcaag gacaccctct    2520
gcgtggctgt tgttaagttc ttcaccagtg ttagggtcaa gaacaactgc atcaataccg    2580
aagaagggga atgaggcaga acccggtttc attggtgtaa caccaccagc cagcggggtg    2640
```

| | |
|---|---|
| accagatgcg aaccagattc tgtttgccag taggtgtcta caatgggat ttcatttta | 2700 |
| cctatttttt cagagtacca ctcccaaact tcagcagcaa ttggctcacc gaccgaaccc | 2760 |
| aagcaacgca aagattttaa ggaatgattt tcgatgtagg aatcaccagc tcttttcaac | 2820 |
| aaacgcaaag cagttggcgc aacataaaat tgggtgactt tgtgttcatc aataatatcc | 2880 |
| caataacggg agtaatttgg gtacgcagga gtcccttcaa agaccaaagt ggcacaacca | 2940 |
| tatagtaagg gaccataaac cacataagtg tggcctgtaa tccagccaat gtctccagct | 3000 |
| gtgaagaaaa cgtcttcttg gtgagtgtca aaagtgtagc gcatggtcaa caaagctccc | 3060 |
| agcaagtaac ctgcggtaga atgttgaaca cccttggggg caccagtaga accagacgta | 3120 |
| tacaacaaga ataatggatc ctcagaatca acggtgtgc atggatagta ggtcttgtat | 3180 |
| ttcttctttt ctgttgccca atccaaatct ctggggcat ggaaagcaac agatggattg | 3240 |
| ttggtctttc tataaaccaa gacgtgtctc acgcctgggg tctctcttag cgcgtcatca | 3300 |
| acaattcttt tagtctcaat gactttacca cctctgttgg attcatcgtg agtgatgaca | 3360 |
| actttagagt ccccatcgtt gatacgatct ctcaaggagt tggaagaaaa cccggcaaag | 3420 |
| actacggagt gaatggcacc gatacgggaa atggccaaca aggttatgat tgcttctggg | 3480 |
| accataggca tgtacacggc aacagtatcg cccttgcgaa cgcccataga gtaagtcagc | 3540 |
| acttgtgcca cttgacaaac ttcttcaagt agttccttgt aggtaatgga atagccttgg | 3600 |
| ccaggctcgt caccttcgaa ataatggct ttcttgttag gagtcttcaa ggcatgtctg | 3660 |
| tcaacacagt tgtaacaggc gtttaattgg ccgttgagga accatgcatt gttctggaag | 3720 |
| gagggcctgc ccgttttagg gtctgggatg aacaccttat cgaatggctt agaccagttt | 3780 |
| aaaaattggg tagctttaga accgaagaac ttagcagggt cttcaataga ctccttgtgc | 3840 |
| aagcgctgat agtcctgcaa cccgtccaag tgtggagaat agtgggtagc aattgcgggc | 3900 |
| tgcagtctat ctgagatggg ccgttgtggc acgatcttga ccgaagtcaa atgttcatac | 3960 |
| tcatgttcct tcttctgctg cgcagtggcg gcagactggg acattttgc tttcaacttg | 4020 |
| tcaatttcac ttgactgttc ttctagtttt gatgattgta cggcagaggg cgacatttta | 4080 |
| gcttccttag ctcctgaaaa tctcgataac tcaaaaaata cgcccggtag tgatcttatt | 4140 |
| tcattatggt gaaagttgga acctcttacg tgccgatcaa cgtctcattt tcgccaaaag | 4200 |
| ttggcccagg gcttcccggt atcaacaggg acaccaggat ttatttattc tgcgaagtga | 4260 |
| tcttccgtca caggtattta ttcggcgcaa agggcctcgt gatacgccta ttttataggg | 4320 |
| ttaatgtcag cggccgccag aacggtgcag tccctgacac atgctccggt cattctgtta | 4380 |
| actcatccac gtatgggaga acagttgttt aagctcagct gtcagttagt tgccgtttga | 4440 |
| gaacggaaac gggcaaagat aaagatgacc gcgaagcaga gtgcggggat cagttcagca | 4500 |
| gtggggatgt tgcccgccgc gtcactgaca aaacccatga ccggagtgac aataccgccg | 4560 |
| ccaataatgg tcataacgat gaaggacgaa ccatatttgg tgtcctggcc gagattctta | 4620 |
| atgcccagcg agaagattgt tgggtactga atcgacataa aggcgctgca taaagtcagg | 4680 |
| gctattaagc ccacatgacc gccagcgaag gctgagatca ggcacagtgc catagcgatt | 4740 |
| aatgcgtagg cggccaggac tttgtgtggt gcgaagcgac tgatgagcca ggtaccggtg | 4800 |
| aaacgaccaa taagaagca caccatggtt ccggttaaat agttagcggc aaagcctgca | 4860 |
| gtcatacctg gaatttcttc tacagcgtag cgaatcaaat agctccagca ggccgtttgt | 4920 |
| gcgccgacat agcagaattg cgctaatacc gcccagcgcc agtggcgaat acgcgccagg | 4980 |
| cgagaaagcg atgcggagaa cgatccttgt ttggcgtcac tgtgattatc actctgcaat | 5040 |

```
gccgggaatt tcgtcagcat gatcagcagg gcgaccagta acacgatagc cacgatgatc    5100
atataaggtg tctgtaccga taataccagg ctgtgtttat acgcactcaa ttgctctgga    5160
gacattttat cgagaacgtc ttgcgattga tgtggcacgt tagacaaaat aagactttgc    5220
ccaaagacaa ccgcgataat tgcgccaaac gagttaaatg tttgcgcaag atttaagcgg    5280
aagtgaccac tactttccgg ccctaatacc gtaacaaaag ggtttgcggc agtttccaga    5340
caacctaatc cggctgcaat aataaatagg ccaactaaaa acaaggtgta gttcattatt    5400
tctgcggcgg gccagaataa tgcagcaccc aaggcatata aaataacccc ggtaataatc    5460
cctgctttat aactgagttt tttcatcaat atcccagcag ggattgggat aatgaaataa    5520
ccaaagtaaa aggccgattg gatcaggcca gcctggaaat ttgtcagcgt aaaagcctgc    5580
tggaattgag gtaataaaat gtcgttaagg ttattggcta ccgcccaaag aaaaaacagt    5640
gagcacagca gcgcgaatgg aataatgtaa cttctgcttt gccctgcatc tttatctacc    5700
gcacggtaac tctgcgtttg tattgatgtg tttcccatag cttggttacc tccgggaaac    5760
gcggttgatt tgtttagtgg ttgaattatt tgctcaggat gtggcattgt caagggcgtg    5820
acggctcgcc tgacttctcg ttccagtgcc cccgtccgac agtcgagcgt gcgagcccat    5880
aatctcgcgc tggtgctgca taccgtggca acagcacag atcgctagg gaattcggca    5940 ctggccgtcg ttttacaacg tcgtgactgg gaaaaccctg gcgttaccca acttaatcgc    6000
cttgcagcac atccccctttt cgccagctgg cgtaatagcg aagaggcccg caccgatcgc    6060
ccttcccaac agttgcgcag cctgaatggc gaatggcgcg ataagctagc ttcacgctgc    6120
cgcaagcact cagggcgcaa gggctgctaa aggaagcgga acacgtagaa agccagtccg    6180
cagaaacggt gctgaccccg gatgaatgtc agctactggg ctatctggac aagggaaaac    6240
gcaagcgcaa agagaaagca ggtagcttgc agtgggctta catggcgata gctagactgg    6300
gcggttttat ggacagcaag cgaaccggaa ttgccagctg gggcgccctc tggtaaggtt    6360
gggaagccct gcaaagtaaa ctggatggct ttcttgccgc caaggatctg atggcgcagg    6420
ggatcaagat ctgatcaaga acaggatga ggatcgtttc gcatgattga acaagatgga    6480
ttgcacgcag gttctccggc cgcttgggtg gagaggctat tcggctatga ctgggcacaa    6540
cagacaatcg gctgctctga tgccgccgtg ttccggctgt cagcgcaggg gcgcccggtt    6600
ctttttgtca agaccgacct gtccggtgcc ctgaatgaac tccaagacga ggcagcgcgg    6660
ctatcgtggc tggccacgac gggcgttcct tgcgcagctg tgctcgacgt tgtcactgaa    6720
gcgggaaggg actggctgct attgggcgaa gtgccggggc aggatctcct gtcatctcac    6780
cttgctcctg ccgagaaagt atccatcatg gctgatgcaa tgcggcggct gcatacgctt    6840
gatccggcta cctgcccatt cgaccaccaa gcgaaacatc gcatcgagcg agcacgtact    6900 cggatgaag ccgtcttgt cgatcaggat gatctggacg aagagcatca ggggctcgcg    6960
ccagccgaac tgttcgccag gctcaaggcg cggatgcccg acggcgagga tctcgtcgtg    7020
acccatggcg atgcctgctt gccgaatatc atggtggaaa atggccgctt ttctggattc    7080
atcgactgtg gccggctggg tgtggcggac cgctatcagg acatagcgtt ggctacccgt    7140
gatattgctg aagagcttgg cggcgaatgg gctgaccgct tcctcgtgct ttacggtatc    7200
gccgctcccg attcgcagcg catcgccttc tatcgccttc ttgacgagtt cttctgagcg    7260
ggactctggg gttcgcgatg ataagctgtc aaacatgaga attacaactt atatcgtatg    7320
gggctgactt caggtgctac atttgaagag ataaattgca ctgaaatcta gaaataaaaa    7380
tagattttat ttttttgatg caggtcaaga ttgactcatt agaggtatcg gtgaggagac    7440
```

-continued

| | |
|---|---|
| actggaagag aagagatcgt tgtaatgctt ttcaaattaa cgtaaagcgg gtatatttcg | 7500 |
| gttgttatta gctgcgcaga gggtggcact ctgtggagca aagcggcgaa agccggacgg | 7560 |
| cagaatgcgc cataaggcat tcaggagaga tggcatttac gggcagtaag tcagaagacc | 7620 |
| gaagatgttc cggaagccat aaaaggaaaa cccccacaat ctttcgacga acttggcggg | 7680 |
| acggagaaag attatggggg cctcacagaa tacgggtaaa gtataatgaa accgtaccag | 7740 |
| agattcaacc ctgtgcagtg tataaataca cggcacaatc gctccgccat aagcgacagc | 7800 |
| ttgtggcagg tctgaagaat actccatata acgcagtaca ctggagtcag ttagcacccg | 7860 |
| aagagcagat ccgtttctgg aagactatg aagcgggaag ggcgaccact ttcctggttg | 7920 |
| aaccggaaag gaagcgcacg aagcgccgtc gcggtgagca ctccaccaaa cccaaatgcg | 7980 |
| aaaatccgtc ctggtatcgt cctgagcgct ataaggcgct gagcgggcag ctcgggcacg | 8040 |
| cctacaaccg tctggtgaaa aaggacccg | 8069 |

<210> SEQ ID NO 77
<211> LENGTH: 7979
<212> TYPE: DNA
<213> ORGANISM: Artificial Sequence
<220> FEATURE:
<223> OTHER INFORMATION: Plasmid

<400> SEQUENCE: 77

| | |
|---|---|
| gtgaccggcg agcagagcct gcgcatgcac atgtctctgc atccttttta cgtgcagaaa | 60 |
| cgaacgtatg ccgtcgcaa atatgctttc cgtccggaaa acaacgcct cctcgatgcc | 120 |
| atctggccgg ttctggtcag cttcagtgat gcgggcacac ataccgtagg catgagtgtt | 180 |
| tcccgtctgg ccagagaaat cagcccgaaa gacagcaagg ggaaggttat tccggaactg | 240 |
| gaagtgacgg tctcccgcct ttccgtttg ctggccgaac aggtacgttt tggtgtgctg | 300 |
| ggtgtttcag aggaaaccct gtgggaccgt gaaacccgcc agcgtctgcc acgttacgtc | 360 |
| tggataacac cggcaggctg gcagatgctg ggcgtcgaca tggtaaaact tcacgaacag | 420 |
| cagcagaaac gactgcgtga agtgaaatc cgccagcagc tcattcggga aggtgttctg | 480 |
| cgtgaggatg aagatatctc cgtacatgcg gccagaaaac gctggtatct gcagcgcagc | 540 |
| caggatgcac tgaaacaccg tcgtgcaaaa gcggcagcca gtaagcgcgc cagacgcctg | 600 |
| aagaaactgc ctgccgacca gcagattcat gagatggcag agtatctcag gaagcgtctg | 660 |
| cctccggatg aagcctattt tgttccgat gaccatctga gcgaatggc catcagggag | 720 |
| ttgcgtcagc ttgaactgac gctggctgcc ccgccaccgc actagacagc accattccct | 780 |
| cagcactgaa tcatcaccag cccctccggg gctttcggcg ctggttccgc tcagcccaaa | 840 |
| atccgcagta atcaccttaa atcccctcag aggggcatat ctgcccataa aaccacgcat | 900 |
| cagtcatcag aacatggcca cgtcgtttca gttatccaca taaatccgca aacaaagaac | 960 |
| tttaagaagc tgcaaacctg aaacagcaaa cctgcaatat agtcttaacc ccattattta | 1020 |
| atcccctgcg ttgcttcgcc gcagggaaaa tctttatctc tgagaccact gtgaacaaat | 1080 |
| acaaagaggc cttcgcttgc agcggccaag gccgcgccgc tcagaatcta aaagcacctc | 1140 |
| ccacgctgat gcgcgggccc cgaacctcac cgttctgaaa ccacaacaaa aaacatcag | 1200 |
| gaataaaaac accacacaaa cgcagcaccg tacccacccc tcataactga aaagcgaggc | 1260 |
| cgcccccgcc cgaagggcgg gaacaacatc gcttttaatt atgaatgttg taactacatt | 1320 |
| gtcatcgctg ccagtcttct ggctggaagt cctcagtaca cgctcgtaag cggccctgac | 1380 |
| ggcccgctaa cgcggagata cgccccgact gcgggtaaac ccttgtcggg accactccga | 1440 |

```
ccgcgcacag aagctatttc atggctgaag cgggtatggc ttagcaggat ggggatgggt    1500
aaggtgaaat ctatcaatca gtaccggctg acgccgggct tcggcggttt tgtttctgtg    1560
ccatatgtaa caacggagtg ccgccttaca tgcgctgacg cgcattattt gccttgtttc    1620
gtctgaaagt aatcactatg attaaatatg attaacagct aatcggatat gcaaatgaaa    1680
aacaataccg cacaagcaac aaaagtaatt accgcgcatg tgccattacc tatggctgat    1740
aaagtcgacc agatggccgc cagactggaa cgctcccggg gctggattat caaacaggcg    1800
ctttctgcat ggcttgccca ggaggaggag cgtaatcgcc tgacgctgga agccctggac    1860
gatgtgacat ccgacaggt tatcgaccat caggctgtac aggcctgggc ggacagcctc     1920
agtactgttt aaacttattt cttttttga gagaaaaatt ggttctctac agcagaaatg     1980
atggcaggta caacttctgg gttggccaaa gtagttaggt cacctagctg ttcggcttcg    2040
ttagaagcaa cctttcttag aactcttctc ataatctttc ctgaccttgt tcttggtaga    2100
tctctaacta gaataatggt ttttggtgag gcgaaaggac caatctcacc cctaacttgt    2160
aagatcaatt ctctacgtaa attatctggt gtgatgtgtt ctgcatcacc ttcagtagcg    2220
ttgttttgta gataaccatc ttttaggaa acatatgcaa cgacggtttg accggtcaat     2280
tcatctggaa taccgacaac agcagcttcc gagacgtttt cgtgatttga gatagatgct    2340
tcaatttctg atgtggataa tctatgaccg gaaacattta aacgtcgtc aactctaccc     2400 ctgatccagt agtaaccatc atgatctcta ccagcaccat cacctgtgaa atagtgacca    2460
ggataaggtt tcaagtaagt atccatgtaa cggtcgtggt ggttccaaac agatctagcc    2520
attgatggcc atggtgattt aacggcaagg acaccttcga catcattacc ttctaattcc    2580
acacctgtaa cagggtcaat gatacaagcg ttaataccaa agaatggcac ggtagcagaa    2640
ccaggttttg ttgggacagc acctgccaaa ggagcaatta aatgagaacc agactctgtt    2700
tgccacatag tgtcacaaat gacacagttt ttgttaccca cttttttcatg ataccattcc   2760 cataagtctg gagagattgg ttcaccgacg gaacccaaga cacgtaatga ggaagtgtca    2820
tatttggcaa tttcggcttc acctacacgt ttgattaatc ttaaagcagt tggagccaca    2880
tagaaatggg tagccttgtg acgttggata attctccaat atctaccata atctgggtag    2940
gcaggagtgg attcgaaaat tattgaggcg gtacccaagg ttaatggacc atatagagca    3000
taggtgtgac ccgtgatcca gccgacgtca ccggcagtga agagaacatc ttctgggtga    3060
atatcaaaaa cgtatctagt tgttaaagcg gcacctaata aataaccacc tgtagtgtga    3120
acgacaccct ttgagaaacc agtggaaccg gaagtgtata ataaaaatag aggatcttca    3180
gcgtcacatg aaacaggagg taggtaagtt ctctgcttag cggcctcctc atgccaccag    3240
taatctctac cggccttcat tggaatacct tcagtaccag ttctttggaa aaccaagata    3300
cgggaaacca aatcgactcc gttcaaacct tcgtcaacaa tttttttagt gttgatggtc    3360
ttaccacctc ttttaccttc atcacaagtg atgaccactt tagaattagc gtcaacgaca    3420
cgatctttca acgaaccagc ggagaaccca gcaaagacaa cagagtgaat agcaccaata   3480
cgagccacag ccaacatagc aatgaccgct tctggaatca ttggcaaata gatagccact    3540
gtgtcacctt tcttaacgcc ccagcttttt aagacaccag cgatttggga aacttttctg    3600
agtaattcac caaatgtgat gattttgttg tcggattcgt catcagcttc atagatcaaa    3660
gctggcttgt cgggattagc aaaggcatgt ctgtcaacac aattgtatga tgcattcaat    3720
ttaccgttca aaaaccatgc aacatcacca ttgttcaatg aaccagattg aactttggtg    3780
tatggagcat cccaatgcaa gtattcctta gccatcttat caaagaattt ttctggctca    3840
```

```
ttgatagatt gttgatacat ttcttgataa tgttgcatat cagtaacgta acccttgccg    3900
ggttggctgt tgtaaaaatg ttgaggagcc ttaagagcct ttacgttgtg agcttcataa    3960
actactttat gttccttgat tgtcatttta gcttccttag ctcctgaaaa tctcgataac    4020
tcaaaaaata cgcccggtag tgatcttatt tcattatggt gaaagttgga acctcttacg    4080
tgccgatcaa cgtctcattt tcgccaaaag ttggcccagg gcttcccggt atcaacaggg    4140
acaccaggat ttatttattc tgcgaagtga tcttccgtca caggtattta ttcggcgcaa    4200
agggcctcgt gatacgccta ttttttatagg ttaatgtcag cggccgccag aacggtgcag   4260
tccctgacac atgctccggt cattctgtta actcatccac gtatgggaga acagttgttt    4320
aagctcagct gtcagttagt tgccgtttga gaacggaaac gggcaaagat aaagatgacc    4380
gcgaagcaga gtgcgggdat cagttcagca gtggggatgt tgcccgccgc gtcactgaca    4440
aaacccatga ccggagtgac aataccgccg ccaataatgg tcataacgat gaaggacgaa    4500
ccatatttgg tgtcctggcc gagattctta atgcccagcg agaagattgt tgggtactga    4560
atcgacataa aggcgctgca taaagtcagg gctattaagc ccacatgacc gccagcgaag    4620
gctgagatca ggcacagtgc catagcgatt aatgcgtagg cggccaggac tttgtgtggt    4680
gcgaagcgac tgatgagcca ggtaccggtg aaacgaccaa taaagaagca caccatggtt    4740
ccggttaaat agttagcggc aaagcctgca gtcatacctg gaatttcttc tacagcgtag    4800
cgaatcaaat agctccagca ggccgtttgt gcgccgacat agcagaattg cgctaatacc    4860
gcccagcgcc agtggcgaat acgcgccagg cgagaaagcg atgcggagaa cgatccttgt    4920
ttggcgtcac tgtgattatc actctgcaat gccgggaatt tcgtcagcat gatcagcagg    4980
gcgaccagta acacgatagc cacgatgatc atataaggtg tctgtaccga taataccagg    5040
ctgtgtttat acgcactcaa ttgctctgga gacattttat cgagaacgtc ttgcgattga    5100
tgtggcacgt tagacaaaat aagactttgc ccaaagacaa ccgcgataat tgcgccaaac    5160
gagttaaatg tttgcgcaag atttaagcgg aagtgaccac tactttccgg ccctaatacc    5220
gtaacaaaag ggtttgcggc agtttccaga caacctaatc cggctgcaat aataaatagg    5280
ccaactaaaa acaaggtgta gttcattatt tctgcggcgg gccagaataa tgcagcaccc    5340
aaggcatata aaaataaccc ggtaataatc cctgctttat aactgagttt tttcatcaat    5400
atcccagcag ggattgggat aatgaaataa ccaaagtaaa aggccgattg gatcaggcca    5460
gcctggaaat ttgtcagcgt aaaagcctgc tggaattgag gtaataaaat gtcgttaagg    5520
ttattggcta ccgcccaaag aaaaaacagt gagcacagca gcgcgaatgg aataatgtaa    5580
cttctgcttt gccctgcatc tttatctacc gcacggtaac tctgcgtttg tattgatgtg    5640
tttcccatag cttggttacc tccgggaaac gcggttgatt tgtttagtgg ttgaattatt    5700
tgctcaggat gtggcattgt caagggcgtg acggctcgcc tgacttctcg ttccagtgcc    5760
cccgtccgac agtcgagcgt gcgagcccat aatctcgcgc tggtgctgca taccgtggca    5820
aacagcacag atcgcctagg gaattcggca ctggccgtcg ttttacaacg tcgtgactgg    5880
gaaaaccctg gcgttaccca acttaatcgc cttgcagcac atccccctttt cgccagctgg    5940 cgtaatagcg aagaggcccg caccgatcgc ccttcccaac agttgcgcag cctgaatggc    6000
gaatggcgcg ataagctagc ttcacgctgc cgcaagcact cagggcgcaa gggctgctaa    6060
aggaagcgga acacgtagaa agccagtccg cagaaacggt gctgacccccg gatgaatgtc    6120 agctactggg ctatctggac aagggaaaac gcaagcgcaa agagaaagca ggtagcttgc    6180
agtgggctta catggcgata gctagactgg gcggttttat ggacagcaag cgaaccggaa    6240
```

-continued

```
ttgccagctg gggcgccctc tggtaaggtt gggaagccct gcaaagtaaa ctggatggct    6300
ttcttgccgc caaggatctg atggcgcagg ggatcaagat ctgatcaaga gacaggatga    6360
ggatcgtttc gcatgattga acaagatgga ttgcacgcag gttctccggc cgcttgggtg    6420
gagaggctat tcggctatga ctgggcacaa cagacaatcg gctgctctga tgccgccgtg    6480
ttccggctgt cagcgcaggg gcgcccggtt cttttgtca agaccgacct gtccggtgcc    6540
ctgaatgaac tccaagacga ggcagcgcgg ctatcgtggc tggccacgac gggcgttcct    6600
tgcgcagctg tgctcgacgt tgtcactgaa gcgggaaggg actggctgct attgggcgaa    6660
gtgccggggc aggatctcct gtcatctcac cttgctcctg ccgagaaagt atccatcatg    6720
gctgatgcaa tgcggcggct gcatacgctt gatccggcta cctgcccatt cgaccaccaa    6780
gcgaaacatc gcatcgagcg agcacgtact cggatggaag ccggtcttgt cgatcaggat    6840
gatctggacg aagagcatca ggggctcgcg ccagccgaac tgttcgccag gctcaaggcg    6900
cggatgcccg acgcgagga tctcgtcgtg acccatggcg atgcctgctt gccgaatatc    6960
atggtggaaa atggccgctt ttctggattc atcgactgtg gccggctggg tgtggcggac    7020
cgctatcagg acatagcgtt ggctacccgt gatattgctg aagagcttgg cggcgaatgg    7080
gctgaccgct tcctcgtgct ttacggtatc gccgctcccg attcgcagcg catcgccttc    7140
tatcgccttc ttgacgagtt cttctgagcg ggactctggg gttcgcgatg ataagctgtc    7200
aaacatgaga attacaactt atatcgtatg gggctgactt caggtgctac atttgaagag    7260
ataaattgca ctgaaatcta gaaataaaaa tagattttat ttttttgatg caggtcaaga    7320
ttgactcatt agaggtatcg gtgaggagac actggaagag aagagatcgt tgtaatgctt    7380
ttcaaattaa cgtaaagcgg gtatatttcg gttgttatta gctgcgcaga gggtggcact    7440
ctgtggagca aagcggcgaa agccggacgg cagaatgcgc cataaggcat tcaggagaga    7500
tggcatttac gggcagtaag tcagaagacc gaagatgttc cggaagccat aaaaggaaaa    7560
cccccacaat ctttcgacga acttggcggg acggagaaag attatggggg cctcacagaa    7620
tacgggtaaa gtataatgaa accgtaccag agattcaacc ctgtgcagtg tataaataca    7680
cggcacaatc gctccgccat aagcgacagc ttgtggcagg tctgaagaat actccatata    7740
acgcagtaca ctggagtcag ttagcacccg aagagcagat ccgtttctgg gaagactatg    7800
aagcgggaag ggcgaccact ttcctggttg aaccggaaag gaagcgcacg aagcgccgtc    7860
gcggtgagca ctccaccaaa cccaaatgcg aaaatccgtc ctggtatcgt cctgagcgct    7920
ataaggcgct gagcgggcag ctcgggcacg cctacaaccg tctggtgaaa aaggacccg    7979
```